(12) United States Patent
Cool et al.

(10) Patent No.: US 10,493,012 B2
(45) Date of Patent: *Dec. 3, 2019

(54) COSMETIC USE OF HEPARAN SULPHATE

(71) Applicants: Agency for Science, Technology and Research, Singapore (SG); L'Oreal, Paris (FR)

(72) Inventors: Simon Cool, Singapore (SG); Victor Nurcombe, Singapore (SG); Charbel Bouez, Singapore (SG); Diah Saraswati Bramono, Singapore (SG)

(73) Assignees: Agency for Science, Technology and Research, Singapore (SG); L'Oreal, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 15/527,995

(22) PCT Filed: Nov. 19, 2015

(86) PCT No.: PCT/SG2015/050462
§ 371 (c)(1),
(2) Date: May 18, 2017

(87) PCT Pub. No.: WO2016/080915
PCT Pub. Date: May 26, 2016

(65) Prior Publication Data
US 2017/0326059 A1 Nov. 16, 2017

(30) Foreign Application Priority Data
Nov. 19, 2014 (SG) .......................... 10201408006R

(51) Int. Cl.
*A61K 8/73* (2006.01)
*A61Q 19/08* (2006.01)
*A61Q 19/00* (2006.01)
*C08B 37/00* (2006.01)

(52) U.S. Cl.
CPC .............. *A61K 8/73* (2013.01); *A61Q 19/007* (2013.01); *A61Q 19/08* (2013.01); *C08B 37/0075* (2013.01); *A61K 2800/10* (2013.01)

(58) Field of Classification Search
None
See application file for complete search history.

(56) References Cited

U.S. PATENT DOCUMENTS

| | | | |
|---|---|---|---|
| 10,266,612 | B2 | 4/2019 | Nurcombe et al. |
| 2006/0183712 | A1 | 8/2006 | McKeehan et al. |
| 2010/0168055 | A1 | 7/2010 | Laboureau et al. |
| 2011/0288047 | A1* | 11/2011 | De Ambrosi ............ A61K 8/73 514/56 |
| 2013/0071443 | A1 | 3/2013 | Cool et al. |
| 2016/0115251 | A1 | 4/2016 | Nurcombe et al. |
| 2017/0319615 | A1 | 11/2017 | Cool et al. |

FOREIGN PATENT DOCUMENTS

| | | |
|---|---|---|
| EP | 0509517 A2 | 10/1992 |
| JP | H0240399 A | 2/1990 |
| WO | WO-92/02539 A1 | 2/1992 |
| WO | WO-93/19096 A1 | 9/1993 |
| WO | WO-1996/023003 A1 | 8/1996 |
| WO | WO-2010/011185 A1 | 1/2010 |
| WO | WO-2010/029278 A2 | 3/2010 |
| WO | WO-2010/030241 A1 | 3/2010 |
| WO | WO-2010/030244 A1 | 3/2010 |
| WO | WO-2010/057710 A2 | 5/2010 |
| WO | WO-2014/185858 A1 | 11/2014 |

OTHER PUBLICATIONS

Belting, M. Heparan sulfate proteoglycan as a plasma membrance carrier, Trends in Biochemical Sciences, 28(3): 145-151 (2003).
Jackson, W. et al., Concise review: clinical translation of wound healing, Stem Cells Translat. Med., 1: 44-50 (2012).
Kundrotas, G., Surface markers distinguishing mesenchymal stem cells from fibroblasts, Acta Medica Lituanica, 19(2): 75-79 (2012).
Ackermann, et al., Priming with proangiogenic growth factors and endothelial progenitor cells improves revascularization in linear diabetic wounds et al., Int. J. Mol. Med., 33: 833-839 (2014).
Baird, A. et al., Receptor- and heparin-binding domains of basic fibroblast growth factor, Proc. Natl. Acad. Sci. USA, 85:2324-2328 (1988).
Bramono, D.S. et al., The Effect of Human Bone Marrow Stroma-Derived Heparan Sulfate on the Ex Vivo Expansion of Human Cord Blood Hematopoietic Stem Cells, Pharm Res., 28:1385-1394 (2011).
Brickman, Y.G. et al., Heparan sulfates mediate the binding of basic fibroblast growth factor to a specific receptor on neural precursor cells, Journal of Biological Chemistry, 270(42): 24941-24948 (1995).
Correa, et al., A graph-structural method for prediction of polymer properties, Brazilian Journal of Chemical Engineering, 21(4): 621-628 (2004).
Desgranges, P. et al., Beneficial use of fibroblast growth factor 2 and RGTA, a new family of heparan mimics, for endothelialization of PET prostheses, Journal of Biomedical Materials Research, 58(1): 1-9 (2000).

(Continued)

*Primary Examiner* — Jessica Worsham

(74) *Attorney, Agent, or Firm* — Choate, Hall & Stewart LLP; Kristen C. Buteau; Nicholas J. Pace

(57) ABSTRACT

Affinity purification of fibroblast growth factor 2-binding heparan sulphate from porcine mucosa (HS8) is disclosed. Also disclosed is a process for the care of keratinous material(s), comprising the application or administration of HS8, or a composition comprising thereof, to keratinous material(s). The composition may be used to improve the condition of skin, such as smoothing the skin, restoring skin elasticity and firmness, or decreasing or preventing wrinkles, and may be formulated for topical or transdermal administration.

11 Claims, 36 Drawing Sheets

Specification includes a Sequence Listing.

(56) References Cited

OTHER PUBLICATIONS

Dombrowski, C. et al., Heparan sulfate mediates the proliferation and differentiation of rat mesenchymal stem cells, Stem Cells and Development, 18(4): 661-670 (2009).
Dominici, M. et al., Minimal criteria for defining multipotent mesenchymal stromal cells. The International Society for Cellular Therapy position statement, Cytotherapy, 8(4): 315-317 (2006).
Gallo, R.L. et al., The Potential Role of Topically Applied Heparan Sulfate in the Treatment of Photodamage, J. Drugs Dermatol., 14(7): 669-674 (2015).
Gandhi, et al., The structure of glycosaminoglycans and their interactions with proteins, Chem. Biol. Drug Des., 72: 455-482 (2008).
Gang, E.J. et al., SSEA-4 identifies mesenchymal stem cells from bone marrow, Blood, 109(4): 1743-1751 (2007).
Garcia-Filipe et al., RGTA OTR4120, a heparan sulfate mimetic, is a possible long-term active agent to heal burned skin, J. Biomed. Mater. Res. A, 80(1): 75-84 (2007).
Gronthos, S. et al., Differential Cell Surface Expression of the STRO-1 and Alkaline Phosphatase Antigens on 3Discrete Developmental Stages in Primary Cultures of Human Bone Cells, Journal of Bone and Mineral Research, 14(1): 47-56 (1999).
Helledie, T. et al., Heparan sulfate enhances the self-renewal and therapeutic potential of mesenchymal stem cells from human adult bone marrow, Stem Cells Dev., 21(11):1897-1910 (2012).
International Search Report for PCT/SG2013/000201, 4 pages (dated Aug. 23, 2013).
International Search Report for PCT/SG2015/050462, 6 pages (dated Jan. 27, 2016).
International Search Report for PCT/SG2015/050464, 6 pages (dated Jan. 27, 2016).
Jackson, R.A. et al., Coordinated fibroblast growth factor and heparan sulfate regulation of osteogenesis, Gene, 379: 79-91 (2006).
Jackson, R.A. et al., The use of heparan sulfate to augment fracture repair in a rat fracture model, J Orthop Res., 24(4):636-644 (2006).
Jackson, R.L. et al., Glycosaminoglycans: Molecular Properties, Protein Interactions, and Role in Physiological Processes, Physiol. Rev., 71(2): 481-539 (1991).
Maccarana, M. et al., Minimal Sequence in Heparin/Heparan Sulfate Required for Binding of Basic Fibroblast Growth Factor, The Journal of Biological Chemistry, 268(32): 23898-23905 (1993).
Manton, K.J. et al., Disruption of heparan and chondroitin sulfate signaling enhances mesenchymal stem cell-derived osteogenic differentiation via bone morphogenetic protein signaling Pathways, Stem Cells, 25(11): 2845-2854 (2007).

Murali, S. et al., Comparative assessment of the effects of gender-specific heparan sulfates on mesenchymal stem cells, The Journal of Biological Chemistry, 286(20): 17755-17765 (2011).
Murali, S. et al., Purification and characterization of heparan sulfate from human primary osteoblasts, Journal of Cellular Biochemistry, 108(5): 1132-1142 (2009).
Nakamizo, S. et al., Topical Treatment with Basic Fibroblast Growth Factor Promotes Wound Healing and Barrier Recovery Induced by Skin Abrasion, Skin Pharmacol. Physiol., 26(1): 22-29 (2012).
Ori, A. et al., Identification of Heparin-binding Sites in Proteins by Selective Labeling, Mol. Cell Proteomics, 8(10): 2256-2265 (2009).
Rider, D.A. et al., Selection using the alpha-1 integrin (CDF94a) enhances the multipotentiality of the mesenchymal stem cell population from heterogeneous bone marrow stromal cells, J. Mol. Hist., 38: 449-458 (2007).
Saksela, O. et al., Endothelial Cell-derived heparan sulfate binds basic fibroblast growth factor and protects it from proteolytic degradation, The Journal of Cell Biology, 107: 743-751 (1988).
Schmidt, A. et al., Basic Fibroblast Growth Factor Controls Migration in Human Mesenchymal Stem Cells, Stem Cells, 24(7): 1750-1758 (2006).
Schultz, G.S. et al., Interactions between extracellular matrix and growth factors in wound healing, Wound Repair and Regeneration, 17(2): 153-162 (2009).
Sogabe, Y. et al., Basic fibroblast growth factor stimulates human keratinocyte motility by Rac activation, Wound Rep. Regen., 14(4): 457-462 (2006).
Tong, M. et al., Diabetes-Impaired Wound Healing Is Improved by Matrix Therapy with Heparan Sulfate Glycosaminoglycan Mimetic OTR4120 in Rats, Diabetes, 61(10): 2633-2641 (2012).
Wijesinghe, S.J. et al., Affinity Selection of FGF2-Binding Heparan Sulfates for Ex Vivo Expansion of Human Mesenchymal Stem Cells, J Cell Physiol., 232(3): 566-575 (2017).
Written Opinion for PCT/SG2013/000201, 6 pages (dated Aug. 23, 2013).
Written Opinion for PCT/SG2015/050462, 7 pages (dated Jan. 27, 2016).
Written Opinion for PCT/SG2015/050464, 7 pages (dated Jan. 27, 2016).
Zakine, G. et al., Matrix Therapy with RGTA OTR4120 Improves Healing Time and Quality in Hairless Rats with Deep Second-Degree Burns, Plast. Reconstr. Surg., 127(2): 541-550 (2011).
Fromm, J.R. et al., Pattern and Spacing of Basic Amino Acids in Heparin Bing Sites, Archives of Biochemistry and Biophysics, 343(1): 92-100 (1997).
Shriver, Z., Heparin and Heparan Sulfate: Analyzing Structure and Microheterogeneity, Handb Exp Pharmacol., (207): 159-176. (2012).

* cited by examiner

|   | Residue/ Size | Sequence | Reference |
|---|---|---|---|
| 1 | 248-254/ 7aa | $^{248}$YKRSRYT$^{254}$ -paper<br>Have to be $^{248}$YRSRKYT$^{254}$ | Lee et al, 2007 |
| 2 | 261-277/17aa | $^{261}$KRTGQYKLGSKTGPGQK$^{277}$ | |
| 3 | 260-277aa/18aa | $^{260}$LKRTGQYKLGSKTGPGQK$^{277}$ | Hileman et al, 1998 |
| 5 | 235-262/ 28aa | $^{235}$FFFERLESNNYNTYRSRKYTSWYVALKR$^{262}$ | Baird et al, 1998 |
| 6 | 157-172/ 16aa | $^{157}$GHFKDPKRLYCKNGGF$^{172}$ | Gandhi et al, 2008 |
| 8 | 185-194/ 10aa | $^{185}$VREKSDPHIK$^{194}$ | Kinsella, et al, 1998 |
| 9 | 250-259/ 10aa | $^{250}$SRKYTSWYVA$^{259}$ | |
| 10 | 260-273/14aa | $^{260}$LKRTGQYKLGSKTG$^{273}$ | |
| 11 | 260-280/ 21aa | $^{260}$LKRTGQYKLGSKTGPGQKAIL$^{280}$ | Ashikari-Hada et al, 2004 |
| 13 | 168-169,223,261-277-20aa | $^{168}$KN$^{169}$ $^{223}$R $^{261}$KRTGQYKLGSKTGPGQK$^{277}$ | Ori et al, 2009, Faham et al, 1996, Thomson et al, 1985 and Baird et al, 1998 |
| 14 | 235-262/28aa | $^{235}$FFFERLESNNYNTYRSRKYTSWYVALKR$^{262}$ | |
| 15 | 216-225/10aa | $^{216}$LAMKEDGRLL$^{225}$ | |

Figure 3

MVGVGGGDVE DVTPRPGGCQ ISGRGARGCN GIPGAAAWEA ALPRRRPRRH PSVNPRSRAA
GSPRTRGRRT EERPSGSRLG DRGRGRALPG GRLGGRGRGR APERVGGRGR GRGTAAPRAA
PAARGSRPGP AGTMAAGSIT TLPALPEDGG SGAFPP<u>GHFK DPKRLYCKNG G</u>FFLRIHPDG
RVDGVREKSD PHIKLQLQAE ERGVVSIKGV CANRYLAMKE DGRLLASKCV TDECFFFERL
ESNNYNTYRS RKYTSWYVAL KRTGQYKLGS KTGPGQKAIL FLPMSAKS

Figure 12

| DISACCHARIDE | %E10 GAG |
|---|---|
| IdoA/GlcA-AMann$_R$ | 12.9 |
| IdoA(2S)-AMann$_R$ | 53.4 |
| GlcA-AMann$_R$(6S) | 10.25 |
| IdoA-AMann$_R$(6S) | 3.4 |
| IdoA(2S)-AMann$_R$(6S) | 18.7 |
| GlcA(2S)-AMann$_R$ | 1.0 |
| GlcA-AMann$_R$(3S) | 0.30 |
| GlcA-AMann$_R$(3,6S) | 0.15 |
| UNKNOWN | 0.0 |

Figure 13

| PEAK NUMBER | DISACCHARIDE | % in E10 GAG |
|---|---|---|
| 1 | ΔHexUA-GlcNAc | 44.8 |
| 3 | ΔHexUA-GlcNSO$_3$ | 21.5 |
| 2 | ΔHexUA-GlcNAc(6S) | 8.0 |
| 7 | ΔHexUA(2S)-GlcNAc | 2.4 |
| 4 | ΔHexUA-GlcNSO$_3$(6S) | 4.0 |
| 5 | ΔHexUA(2S)-GlcNSO$_3$ | 12.4 |
| 8 | ΔHexUA(2S)-GlcNAc(6S) | 0.2 |
| 6 | ΔHexUA(2S)-GlcNSO$_3$(6S) | 4.1 |
| 9 | unknown | 2.4 |

Figure 14

| Disaccharide | Celsus HS | HS3 (848/HS3/001) | HS8 |
|---|---|---|---|
| ΔHexUA,2S-GlcNS,6S | 8.3 | 14.8 | 12.7 |
| ΔHexUA,2S-GlcNS | 5.1 | 4.9 | 7.2 |
| ΔHexUA-GlcNS,6S | 9.1 | 11.1 | 15.5 |
| ΔHexUA,2S-GlcNAc,6S | 3.3 | 4.8 | 6.5 |
| ΔHexUA-GlcNS | 26.9 | 22.2 | 15.7 |
| ΔHexUA,2S-GlcNAc | 1.6 | 1 1 | 1.0 |
| ΔHexUA-GlcNAc,6S | 10.8 | 10.1 | 8.9 |
| ΔHexUA-GlcNAc | 34.9 | 31.0 | 32.5 |
| Total | 100.0 | 100.0 | 100.0 |

Mean average of duplicate analyses of duplicate hydrolysates
Normalised weight percentage disaccharide

COSMETIC USE OF HEPARAN SULPHATE

FIELD OF THE INVENTION

The present invention relates to heparan sulphates and particularly, although not exclusively, to heparan sulphates that bind FGF2, in particular HS8, and their cosmetic use.

BACKGROUND TO THE INVENTION

Skin constitutes the largest organ of the human body, serving as a protective barrier against physical injury, radiation and temperature. The rejuvenation of skin is regulated by various mechanisms including cell-cell interactions, extracellular matrix production and a plethora of polypeptide factor production. One of the major growth factors known to be crucial for skin maintenance, fibroblast growth factor-2 (FGF-2), belongs to a family of similar heparin-binding proteins made by many types of cell, including fibroblasts, melanocytes, endothelial cells. FGF-2 has both a proliferative and motile effect on keratinocytes.

Human skin is made up mainly of two main layers, namely the dermis and the epidermis that superficially covers the dermis. The dermis provides the epidermis with a solid support. It is also its nourishing element. It is made up mainly of fibroblasts and an extracellular matrix composed mainly of collagen, elastin and a substance known as ground substance. These components are synthesized by the fibroblasts.

The skin provides a barrier against external attacks, in particular chemical, mechanical or infectious attacks, and, therefore, a number of defensive reactions against environmental factors (climate, ultraviolet rays, tobacco, etc) and/or xenobiotic, such as, for example, microorganisms, occur therein. This property is referred to as barrier function and is mainly provided by the most superficial layer of the epidermis, namely the horny layer, referred to as the stratum corneum. Detrimental changes in the barrier can be reflected by cutaneous discomfort, sensory phenomena or cutaneous dryness measured by imperceptible water loss.

Skin is the primary barrier between the organism and the outside world. It must both prevent invasion by pathogens but at the same time, prevent water and electrolyte loss from the body. Agents that increase and repair the barrier function of keratinocytes, have great potential as cosmetic skin improving agents. Augmentation of the barrier function increases the skins hydration level and is known to improve the appearance of the skin and lead to a healthier cosmetic appearance.

FGF-2 is detected at the dermis and epidermis near the wound edge (Werner & Grose, Physio Rev 2003). It is also a key regulator in keratinocyte migration during wound healing via its receptor FGF-R1 (Meyer et al, J Cell Sci 2012). FGF-2 binds strongly to heparan sulfate (HS) proteoglycan on the basement membrane of the epidermis and surrounding the hair follicle cross-section (Friedl et al, Am J Pathol 1997).

Cosmetological and dermatological preparations making use of heparan sulfate are known from EP 2 346 573 B1.

SUMMARY OF THE INVENTION

The Applicants have now discovered that surprisingly an heparan sulphate compound, heparan sulphate HS8, provides benefits for taking care of keratin materials, such as the skin. These benefits are advantageously anti-ageing and moisturizing effects.

The present invention concerns a heparan sulphate preparation, heparan sulphate HS8. HS8 has been found to bind FGF2. HS8 refers to a novel class of structurally and functionally related isolated heparan sulphate. The inventors have identified several closely related members of the HS8 class that have the common property of binding to heparin binding domains derived from FGF2 that share a short consensus sequence (YCKNGGF).

In one aspect of the present invention an heparan sulphate HS8 is provided. HS8 may be provided in isolated form or in substantially purified form. This may comprise providing a composition in which the heparan sulphate component is at least 80% HS8, more preferably one of at least 85%, 90%, 95%, 96%, 97%, 98%, 99% or 100%.

In preferred embodiments, HS8 is capable of binding a peptide or polypeptide having the amino acid sequence of YCKNGGF (SEQ ID NO: 2). The peptide may have one or more additional amino acids at one or both ends of this sequence. For example, the peptide may have any of 1, 2, 3, 4, 5, 6, 7, 8, 9, 10, 11, 12, 13, 14, 15, 16, 17, 18, 19, 20 or more amino acids at one or both end of this sequence.

In some embodiments, HS8 is capable of binding a peptide or polypeptide having, or consisting of, the amino acid sequence of any one of:

```
                                        (SEQ ID NO: 2)
YCKNGGF,
or
                                        (SEQ ID NO: 1)
GHFKDPKRLYCKNGGF.
```

In other embodiments the polypeptide is an FGF2 protein. In some embodiments HS8 binds to a peptide having or consisting of the amino acid sequence of any of SEQ ID NOs:1, 2 or FGF2 protein with a $K_D$ of less than 100 µM, more preferably less than one of 50 µM, 40 µM, 30 µM, 20 µM, or 10 µM.

HS8 may be obtained, identified, isolated or enriched according to the inventors' methodology described herein, which may comprise the following steps:
(i) providing a solid support having polypeptide molecules adhered to the support, wherein the polypeptide comprises a heparin-binding domain having the amino acid sequence of YCKNGGF;
(ii) contacting the polypeptide molecules with a mixture comprising glycosaminoglycans such that polypeptide-glycosaminoglycan complexes are allowed to form;
(iii) partitioning polypeptide-glycosaminoglycan complexes from the remainder of the mixture;
(iv) dissociating glycosaminoglycans from the polypeptide-glycosaminoglycan complexes;
(v) collecting the dissociated glycosaminoglycans.

In some embodiments the polypeptide adhered to the support may comprise or consist of an amino acid sequence selected from

```
                                        (SEQ ID NO: 2)
YCKNGGF,
or
                                        (SEQ ID NO: 1)
GHFKDPKRLYCKNGGF.
```

In the inventors' methodology the mixture may comprise glycosaminoglycans obtained from commercially available sources. One suitable source is a heparan sulphate fraction, e.g. a commercially available heparan sulphate. One suitable heparan sulphate fraction can be obtained during isolation of heparin from porcine intestinal mucosa (e.g. Celsus Laboratories Inc.—sometimes called "Celsus HS").

Other suitable sources of heparan sulphate include heparan sulphate from any mammal (human or non-human), particularly from the kidney, lung or intestinal mucosa. In some embodiments the heparan sulphate is from pig (porcine) or cow (bovine) intestinal mucosa, kidney or lung.

In another aspect of the present invention a composition comprising HS8 according to any one of the aspects above and FGF2 protein is provided.

In one aspect of the present invention a cosmetic composition is provided comprising HS8 in accordance with the aspects described above. The cosmetic composition may further comprise a cosmetically acceptable carrier, adjuvant or diluent.

In some embodiments the cosmetic composition may further comprise FGF2 protein.

Preferably, the HS8 and FGF2 protein are respectively provided in cosmetically effective amounts. In some embodiments methods and uses according to the present invention further comprise the step of formulating cosmetically effective amounts of HS8, and/or FGF2 protein as a cosmetic composition comprising the HS8, and/or FGF2 protein and a cosmetically acceptable carrier, adjuvant or diluent, wherein the cosmetic composition is optionally administered to the subject.

In some aspects of the present invention heparan sulphate HS8 is provided for use in cosmetic methods. Such methods may involve the application or administration of HS8, or a composition comprising HS8, to a keratinous material, in particular to the skin of a subject. In some aspects of the present invention a cosmetic composition comprising HS8 is provided. A cosmetic composition may be a composition comprising HS8 formulated for use as a cosmetic agent. Suitable formulations are described herein including topical formulations comprising HS8 and a cosmetically acceptable carrier.

In one aspect of the present invention a cosmetic method comprising administration of heparan sulphate HS8 to a subject is provided. In another aspect of the present invention a composition formulated for administration to the skin and comprising heparan sulphate HS8 is provided. In another aspect of the present invention a cosmetic method of regulating skin condition, comprising applying to the skin of a mammal a safe and effective amount of a cosmetic composition comprising heparan sulphate HS8, is provided.

In one aspect of the present invention a process or method is provided for the care of keratinous material(s), the process or method comprising the application or administration of heparan sulphate HS8, or a composition comprising HS8, to keratinous material(s).

In another aspect of the present invention a cosmetic method of regulating skin condition is provided, the method comprising applying or administering to the skin of a mammal a safe and effective amount of heparan sulphate HS8, or a composition comprising HS8.

In another aspect of the present invention a cosmetic composition comprising a safe and effective amount of heparan sulphate HS8 and a cosmetically acceptable carrier is provided. In some embodiments the cosmetic composition may be formulated as skin lotion, sunscreen, lipstick, foundation or nail polish.

In another aspect of the present invention the use of heparan sulphate HS8, or a composition comprising HS8, as anti-ageing agent (for keratinous material(s), preferably of the skin) is provided. In another aspect of the present invention heparan sulphate HS8, or a composition comprising HS8, is provided for use in a method of anti-ageing treatment (for keratinous material(s), preferably of the skin).

In another aspect of the present invention the use of heparan sulphate HS8, or a composition comprising HS8, as moisturizing agent (for keratinous material(s), preferably of the skin) is provided. In another aspect of the present invention heparan sulphate HS8, or a composition comprising HS8, is provided for use in a method of moisturizing treatment (for keratinous material(s), preferably of the skin).

In some embodiments heparan sulphate HS8 is present in the composition in a content ranging from 0.0001% to 5% of the total weight of the composition, preferably from 0.0001% to 2%, and still preferably from 0.001 to 2%.

In some embodiments the application or administration of heparan sulphate HS8 is intended to decrease and/or prevent the signs of the ageing of the keratinous material(s). In some embodiments the application or administration of heparan sulphate HS8 is intended to maintain and/or stimulate moisturization and/or combat drying-out of the keratinous material(s). In some embodiments the application or administration of heparan sulphate HS8 is intended to improve skin appearance and/or feel. In some embodiments the application or administration of heparan sulphate HS8 is intended to regulate visible and/or tactile discontinuities in skin texture. In some embodiments the application or administration of heparan sulphate HS8 is intended to:

(i) decrease and/or prevent the characteristics of wrinkles, small wrinkles and/or fine lines of the skin;
(ii) improve and/or decrease the microrelief of the skin;
(iii) smooth the skin;
(iv) improve the density of the skin;
(v) maintain and/or restore skin elasticity;
(vi) maintain and/or restore skin firmness;
(vii) maintain and/or restore the cohesion of skin compartments, in particular the cohesion of the derm within the skin.

In some embodiments the heparan sulphate HS8, or composition comprising HS8 is formulated for topical or transdermal administration. In some embodiments the heparan sulphate HS8, or composition comprising HS8, is formulated as a gel, spray, mist, aerosol, foam, paste, ointment, cream, lotion, salve, conditioner, cosmetic, lipstick, foundation, nail polish, oil, aqueous solution, suspension, emulsion, dispersion, patch, adhesive plaster, bandage, dressing, depot, or reservoir.

In processes and methods of the present invention the heparan sulphate HS8 is preferably used in isolated or substantially purified form. When used in a composition it is preferred that the composition does not contain another, different, form of heparan sulphate.

The present invention concerns cosmetic uses of heparan sulphate HS8. "Cosmetic" as used herein refers to non-therapeutic use. Cosmetic methods preferably do not refer to methods for treatment of the human or animal body by surgery or therapy, or diagnostic methods practised on the human or animal body (e.g. according to Article 53(c) EPC). In some embodiments they do not involve the treatment of a disease. Cosmetic methods and uses may be intended, for example, to regulate a skin condition, to improve the appearance of the keratinous material, improve the texture of the keratinous material, improve the hydration level of the keratinous material, prevent a reduction in skin barrier function, or reinforce skin barrier function. Increased hydration level is known to improve the appearance of the skin and lead to a healthier cosmetic appearance. In preferred embodiments the keratinous material is skin.

In another aspect of the present invention an assembly or kit for packaging and applying a cosmetic composition for application to keratinous material(s) is provided, the assembly or kit comprising a device for packaging the said cosmetic composition for application to keratinous material(s) as described herein.

Further aspects of the present invention are set out below.

In one aspect of the present invention a GAG is provided having high binding affinity for FGF2. More preferably the GAG is a heparan sulphate (HS). In one embodiments the HS was isolated from a GAG mixture obtained from porcine intestinal mucosa (available from Celsus Laboratories Inc, Cincinnatti, USA, e.g. INW-08-045, Heparan Sulphate I, Celsus Lab Inc, HO-03102, HO-10595, 10×100 mg) by following the methodology described herein in which a polypeptide comprising the heparin-binding domain of FGF2 containing the amino acid sequence of YCKNGGF was attached to a solid support and GAG-polypeptide complexes were allowed to form. Dissociation of the GAG component from the GAG-polypeptide complexes led to isolation of a unique HS herein called "HS8". In one embodiment, HS8 is the HS isolated by attaching the polypeptide GHFKDPKRLYCKNGGF (SEQ ID NO: 1) to a solid support, allowing GAG-polypeptide complexes to form, and dissociating the GAG component from the GAG-polypeptide complexes.

It is the inventors belief that HS8 can be obtained from HS fractions obtained from a plurality of sources, including mammalian (human and non-human) tissue and/or extracellular matrix.

Accordingly, in one aspect of the present invention HS8 is provided. HS8 may be provided in isolated or purified form.

In yet another aspect of the present invention a cosmetic composition comprising HS8 is provided, optionally in combination with a cosmetically acceptable carrier, adjuvant or diluent. In some embodiments cosmetic compositions or medicaments may further comprise FGF2 protein.

As shown herein, HS8 has the property of stabilising FGF2, and thereby prolonging its action. HS8 prevents FGF2 from degradation in culture medium (FIG. 28).

Optionally, aspects and embodiments of the present do not include HS1 or HS2 (as described by Brickman et al (Glycobiology Vo. 8 No. 5 pp. 463-471, 1998 and in WO2010/011185). In some embodiments heparan sulphates according to the present invention do not include HS2, and/or a heparan sulphate having a nitrous acid disaccharide digestion profile according to FIG. 13 and/or a heparan sulphate having a nitrous acid disaccharide digestion profile according to FIG. 14.

DESCRIPTION OF PREFERRED EMBODIMENTS

The inventors have identified a novel class of heparan sulphate molecules, called HS8.

They have shown that HS8 has the following advantageous properties:

Enhances dermal fibroblast proliferation in 10% FCS medium

Down-regulates keratinocyte differentiation markers K10, transglutaminase-1 and involucrin, mirroring the effect of retinoic acid, a well-known anti-aging active Enhances the number of motile and hypermotile keratinocytes.

Modulation of basal keratinocyte proliferation.

Modulation of dermal epidermal junction protein expression.

HS8

The present invention relates to a class of heparan sulphate molecule called HS8. HS8 molecules are obtainable by methods of enriching mixtures of compounds containing one or more GAGs that bind to a polypeptide corresponding to a heparin-binding domain of FGF2. In particular, HS8 molecules can be obtained by enriching for heparan sulphate that binds to a heparin binding domain of FGF2 which domain comprises, or consists of, the amino acid sequence YCKNGGF. The enrichment process may be used to isolate HS8.

The present invention also relates to mixtures of compounds enriched with HS8, and methods of using such mixtures.

In addition to being obtainable by the methodology described here, HS8 can also be defined functionally and structurally.

Functionally, an HS8 is capable of binding a peptide having, or consisting of, the amino acid sequence of YCKNGGF (SEQ ID NO:2). The peptide may contain one or more additional amino acids on one or both ends of the peptide. By way of example, the peptide may be GHFKDPKRLYCKNGGF (SEQ ID NO:1).

Preferably, HS8 binds the peptide with a $K_D$ of less than 100 µM, more preferably less than one of 50 µM, 40 µM, 30 µM, 20 µM, or 10 µM.

Preferably, HS8 also binds FGF2 protein with a $K_D$ of less than 100 µM, more preferably less than one of 50 µM, 40 µM, 30 µM, 20 µM, or 10 µM. Binding between HS8 and FGF2 protein may be determined by the following assay method.

FGF2 is dissolved in Blocking Solution (0.2% gelatin in SAB) at a concentration of 3 µg/ml and a dilution series from 0-3 µg/ml in Blocking Solution is established. Dispensing of 200 µl of each dilution of FGF2 into triplicate wells of Heparin/GAG Binding Plates pre-coated with heparin; incubated for 2 hrs at 37° C., washed carefully three times with SAB and 200 µl of 250 ng/ml biotinylated anti-FGF2 added in Blocking Solution. Incubation for one hour at 37° C., wash carefully three times with SAB, 200 µl of 220 ng/ml ExtrAvidin-AP added in Blocking Solution, Incubation for 30 mins at 37° C., careful washing three times with SAB and tap to remove residual liquid, 200 µl of Development Reagent (SigmaFAST p-Nitrophenyl phosphate) added. Incubate at room temperature for 40 minutes with absorbance reading at 405 nm within one hour.

In this assay, binding may be determined by measuring absorbance and may be determined relative to controls such as FGF2 protein in the absence of added heparan sulphate, or FGF2 protein to which an heparan sulphate is added that does not bind FGF2 protein.

The binding of HS8 is preferably specific, in contrast to non-specific binding and in the context that the HS8 can be selected from other heparan sulphates and/or GAGs by a method involving selection of heparan sulphates exhibiting a high affinity binding interaction with the peptide comprising YCKNGGF such as SEQ ID NO:1, or with FGF2 protein.

HS8 according to the present invention preferably enhances dermal fibroblast proliferation in 10% FCS medium, down-regulates keratinocyte differentiation markers K10, transglutaminase-1 and involucrin, and enhances the number of motile and hypermotile keratinocytes.

The disaccharide composition of HS8 following digestion with heparin lyases I, II and III to completion and then subjecting the resulting disaccharide fragments to capillary electrophoresis analysis is shown in FIGS. 26 and 27.

HS8 according to the present invention includes heparan sulphate that has a disaccharide composition within ±10% (more preferably ±one of 9%, 8%, 7%, 6%, 5%, 4%, 3%, 2%, 1% or 0.5%) of the normalised percentage values shown for each disaccharide in FIG. 27 for the HS8 retained species or in FIG. 26 for the HS8 retained species, as determined by digestion with heparin lyases I, II and III to completion and then subjecting the resulting disaccharide fragments to capillary electrophoresis analysis.

The disaccharide composition of HS8 as determined by digestion with heparin lyases I, II and III to completion and then subjecting the resulting disaccharide fragments to capillary electrophoresis analysis may have a disaccharide composition according to any one of the following:

| Disaccharide | Normalised weight percentage |
|---|---|
| ΔUA,2S-GlcNS,6S | 12.7 ± 3.0 |
| ΔUA,2S-GlcNS | 7.2 ± 2.0 |
| ΔUA-GlcNS,6S | 15.5 ± 3.0 |
| ΔUA,2S-GlcNAc,6S | 6.5 ± 2.0 |
| ΔUA-GlcNS | 15.7 ± 3.0 |
| ΔUA,2S-GlcNAc | 1.0 ± 0.5 |
| ΔUA-GlcNAc,6S | 8.9 ± 3.0 |
| ΔUA-GlcNAc | 32.5 ± 3.0 |
| or | |
| ΔUA,2S-GlcNS,6S | 12.7 ± 2.0 |
| ΔUA,2S-GlcNS | 7.2 ± 2.0 |
| ΔUA-GlcNS,6S | 15.5 ± 2.0 |
| ΔUA,2S-GlcNAc,6S | 6.5 ± 2.0 |
| ΔUA-GlcNS | 15.7 ± 2.0 |
| ΔUA,2S-GlcNAc | 1.0 ± 0.5 |
| ΔUA-GlcNAc,6S | 8.9 ± 2.0 |
| ΔUA-GlcNAc | 32.5 ± 2.0 |
| or | |
| ΔUA,2S-GlcNS,6S | 12.7 ± 2.0 |
| ΔUA,2S-GlcNS | 7.2 ± 1.0 |
| ΔUA-GlcNS,6S | 15.5 ± 2.0 |
| ΔUA,2S-GlcNAc,6S | 6.5 ± 1.0 |
| ΔUA-GlcNS | 15.7 ± 2.0 |
| ΔUA,2S-GlcNAc | 1.0 ± 0.5 |
| ΔUA-GlcNAc,6S | 8.9 ± 2.0 |
| ΔUA-GlcNAc | 32.5 ± 3.0 |
| or | |
| ΔUA,2S-GlcNS,6S | 12.7 ± 1.0 |
| ΔUA,2S-GlcNS | 7.2 ± 0.4 |
| ΔUA-GlcNS,6S | 15.5 ± 1.0 |
| ΔUA,2S-GlcNAc,6S | 6.5 ± 0.6 |
| ΔUA-GlcNS | 15.7 ± 3.0 |
| ΔUA,2S-GlcNAc | 1.0 ± 0.4 |
| ΔUA-GlcNAc,6S | 8.9 ± 1.0 |
| ΔUA-GlcNAc | 32.5 ± 1.6 |
| or | |
| ΔUA,2S-GlcNS,6S | 12.7 ± 0.75 |
| ΔUA,2S-GlcNS | 7.2 ± 0.3 |
| ΔUA-GlcNS,6S | 15.5 ± 0.75 |
| ΔUA,2S-GlcNAc,6S | 6.5 ± 0.45 |
| ΔUA-GlcNS | 15.7 ± 2.25 |
| ΔUA,2S-GlcNAc | 1.0 ± 0.3 |
| ΔUA-GlcNAc,6S | 8.9 ± 0.75 |
| ΔUA-GlcNAc | 32.5 ± 1.2 |
| or | |
| ΔUA,2S-GlcNS,6S | 12.7 ± 0.5 |
| ΔUA,2S-GlcNS | 7.2 ± 0.2 |
| ΔUA-GlcNS,6S | 15.5 ± 0.5 |
| ΔUA,2SGlcNAc,6S | 6.5 ± 0.3 |
| ΔUA-GlcNS | 15.7 ± 1.5 |
| ΔUA,2S-GlcNAc | 1.0 ± 0.2 |
| ΔUA-GlcNAc,6S | 8.9 ± 0.5 |
| ΔUA-GlcNAc | 32.5 ± 0.8 |

In preferred embodiments the total weight percentage of the 8 disaccharides listed is 100% (optionally ±3.0% or less, or ±2.0% or less, ±1.0% or less, ±0.5% or less).

Comparison of HS8 with an HS isolated as having high affinity for the growth factor BMP2, called HS3 (described in WO2010/030244) reveals that the structural dissimilarity of HS8 compared to HS3 is characterised by the amount of the following disaccharides: ΔUA-GlcNS,6S and ΔUA-GlcNS. In particular HS8 has a greater percentage composition of ΔUA-GlcNS,6S than HS3 and a lower percentage composition of ΔUA-GlcNS than HS3.

As such, HS8 may be characterised by having a percentage composition of ΔUA-GlcNS,6S of 15.5±4.0 or less, or ±3.5 or less, or ±3.0 or less, or ±2.5 or less, or ±2.0 or less, ±1.5 or less, or ±1.0 or less, or ±0.5 or less, or ±0.2S or less, or ±0.1 or less. HS8 may additionally or alternatively be characterised by having a percentage composition of ΔUA-GlcNS of 15.7±4.0 or less, or ±3.5 or less, or ±3.0 or less, or ±2.5 or less, or ±2.0 or less, or ±1.5 or less, or ±1.0 or less, or ±0.5 or less, or ±0.25 or less, or ±0.1 or less.

HS8 may also be characterised by having a percentage composition of ΔUA,2S-GlcNS,6S of 12.7±1.5 or less, ±1.0 or less, or ±0.5 or less, or ±0.25 or less, or ±0.1 or less.

HS8 may also be characterised by having a percentage composition of ΔUA,2S-GlcNS of 7.2 or ±2.0 or less, ±1.5 or less, ±1.0 or less, or ±0.5 or less, or ±0.25 or less, or ±0.1 or less.

HS8 may also be characterised by having a percentage composition of ΔUA,2S-GlcNAc,6S of 6.5±1.5 or less, ±1.0 or less, or ±0.5 or less, or ±0.25 or less, or ±0.1 or less.

HS8 may also be characterised by having a percentage composition of ΔUA-GlcNAc,6S of 8.9±0.5 or less, or ±0.25 or less, or ±0.1 or less.

In these embodiments the percentage composition of the remaining disaccharide components may be as listed above, or as shown in FIG. 26 or 27 ±one of 10%, 9%, 8%, 7%, 6%, 5%, 4%, 3%, 2%, 1% or 0.5%.

Digestion of HS8 with heparin lyases I, II and III and/or capillary electrophoresis analysis of disaccharides is preferably performed in accordance with Example 9.

Digestion of HS preparations with heparin lyase enzymes may be conducted as follows: HS preparations (1 mg) are each dissolved in 500 μL of sodium acetate buffer (100 mM containing 10 mM calcium acetate, pH 7.0) and 2.5 mU each of the three enzymes is added; the samples are incubated at 37° C. overnight (24 h) with gentle inversion (9 rpm) of the sample tubes; a further 2.5 mU each of the three enzymes is added to the samples which are incubated at 37° C. for a further 48 h with gentle inversion (9 rpm) of the sample tubes; digests are halted by heating (100° C., 5 min) and are then lyophilized; digests are resuspended in 500 μL water and an aliquot (50 μL) is taken for analysis.

Capillary electrophoresis (CE) of disaccharides from digestion of HS preparations may be conducted as follows: capillary electrophoresis operating buffer is made by adding an aqueous solution of 20 mM $H_3PO_4$ to a solution of 20 mM $Na_2HPO_4 \cdot 12H_2O$ to give pH 3.5; column wash is 100 mM NaOH (diluted from 50% w/w NaOH); operating buffer and column wash are both filtered using a filter unit fitted with 0.2 μm cellulose acetate membrane filters; stock solutions of disaccharide Is (e.g. 12) are prepared by dissolving the disaccharides in water (1 mg/mL); calibration curves for the standards are determined by preparing a mix containing all standards containing 10 μg/100 μL of each disaccharide and a dilution series containing 10, 5, 2.5, 1.25, 0.625, 0.3125 μg/100 μL is prepared; including 2.5 μg of internal standard (ΔUA,2S-GlcNCOEL6S). The digests of HS are diluted (50 μL/mL) with water and the same internal standard is added (2.5 μg) to each sample. The solutions are freeze-dried and re-suspended in water (1 mL). The samples are filtered using PTFE hydrophilic disposable syringe filter units.

Analyses are performed using a capillary electrophoresis instrument on an uncoated fused silica capillary tube at 25° C. using 20 mM operating buffer with a capillary voltage of 30 kV. The samples are introduced to the capillary tube using hydrodynamic injection at the cathodic (reverse polarity) end. Before each run, the capillary is flushed with 100 mM NaOH (2 min), with water (2 min) and pre-conditioned with operating buffer (5 min). A buffer replenishment system replaces the buffer in the inlet and outlet tubes to ensure consistent volumes, pH and ionic strength are maintained. Water only blanks are run at both the beginning, middle and end of the sample sequence. Absorbance is monitored at 232 nm. All data is stored in a database and is subsequently retrieved and re-processed. Duplicate or triplicate digests/analyses may be performed and the normalized percentage of the disaccharides in the HS digest is calculated as the mean average of the results for the analyses.

In some embodiments HS8 has an average (mean) molecular weight in the range 18 to 27 kDa. In some embodiments this may be one of 20 to 25 kDa, 21 to 25 kDa, 21 to 24 kDa, 21 to 23 kDa, 20 to 24 kDa, 20 to 23 kDa, or 20 to 22 kDa.

In some embodiments an HS8 chain comprises at least 25 disaccharide units. In some embodiments this may be one of at least 26 disaccharides, at least 27 disaccharides, at least 28 disaccharides, at least 29 disaccharides, at least 30 disaccharides, at least 31 disaccharides, at least 32 disaccharides, at least 33 disaccharides, at least 34 disaccharides, at least 35 disaccharides, at least 36 disaccharides, at least 37 disaccharides, at least 38 disaccharides, at least 39 disaccharides, at least 40 disaccharides, at least 41 disaccharides, at least 42 disaccharides, at least 43 disaccharides, or at least 44 disaccharides.

To identify HS8 the inventors used a method that involves enriching for glycosaminoglycan molecules that exhibit binding to particular polypeptides having a heparin-binding domain. Isolated GAG mixtures and/or molecules can then be identified and tested for their ability to modulate the growth and differentiation of cells and tissue expressing a protein containing the heparin-binding domain. This enables the controlled analysis of the effect of particular GAG saccharide sequences on the growth and differentiation of cells and tissue, both in vitro and in vivo. This methodology is described in PCT/GB2009/000469 (WO2010/030244), incorporated herein by reference. The inventors applied this methodology to Fibroblast Growth Factor 2 (FGF2) in order to isolate and characterise GAGs having high binding to FGF2

Accordingly, to identify HS8 the inventors provided a method of isolating glycosaminoglycans capable of binding to proteins having heparin/heparan-binding domains, the method comprising:
(i) providing a solid support having polypeptide molecules adhered to the support, wherein the polypeptide comprises a heparin-binding domain;
(ii) contacting the polypeptide molecules with a mixture comprising glycosaminoglycans such that polypeptide-glycosaminoglycan complexes are allowed to form;
(iii) partitioning polypeptide-glycosaminoglycan complexes from the remainder of the mixture;
(iv) dissociating glycosaminoglycans from the polypeptide-glycosaminoglycan complexes;
(v) collecting the dissociated glycosaminoglycans.

The inventors also provided isolated glycosaminoglycans identified by their ability to modulate the growth or differentiation of cells or tissues. To do this, they provided a method of identifying glycosaminoglycans capable of stimulating or inhibiting the growth and/or differentiation of cells and/or tissues, the method comprising:
(i) providing a solid support having polypeptide molecules adhered to the support, wherein the polypeptide comprises a heparin-binding domain;
(ii) contacting the polypeptide molecules with a mixture comprising glycosaminoglycans such that polypeptide-glycosaminoglycan complexes are allowed to form;
(iii) partitioning polypeptide-glycosaminoglycan complexes from the remainder of the mixture;
(iv) dissociating glycosaminoglycans from the polypeptide-glycosaminoglycan complexes;
(v) collecting the dissociated glycosaminoglycans;
(vi) adding the collected glycosaminoglycans to cells or tissues in which a protein containing the amino acid sequence of the heparin-binding domain is present;
(vii) measuring one or more of: proliferation of the cells, differentiation of the cells, expression of one or more protein markers.

The inventors used these methods to identify a GAG capable of binding to FGF2 (which they called HS8), wherein the polypeptide used in the inventors' methodology comprised the heparin-binding domain of GHFKDPKRLY-CKNGGF (SEQ ID NO:1).

In the inventors' methodology, the mixture comprising GAGs may contain synthetic glycosaminoglycans. However, GAGs obtained from cells or tissues are preferred. For example, the mixture may contain extracellular matrix wherein the extracellular matrix material is obtained by scraping live tissue in situ (i.e. directly from the tissue in the body of the human or animal from which it is obtained) or by scraping tissue (live or dead) that has been extracted from the body of the human or animal. Alternatively, the extracellular matrix material may be obtained from cells grown in culture. The extracellular matrix material may be obtained from connective tissue or connective tissue cells, e.g. bone, cartilage, muscle, fat, ligament or tendon. In one embodiment commercially available heparan sulphate from Porcine Mucosa (Celsus HS) was used.

The GAG component may be extracted from a tissue or cell sample or extract by a series of routine separation steps (e.g. anion exchange chromatography), well known to those of skill in the art.

GAG mixtures may contain a mixture of different types of glycosaminoglycan, which may include dextran sulphates, chondroitin sulphates and heparan sulphates. Preferably, the GAG mixture contacted with the solid support is enriched for heparan sulphate. A heparan sulphate-enriched GAG fraction may be obtained by performing column chromatography on the GAG mixture, e.g. weak, medium or strong anion exchange chromatography, as well as strong high pressure liquid chromatography (SAX-HPLC), with selection of the appropriate fraction.

The collected GAGs may be subjected to further analysis in order to identify the GAG, e.g. determine GAG composition or sequence, or determine structural characteristics of the GAG. GAG structure is typically highly complex, and, taking account of currently available analytical techniques, exact determinations of GAG sequence structure are not possible in most cases.

However, the collected GAG molecules may be subjected to partial or complete saccharide digestion (e.g. chemically by nitrous acid or enzymatically with lyases such as heparinase III) to yield saccharide fragments that are both characteristic and diagnostic of the GAG. In particular, digestion to yield disaccharides (or tetrasaccharides) may be used to measure the percentage of each disaccharide obtained which will provide a characteristic disaccharide "fingerprint" of the GAG.

The pattern of sulphation of the GAG can also be determined and used to determine GAG structure. For example, for heparan sulphate the pattern of sulphation at amino sugars and at the C2, C3 and C6 positions may be used to characterise the heparan sulphate.

Disaccharide analysis, tetrasaccharide analysis and analysis of sulphation can be used in conjunction with other analytical techniques such as HPLC, mass spectrometry and NMR which can each provide unique spectra for the GAG. In combination, these techniques may provide a definitive structural characterisation of the GAG.

For example, the $1^H$ NMR spectra of HS8, in comparison with Celsus HS (from which HS8 was derived) and HS3 (a BMP2 binding HS) is shown in FIGS. 15 and 16. HS8 according to the present invention may have a $1^H$ NMR spectra corresponding to the HS8 spectra of FIG. 15 or 16. In some embodiments HS8 according to the present invention may have a $1^H$ NMR spectra in which the spectra at 4.0-3.5 ppm corresponds to that of HS8 in FIG. 16 (top line between 3.8-3.7 ppm). In some embodiments HS8 according to the present invention may have a peak at about 3.8 ppm and/or a peak at about 3.7 ppm. In some embodiments HS8 can be distinguished from other HS8 by its unique methine and/or methylene $1^H$ NMR spectra, e.g. as shown in FIG. 16.

A high affinity binding interaction between the GAG and heparin-binding domain indicates that the GAG will contain a specific saccharide sequence that contributes to the high affinity binding interaction. A further step may comprise determination of the complete or partial saccharide sequence of the GAG, or the key portion of the GAG, involved in the binding interaction.

GAG-polypeptide complexes may be subjected to treatment with an agent that lyses glycosaminoglycan chains, e.g. a lyase. Lyase treatment may cleave portions of the bound GAG that are not taking part in the binding interaction with the polypeptide.

Portions of the GAG that are taking part in the binding interaction with the polypeptide may be protected from lyase action. After removal of the lyase, e.g. following a washing step, the GAG molecule that remains bound to the polypeptide represents the specific binding partner ("GAG ligand") of the polypeptide. Owing to the lower complexity of shorter GAG molecules, following dissociation and collection of the GAG ligand, a higher degree of structural characterisation of the GAG ligand can be expected. For example, the combination of any of the saccharide sequence (i.e. the primary (linear) sequence of monosaccharides contained in the GAG ligand), sulphation pattern, disaccharide and/or tetrasaccharide digestion analysis, NMR spectra, mass spectrometry spectra and HPLC spectra may provide a high level of structural characterisation of the GAG ligand.

As used herein, the terms 'enriching', 'enrichment', 'enriched', etc. describes a process (or state) whereby the relative composition of a mixture is (or has been) altered in such a way that the fraction of that mixture given by one or more of those entities is increased, while the fraction of that mixture given by one or more different entities is decreased. GAGs isolated by enrichment may be pure, i.e. contain substantially only one type of GAG, or may continue to be a mixture of different types of GAG, the mixture having a higher proportion of particular GAGs that bind to the heparin-binding domain relative to the starting mixture.

The GAGs identified preferably exhibit a functional effect when contacted with cells or tissue in which a protein containing the heparin-binding domain is expressed or contained. The functional effect may be a modulating or potentiating effect. The functional effect may be to promote (stimulate) or inhibit the proliferation of the cells of a certain type or the differentiation of one cell type into another, or the expression of one or more protein markers.

As used herein, the term 'modulating effect' is understood to mean the effect that a first entity has on a second entity wherein the second entity's normal function in another process or processes is modified by the presence of the first entity. The modulating effect may be either agonistic or antagonistic.

The modulating effect may be a potentiating effect. The term 'potentiating effect' is understood to mean the effect of increasing potency. In a preferred embodiment of the present invention, the term 'potentiating effect' refers to the effect that a first entity has on a second entity, which effect increases the potency of that second entity in another process or processes. In a further preferred embodiment of the present invention, the potentiating effect is understood to mean the effect of isolated GAGs on a heparin-binding factor, wherein the said effect increases the potency of said heparin-binding factor.

As used herein, the process of 'contacting' involves the bringing into close physical proximity of two or more discrete entities. The process of 'contacting' involves the bringing into close proximity of two or more discrete entities for a time, and under conditions, sufficient to allow a portion of those two or more discrete entities to interact on a molecular level. Preferably, as used herein, the process of 'contacting' involves the bringing into close proximity of the mixture of compounds possessing one or more GAGs and the polypeptide corresponding to the heparin-binding domain of a heparin-binding factor. Examples of 'contacting' processes include mixing, dissolving, swelling, washing. In preferred embodiments 'contact' of the GAG mixture and polypeptide is sufficient for complexes, which may be covalent but are preferably non-covalent, to form between GAGs and polypeptides that exhibit high affinity for each other.

The polypeptide may comprise the full length or near full length primary amino acid sequence of a selected protein having a heparin-binding domain. Due to folding that may occur in longer polypeptides leading to possible masking of the heparin-binding domain from the GAG mixture, it is preferred for the polypeptide to be short. Preferably, the polypeptide will have an amino acid sequence that includes the heparin-binding domain and optionally including one or more amino acids at one or each of the N- and C-terminals of the peptides. These additional amino acids may enable the addition of linker or attachment molecules to the polypeptide that are required to attach the polypeptide to the solid support.

In preferred embodiments of the inventors' methodology, in addition to the number of amino acids in the heparin-binding domain the polypeptide contains 1-20, more preferably 1-10, still more preferably 1-5 additional amino acids. In some embodiments the amino acid sequence of the heparin-binding domain accounts for at least 80% of the amino acids of the polypeptide, more preferably at least 90%, still more preferably at least 95%. In order to adhere polypeptides to the surface of a solid support the polypeptides are preferably modified to include a molecular tag, and the surface of the solid support is modified to incorporate a corresponding molecular probe having high affinity for the molecular tag, i.e. the molecular tag and probe form a binding pair. The tag and/or probe may be chosen from any one of: an antibody, a cell receptor, a ligand, biotin, any fragment or derivative of these structures, any combination of the foregoing, or any other structure with which a probe can be designed or configured to bind or otherwise associate with specificity. A preferred binding pair suitable for use as tag and probe is biotin and avidin.

The polypeptide is derived from the protein of interest, which in the present case is FGF2. By "derived from" is meant that the polypeptide is chosen, selected or prepared because it contains the amino acid sequence of a heparin-binding domain that is present in the protein of interest. The amino acid sequence of the heparin-binding domain may be modified from that appearing in the protein of interest, e.g. to investigate the effect of changes in the heparin-binding domain sequence on GAG binding.

In this specification the protein is FGF2. The amino acid sequences of the preferred heparin-binding domains is GHFKDPKRLYCKNGGF (SEQ ID NO:1) [which is found at amino acids 157-172 of human FGF2], or a sequence having the sequence YCKNGGF (SEQ ID NO:2).

It is understood by those skilled in the art that small variations in the amino acid sequence of a particular polypeptide may allow the inherent functionality of that portion to be maintained. It is also understood that the substitution of certain amino acid residues within a peptide with other amino acid residues that are isosteric and/or isoelectronic may either maintain or improve certain properties of the unsubstituted peptide. These variations are also encompassed within the scope of the present invention. For example, the amino acid alanine may sometimes be substituted for the amino acid glycine (and vice versa) whilst maintaining one or more of the properties of the peptide. The term 'isosteric' refers to a spatial similarity between two entities. Two examples of moieties that are isosteric at moderately elevated temperatures are the iso-propyl and tert-butyl groups. The term 'isoelectronic' refers to an electronic similarity between two entities, an example being the case where two entities possess a functionality of the same, or similar, pKa.

The polypeptide corresponding to the heparin-binding domain may be synthetic or recombinant.

The solid support may be any substrate having a surface to which molecules may be attached, directly or indirectly, through either covalent or non-covalent bonds. The solid support may include any substrate material that is capable of providing physical support for the probes that are attached to the surface. It may be a matrix support. The material is generally capable of enduring conditions related to the attachment of the probes to the surface and any subsequent treatment, handling, or processing encountered during the performance of an assay. The materials may be naturally occurring, synthetic, or a modification of a naturally occurring material. The solid support may be a plastics material (including polymers such as, e.g., poly(vinyl chloride), cyclo-olefin copolymers, polyacrylamide, polyacrylate, polyethylene, polypropylene, poly(4-methylbutene), polystyrene, polymethacrylate, poly(ethylene terephthalate), polytetrafluoroethylene (PTFE or Teflon®), nylon, poly(vinyl butyrate)), etc., either used by themselves or in conjunction with other materials. Additional rigid materials may be considered, such as glass, which includes silica and further includes, for example, glass that is available as Bioglass. Other materials that may be employed include porous materials, such as, for example, controlled pore glass beads. Any other materials known in the art that are capable of having one or more functional groups, such as any of an amino, carboxyl, thiol, or hydroxyl functional group, for example, incorporated on its surface, are also contemplated.

Preferred solid supports include columns having a polypeptide immobilized on a surface of the column. The surface may be a wall of the column, and/or may be provided by beads packed into the central space of the column.

The polypeptide may be immobilised on the solid support. Examples of methods of immobilisation include: adsorption, covalent binding, entrapment and membrane confinement. In a preferred embodiment of the present invention the interaction between the polypeptide and the matrix is substantially permanent. In a further preferred embodiment of the present invention, the interaction between the peptide and the matrix is suitably inert to ion-exchange chromatography. In a preferred arrangement, the polypeptide is attached to the surface of the solid support. It is understood that a person skilled in the art would have a large array of options to choose from to chemically and/or physically attach two entities to each other. These options are all encompassed within the scope of the present invention. In a preferred arrangement, the polypeptide is adsorbed to a solid support through the interaction of biotin with streptavidin. In a representative example of this arrangement, a molecule of biotin is bonded covalently to the polypeptide, whereupon the biotin-polypeptide conjugate binds to streptavidin, which in turn has been covalently bonded to a solid support. In another arrangement, a spacer or linker moiety may be used to connect the molecule of biotin with the polypeptide, and/or the streptavidin with the matrix.

By contacting the GAG mixture with the solid support GAG-polypeptide complexes are allowed to form. These are partitioned from the remainder of the mixture by removing the remainder of the mixture from the solid support, e.g. by washing the solid support to elute non-bound materials. Where a column is used as the solid support non-binding components of the GAG mixture can be eluted from the column leaving the GAG-polypeptide complexes bound to the column.

It is understood that certain oligosaccharides may interact in a non-specific manner with the polypeptide. In certain embodiments, oligosaccharide which interacts with the polypeptide in a non-specific manner may be included in, or excluded from the mixture of compounds enriched with one or more GAGs that modulate the effect of a heparin-binding factor. An example of a non-specific interaction is the temporary confinement within a pocket of a suitably sized and/or shaped molecule. Further it is understood that these oligosaccharides may elute more slowly than those oligosaccharides that display no interaction with the peptide at all. Furthermore it is understood that the compounds that bind non-specifically may not require the input of the same external stimulus to make them elute as for those compounds that bind in a specific manner (for example through an ionic interaction). The inventors' methodology is capable of separating a mixture of oligosaccharides into those components of that mixture that: bind in a specific manner to the polypeptide; those that bind in a non-specific manner to the polypeptide; and those that do not bind to the polypeptide. These designations are defined operationally for each GAG-peptide pair.

By varying the conditions (e.g. salt concentration) present at the surface of the solid support where binding of the GAG and polypeptide occurs those GAGs having the highest affinity and/or specificity for the heparin-binding domain can be selected. GAGs may accordingly be obtained that have a high binding affinity for a protein of interest and/or the heparin-binding domain of the protein of interest. The binding affinity ($K_d$) may be chosen from one of: less than 10 µM, less than 1 µM, less than 100 nM, less than 10 nM, less than 1 nM, less than 100 µM.

GAGs obtained by the methods described may be useful in a range of applications, in vitro and/or in vivo. The GAGs may be provided for use in stimulation or inhibition of cell or tissue growth and/or proliferation and/or differentiation either in cell or tissue culture in vitro, or in cells or tissue in vivo.

The GAGs may be provided as a formulation for such purposes.

In another embodiment the HS8 may be formulated for use in a method of cosmetic treatment. A cosmetic composition may be provided comprising HS8 and a cosmetically acceptable diluent, carrier or adjuvant. Optionally, cosmetic compositions according to the present invention may also contain the protein of interest (i.e. FGF2) having the heparin-binding domain to which the GAG binds. In further embodiments the cosmetic compositions may further comprise stem cells, e.g. mesenchymal stem cells.

Cosmetic compositions according to the present invention may therefore comprise one of:

(a) HS8;
(b) HS8 in combination with a protein containing the heparin-binding domain bound by HS8 (e.g. SEQ ID NO:1);

The compounds of the enriched mixtures of the present invention can be administered to a subject as a cosmetically acceptable salt thereof. For example, base salts of the compounds of the enriched mixtures of the present invention include, but are not limited to, those formed with cosmetically acceptable cations, such as sodium, potassium, lithium, calcium, magnesium, ammonium and alkylammonium. The present invention includes within its scope cationic salts, for example the sodium or potassium salts.

It will be appreciated that the compounds of the enriched mixtures of the present invention which bear a carboxylic acid group may be delivered in the form of an administrable prodrug, wherein the acid moiety is esterified (to have the form —CO2R').

The term "pro-drug" specifically relates to the conversion of the —OR' group to a —OH group, or carboxylate anion therefrom, in vivo. Accordingly, the prodrugs of the present invention may act to enhance drug adsorption and/or drug delivery into cells. The in vivo conversion of the prodrug may be facilitated either by cellular enzymes such as lipases and esterases or by chemical cleavage such as in vivo ester hydrolysis.

Cosmetic compositions according to aspects of the present invention may be formulated for administration by a number of routes, preferably topically. The compositions may be formulated in fluid or solid form. Fluid formulations may be formulated for administration by injection to a selected region of the human or animal body.

Cosmetic Uses and Applications of HS8

The term keratin refers to a family of fibrous proteins which are important structural proteins forming the outer layer of human and mammalian skin. Keratin is also an important component of hair and nails. Keratin filaments are normally present in epithelial cells and are abundant in the cornified layer of the epidermis in cells that have undergone keratinization. By way of example, keratins 1, 2, 9 and 10 are usually present in the stratum corneum and in keratinocytes, keratins 3 and 13 are usually present in the cornea, keratins 4 and 13 or keratins 5, 14 and 15 are usually present in the stratified epithelium, keratins 6, 16 and 17 are usually present in the squamous epithelium, keratins 7 and 19 are usually present in the ductal epithelium and keratins 8, 18 and 20 are usually present in simple epithelium.

In the present application a preferred keratinous material is one that contains keratin or contains keratin-containing epithelial cells or stratum corneum. The keratinous material is preferably skin, e.g. of a human or mammal. In some embodiments a keratinous material may be hair or nail, e.g. of a human or mammal.

The compositions of the present invention are useful for regulating mammalian skin condition (especially human skin, more especially human facial skin), including visible and/or tactile discontinuities in skin, signs of skin aging, and visible and/or tactile discontinuities in skin associated with skin aging (including fine lines, wrinkles, large pores, surface roughness, dryness and other texture discontinuities associated with aged skin). Such regulation may optionally include prophylactic regulation.

Regulating skin condition involves topically applying to the skin a safe and effective amount of a composition of the present invention. The amount of the composition which is applied, the frequency of application and the period of use will vary widely depending upon the level of HS8 and/or other components of a given composition and the level of regulation desired, e.g., in light of the level of skin aging present in the subject and the rate of further skin aging.

In some embodiments the composition is chronically applied to the skin. By "chronic topical application" is meant continued application of the composition over an extended period during the subject's lifetime, e.g. for a period of one of at least about one week, at least about one month, at least about three months, at least about six months, or for at least about one year. While benefits are obtainable after various maximum periods of use (e.g., five, ten or twenty years), it may be preferred that chronic application continues throughout the subject's lifetime. Typically applications would be of the order of about once per day over such extended periods, however application rates can vary from about once per week up to about three times per day or more.

A wide range of quantities of the compositions of the present invention can be employed to provide a skin appearance and/or feel benefit. Quantities of the present compositions which are typically applied per application are, in mg composition/$cm^2$ skin, from about 0.1 mg/$cm^2$ to about 10 mg/$cm^2$. A particularly useful application amount is about 2 mg/$cm^2$.

Regulating skin condition is preferably practiced by applying a composition in the form of a skin lotion, cream, gel, emulsion, spray, conditioner, cosmetic, lipstick, foundation, nail polish, or the like which is intended to be left on the skin for some aesthetic, prophylactic, cosmetic or other benefit (i.e., a "leave-on" composition). After applying the composition to the skin, it is preferably left on the skin for a period of one of at least about 15 minutes, at least about 30 minutes, at least about 1 hour, at least several hours, e.g., up to about 12 hours. Any part of the external portion of the skin, hair, and/or nails can be treated, e.g., face, lips, under-eye area, eyelids, scalp, neck, torso, arms, hands, legs, fingernails, toenails, scalp hair, eyelashes, eyebrows, etc.

Another approach to ensure a continuous exposure of the skin to at least a minimum level of HS8 is to apply the compound by use of a patch applied, e.g., to the face. Such an approach is particularly useful for problem skin areas needing more intensive treatment. The patch can be occlusive, semi-occlusive or non-occlusive. The HS8 composition can be contained within the patch or be applied to the skin prior to application of the patch. The patch can also include additional actives such as chemical initiators for exothermic reactions such as those described in PCT application WO 9701313 to Burkett et al. The patch is preferably left on the skin for a period of at least about 15 minutes, at least about 30 minutes, at least about 1 hour, or at night as a form of night cosmetic treatment.

The compositions of the present invention are useful for regulating skin condition, e.g. through topical application, including visible and/or tactile discontinuities in skin (especially the skin surface; such discontinuities are generally undesired). Such discontinuities may be induced or caused by internal and/or external factors, and include the signs of skin aging described herein. "Regulating skin condition" includes prophylactically regulating skin condition, including visible and/or tactile discontinuities in skin such as, but not limited to, regulating visible and/or tactile discontinuities in the texture of skin, reducing post-inflammatory hyperpigmentation, regulating non-melanin discoloration of skin, regulating moisturization and barrier properties of skin, regulating epidermal differentiation of skin, regulating exfoliation of skin, thickening of skin to reduce skin atrophy, regulating the elasticity of skin, reducing oily skin, regulating cellulite in skin.

As used herein, prophylactically regulating skin condition includes delaying, minimizing and/or preventing visible and/or tactile discontinuities in skin. Regulating skin condition may involve improving skin appearance and/or feel.

The compositions of the present invention are useful for regulating signs of skin aging, more especially visible and/or tactile discontinuities in skin texture associated with aging.

"Regulating the signs of skin aging" optionally includes prophylactically regulating one or more of such signs (similarly, regulating a given sign of skin aging, e.g., lines, wrinkles or pores, optionally includes prophylactically regulating that sign). As used herein, prophylactically regulating such signs includes delaying, minimizing and/or preventing signs of skin aging.

"Signs of skin aging" include, but are not limited to, all outward visibly and tactilely perceptible manifestations as well as any other macro or micro effects due to skin aging. Such signs may be induced or caused by intrinsic factors or extrinsic factors, e.g., chronological aging and/or environmental damage (e.g., sunlight, UV, smoke, ozone, pollutants, stress, etc.). These signs may result from processes which include, but are not limited to, the development of textural discontinuities such as wrinkles, including both fine superficial wrinkles and coarse deep wrinkles, skin lines, facial frown lines, expression lines, photodamage, premature skin aging, crevices, bumps, pits, large pores, "orange peel" skin appearance, dryness, scaliness, flakiness and/or other forms of skin unevenness or roughness; excess skin oil such as over production of sebum, oiliness, facial shine, foundation breakthrough; excessive desquamation (or exfoliation) or epidermal differentiation such as scaliness, flakiness, keratoses, hyperkeratinization; inadequate skin moisturization (or hydration) such as caused by skin barrier damage, environmental dryness; loss of skin elasticity (loss and/or inactivation of functional skin elastin) such as elastosis, sagging (including puffiness in the eye area and jowls), loss of skin firmness, loss of skin tightness, loss of skin recoil from deformation; non-melanin skin discoloration such as undereye circles, blotching (e.g., uneven red coloration due to, e.g., rosacea), sallowness (pale color), discoloration caused by telangiectasia; melanin-related hyperpigmented (or unevenly pigmented) skin regions; post-inflammatory hyperpigmentation such as that which occurs following an inflammatory event (e.g., an acne lesion, in-grown hair, insect/spider bite or sting, scratch, cut, wound, abrasion, and the like); atrophy such as, but not limited to, that associated with aging; other histological or microscopic alterations in skin components such as ground substance (e.g., hyaluronic acid, glycosaminoglycans, etc.), collagen breakdown and structural alterations.

It is to be understood that the present invention is not to be limited to regulation of the above mentioned "signs of skin aging" which arise due to mechanisms associated with skin aging, but is intended to include regulation of said signs irrespective of the mechanism of origin. As used herein, "regulating skin condition" is intended to include regulation of such signs irrespective of the mechanism of origin.

The present invention is especially useful for preventing and/or reducing (minimizing) visible and/or tactile discontinuities in mammalian skin texture, including texture discontinuities associated with skin aging, to thereby provide improved skin appearance and/or feel, e.g., a smoother, more even appearance and/or feel. Such visible and/or tactile discontinuities in skin texture include crevices, bumps, pores, fine lines, wrinkles, scales, flakes and/or other forms of textural unevenness or roughness associated with skin aging. For example, the length, depth, and/or other dimension of lines and/or wrinkles are decreased, the apparent diameter of pores decreases, or the apparent height of tissue immediately proximate to pore openings approaches that of the interadnexal skin.

Compositions according to the present invention may comprise HS8, preferably in isolated or substantially purified form in combination with a carrier, which carrier preferably does not contain a heparan sulphate.

In some embodiments the carrier is a physiologically acceptable medium. In some embodiments the carrier is a cosmetically or dermatologically acceptable carrier.

According to the invention, the carrier is suitable for topical application to the skin, has good aesthetic properties, is compatible with the actives of the present invention and any other components, and will not cause any untoward safety or toxicity concerns A safe and effective amount of carrier may be selected from one of about 50% to about 99.99%, about 99.9% to about 80%, about 98% to about 90%, or about 95% to about 90% of the composition. In some embodiments a carrier is a member selected from the group consisting of oil-in-water, water-in-oil, water-in-oil-in-water, and oil-in-water-in-silicone emulsions.

The carrier can be in a wide variety of forms. For example, emulsion carriers, including, but not limited to, oil-in-water, water-in-oil, water-in-oil-in-water, and oil-in-water-in-silicone emulsions, may be useful herein. These emulsions can cover a broad range of viscosities, e.g, from about 100 cps to about 200,000 cps. These emulsions can also be delivered in the form of sprays using either mechanical pump containers or pressurized aerosol containers using conventional propellants. These carriers can also be delivered in the form of a mousse. Other suitable topical carriers include anhydrous liquid solvents such as oils, alcohols, and silicones (e.g., mineral oil, ethanol, isopropanol, dimethicone, cyclomethicone, and the like); aqueous-based single phase liquid solvents (e.g., hydro-alcoholic solvent systems); and thickened versions of these anhydrous and aqueous-based single phase solvents (e.g., where the viscosity of the solvent has been increased to form a solid or semi-solid by the addition of appropriate gums, resins, waxes, polymers, salts, and the like). Examples of topical carrier systems useful in the present invention are described in the following references all of which are incorporated herein by reference in their entirety: "Sun Products Formulary" Cosmetics & Toiletries, vol. 105, pp. 122-139 (December 1990); "Sun Products Formulary", Cosmetics & Toiletries, vol. 102, pp. 117-136 (March 1987); U.S. Pat. No. 4,960,764 to Figueroa et al., issued Oct. 2, 1990; and U.S. Pat. No. 4,254,105 to Fukuda et al., issued Mar. 3, 1981.

The carriers of the present invention can comprise from about 50% to about 99% of the weight of the compositions of the present invention, or from about 75% to about 99%, or from about 85% to about 95%. It may contain water and hydrophilic solvents.

Suitable cosmetically acceptable topical carriers include hydro-alcoholic systems and oil-in-water emulsions. When the carrier is a hydro-alcoholic system, the carrier can comprise from about 0% to about 99% of ethanol, isopropanol, or mixtures thereof, and from about 1% to about 99% of water. A carrier may comprise from about 5% to about 60% of ethanol, isopropanol, or mixtures thereof, and from about 40% to about 95% of water. A carrier may comprise from about 20% to about 50% of ethanol, isopropanol, or mixtures thereof, and from about 50% to about 80% of water. When the carrier is an oil-in-water emulsion, the carrier can include any of the common excipient ingredients for preparing these emulsions. A more detailed discussion of suitable carriers is found in U.S. Pat. No. 5,605,894 to Blank et al., and, U.S. Pat. No. 5,681,852 to Bissett, both of which are herein incorporated by reference in their entirety.

While it is possible for the active compound, HS8, to be administered alone, it is preferable to present it as a cosmetically suitable formulation (e.g., composition, preparation) comprising at least HS8, as defined herein, together with one or more other cosmetically acceptable ingredients well known to those skilled in the art, including, but not limited to, cosmetically acceptable carriers, excipients, diluents, fillers, buffers, preservatives, anti-oxidants, lubricants, stabilisers, solubilisers, surfactants (e.g., wetting agents), masking agents, colouring agents, flavouring agents, and sweetening agents. The formulation may further comprise other active agents, for example, other cosmetic or prophylactic agents.

Examples of additional skin actives include hydroxy acids, desquamatory agents, sunscreens, anti-oxidants, retinoids, moisturizing agents, and mixtures thereof. An hydroxy acid may be salicylic acid; a desquamatory agent may be selected from the group consisting of zwitterionic surfactants and mixtures thereof; a sun-block may be selected from the group consisting of zinc oxide, titanium dioxide and mixtures thereof; a sunscreen may be selected from the group consisting of 2-ethylhexyl-p-methoxycinnamate, 4,4'-t-butyl methoxydibenzoyl-methane, phenyl benzimidazole sulfonic acid, octocrylene and mixtures thereof; an anti-oxidant may be selected from the group consisting of tocopherol, esters thereof and mixtures thereof; a moisturizing agent may be selected from the group consisting of glycerol, urea, guanidine, petrolatum, panthenol, fatty acids esters of polyols and sugars, and mixtures thereof; and a retinoid may be selected from the group consisting of retinol, retinyl acetate, retinyl propionate, and mixtures thereof.

Thus, the present invention further provides cosmetic compositions, as defined above, and methods of making a cosmetic composition comprising admixing at least HS8, as defined herein, together with one or more other cosmetically acceptable ingredients well known to those skilled in the art, e.g., carriers, excipients, etc.

The term "cosmetically acceptable" as used herein pertains to compounds, ingredients, materials, compositions, dosage forms, etc., which are, within the scope of sound judgment of the skilled artisan, suitable for use in contact with the tissues of the subject in question (e.g., human) without excessive toxicity, irritation, allergic response, or other problem or complication, commensurate with a reasonable benefit/risk ratio. Each carrier, excipient, etc. must also be "acceptable" in the sense of being compatible with the other ingredients of the formulation.

The formulations may be prepared by any methods well known in the art. Such methods include the step of bringing into association the active compound with a carrier which constitutes one or more accessory ingredients. In general, the formulations are prepared by uniformly and intimately bringing into association the active compound with carriers (e.g., liquid carriers, finely divided solid carrier, etc.), and then shaping the product, if necessary.

Formulations may suitably be in the form of liquids, solutions (e.g., aqueous, non-aqueous), suspensions (e.g., aqueous, non-aqueous), emulsions (e.g., oil-in-water, water-in-oil), drops, tablets (including, e.g., coated tablets), granules, powders, pastilles, capsules (including, e.g., hard and soft gelatin capsules), cachets, pills, gels, pastes, ointments, creams, lotions (e.g. skin lotions, sunscreens), conditioners, cosmetics, lipsticks, foundations, nail polish, oils, foams, sprays, mists, or aerosols.

Formulations may suitably be provided as a patch, adhesive plaster, bandage, dressing, or the like which is coated or impregnated with HS8 and optionally one or more other cosmetically acceptable ingredients, including, for example, penetration, permeation, and absorption enhancers. Formulations may also suitably be provided in the form of a depot or reservoir.

The active compound may be dissolved in, suspended in, or admixed with one or more other cosmetically acceptable ingredients. The active compound may be presented in a liposome or other microparticulate which is designed to target the active compound.

Formulations suitable for topical or transdermal administration may include gels, sprays, pastes, ointments, creams, lotions (e.g. skin lotions, sunscreens), conditioners, cosmetics, lipsticks, foundations, nail polish, salves, oils, aqueous solutions, suspensions, emulsions and dispersions as well as patches, adhesive plasters, bandages, dressings, depots, and reservoirs. The term "topical application", as used herein, includes application or spread the compositions of the present invention onto the surface of the skin, hair or nails.

Ointments are typically prepared from the active compound and a paraffinic or a water-miscible ointment base.

Creams are typically prepared from the active compound and an oil-in-water or water-in-oil cream base. If desired, the aqueous phase of the cream base may include, for example, at least about 30% w/w of a polyhydric alcohol, i.e., an alcohol having two or more hydroxyl groups such as propylene glycol, butane-1,3-diol, mannitol, sorbitol, glycerol and polyethylene glycol and mixtures thereof.

Topical formulations may desirably include a compound which enhances absorption or penetration of the active compound through the skin or other affected areas. Examples of such dermal penetration enhancers include dimethylsulfoxide and related analogues.

Emulsions are typically prepared from the active compound and an oily phase, which may optionally comprise merely an emulsifier (otherwise known as an emulgent), or it may comprises a mixture of at least one emulsifier with a fat or an oil or with both a fat and an oil. Preferably, a hydrophilic emulsifier is included together with a lipophilic emulsifier which acts as a stabiliser. It is also preferred to include both an oil and a fat. Together, the emulsifier(s) with or without stabiliser(s) make up the so-called emulsifying wax, and the wax together with the oil and/or fat make up the so-called emulsifying ointment base which forms the oily dispersed phase of the cream formulations.

Suitable emulgents and emulsion stabilisers include Tween 60, Span 80, cetostearyl alcohol, myristyl alcohol, glyceryl monostearate and sodium lauryl sulphate. The choice of suitable oils or fats for the formulation is based on achieving the desired cosmetic properties, since the solubility of the active compound in most oils likely to be used in pharmaceutical emulsion formulations may be very low. Thus the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils can be used.

HS8 could be applied to a number of cosmetic applications in skin care that include coating technology for dressings, patches, plasters and the like. As such, formulations may suitably be provided as a patch, adhesive plaster, bandage, dressing, a biomaterial or the like which is impregnated with, or coated with, HS8 and optionally one or more other cosmetically acceptable ingredients, including, for example, penetration, permeation, and absorption enhancers.

Cosmetic compositions, and other formulations comprising HS8 may also comprise FGF2. Owing to the ability of HS8 to bind FGF2, the HS8 may act as a carrier of FGF2 assisting in delivery of FGF2 to the wound site.

Application or administration is preferably in a "cosmetically effective amount". The term "cosmetically effective amount" as used herein means an amount of a compound or composition sufficient to significantly induce a positive benefit, preferably a positive skin appearance or feel benefit, including independently the benefits disclosed herein, but low enough to avoid serious side effects, i.e., to provide a reasonable benefit to risk ratio, within the scope of sound judgment of the skilled artisan. A "cosmetically effective amount" pertains to the administration of compounds, ingredients, materials, compositions, dosage forms, etc. in an amount effective to induce a cosmetic benefit. This is within the scope of sound judgement of a relevant practitioner. It will be appreciated by one of skill in the art that appropriate dosages of the active compounds, and compositions comprising the active compounds, can vary from subject to subject.

Glycosaminglycans

As used herein, the terms 'glycosaminoglycan' and 'GAG' are used interchangeably and are understood to refer to the large collection of molecules comprising an oligosaccharide, wherein one or more of those conjoined saccharides possess an amino substituent, or a derivative thereof. Examples of GAGs are chondroitin sulfate, keratan sulfate, heparin, dermatan sulfate, hyaluronate and heparan sulfate.

As used herein, the term 'GAG' also extends to encompass those molecules that are GAG conjugates. An example of a GAG conjugate is a proteoglycosaminoglycan (PGAG, proteoglycan) wherein a peptide component is covalently bound to an oligosaccharide component.

Heparan Sulphate (HS)

Heparan sulfate proteoglycans (HSPGs) represent a highly diverse subgroup of proteoglycans and are composed of heparan sulfate glycosaminoglycan side chains covalently attached to a protein backbone. The core protein exists in three major forms: a secreted form known as perlecan, a form anchored in the plasma membrane known as glypican, and a transmembrane form known as syndecan. They are ubiquitous constituents of mammalian cell surfaces and most extracellular matrices. There are other proteins such as agrin, or the amyloid precursor protein, in which an HS chain may be attached to less commonly found cores.

"Heparan Sulphate" ("Heparan sulfate" or "HS") is initially synthesised in the Golgi apparatus as polysaccharides consisting of tandem repeats of D-glucuronic acid (GlcA) and N-acetyl-D-glucosamine (GlcNAc). The nascent polysaccharides may be subsequently modified in a series of steps: N-deacetylation/N-sulfation of GlcNAc, C5 epimerisation of GlcA to iduronic acid (IdoA), O-sulphation at C2 of IdoA and GlcA, O-sulphation at C6 of N-sulphoglucosamine (GlcNS) and occasional O-sulphation at C3 of GlcNS. N-deacetylation/N-sulphation, 2-O-, 6-O- and 3-O-sulphation of HS are mediated by the specific action of HS N-deacetylase/N-sulfotransferase (HSNDST), HS 2-O-sulfotransferase (HS2ST), HS 6-O-sulfotransferase (HS6ST) and HS 3-O-sulfotransferase, respectively. At each of the modification steps, only a fraction of the potential substrates are modified, resulting in considerable sequence diversity. This structural complexity of HS has made it difficult to determine its sequence and to understand the relationship between HS structure and function.

Heparan sulfate side chains consist of alternately arranged D-glucuronic acid or L-iduronic acid and D-glucosamine, linked via (1->4) glycosidic bonds. The glucosamine is often N-acetylated or N-sulfated and both the uronic acid and the glucosamine may be additionally O-sulfated. The specificity of a particular HSPG for a particular binding partner is created by the specific pattern of carboxyl, acetyl and sulfate groups attached to the glucosamine and the uronic acid. In contrast to heparin, heparan sulfate contains less N- and O-sulfate groups and more N-acetyl groups. The heparan sulfate side chains are linked to a serine residue of the core protein through a tetrasaccharide linkage (-glucuronosyl-β-(1→3)-galactosyl-β-(1→3)-galactosyl-β-(1→4)-xylosyl-β-1-O-(Serine)) region.

Both heparan sulfate chains and core protein may undergo a series of modifications that may ultimately influence their biological activity. Complexity of HS has been considered to surpass that of nucleic acids (Lindahl et al, 1998, J. Biol. Chem. 273, 24979; Sugahara and Kitagawa, 2000, Curr. Opin. Struct. Biol. 10, 518). Variation in HS species arises from the synthesis of non-random, highly sulfated sequences of sugar residues which are separated by unsulfated regions of disaccharides containing N-acetylated glucosamine. The initial conversion of N-acetylglucosamine to N-sulfoglucosamine creates a focus for other modifications, including epimerization of glucuronic acid to iduronic acid and a complex pattern of O-sulfations on glucosamine or iduronic acids. In addition, within the non-modified, low sulfated, N-acetylated sequences, the hexuronate residues remain as glucuronate, whereas in the highly sulfated N-sulfated regions, the C-5 epimer iduronate predominates. This limits the number of potential disaccharide variants possible in any given chain but not the abundance of each. Most modifications occur in the N-sulfated domains, or directly adjacent to them, so that in the mature chain there are regions of high sulfation separated by domains of low sulfation (Brickman et al. (1998), J. Biol. Chem. 273(8), 4350-4359, which is herein incorporated by reference in its entirety).

HS structure is highly complex and variable between HS. Indeed, the variation in HS structure is considered to play an important part in contributing toward the different activity of each HS in promoting cell growth and directing cell differentiation. The structural complexity is considered to surpass that of nucleic acids and although HS structure may be characterised as a sequence of repeating disaccharide units having specific and unique sulfation patterns at the present time no standard sequencing technique equivalent to those available for nucleic acid sequencing is available for determining HS sequence structure. In the absence of simple methods for determining a definitive HS sequence structure HS molecules are positively identified and structurally characterised by skilled workers in the field by a number of analytical techniques. These include one or a combination of disaccharide analysis, tetrasaccharide analysis, HPLC and molecular weight determination. These analytical techniques are well known to and used by those of skill in the art.

Two techniques for production of di- and tetra-saccharides from HS include nitrous acid digestion and lyase digestion. A description of one way of performing these digestion techniques is provided below, purely by way of example, such description not limiting the scope of the present invention.

Nitrous Acid Digestion

Nitrous acid based depolymerisation of heparan sulphate leads to the eventual degradation of the carbohydrate chain into its individual disaccharide components when taken to completion.

For example, nitrous acid may be prepared by chilling 250 μl of 0.5 M $H_2SO_4$ and 0.5 M $Ba(NO_2)_2$ separately on ice for 15 min. After cooling, the $Ba(NO_2)_2$ is combined with the $H_2SO_4$ and vortexed before being centrifuged to remove the barium sulphate precipitate. 125 μl of $HNO_2$ was added to GAG samples resuspended in 20 μl of $H_2O$, and vortexed before being incubated for 15 min at 25° C. with occasional mixing. After incubation, 1 M $Na_2CO_3$ was added to the sample to bring it to pH 6. Next, 100 μl of 0.25 M $NaBH_4$ in 0.1 M NaOH is added to the sample and the mixture heated to 50° C. for 20 min. The mixture is then cooled to 25° C. and acidified glacial acetic acid added to bring the sample to pH 3. The mixture is then neutralised with 10 M NaOH and the volume decreased by freeze drying. Final samples are run on a Bio-Gel P-2 column to separate di- and tetrasaccharides to verify the degree of degradation.

Lyase Digestion

Heparinise III cleaves sugar chains at glucuronidic linkages. The series of Heparinase enzymes (I, II and III) each display relatively specific activity by depolymerising certain heparan sulphate sequences at particular sulfation recognition sites. Heparinase I cleaves HS chains with NS regions along the HS chain. This leads to disruption of the sulphated domains. Heparinase III depolymerises HS with the NA domains, resulting in the separation of the carbohydrate chain into individual sulphated domains. Heparinase II primarily cleaves in the NA/NS "shoulder" domains of HS chains, where varying sulfation patterns are found. Note: The repeating disaccharide backbone of the heparan polymer is a uronic acid connected to the amino sugar glucosamine. "NS" means the amino sugar is carrying a sulfate on the amino group enabling sulfation of other groups at C2, C6 and C3. "NA" indicates that the amino group is not sulphated and remains acetylated.

For example, for depolymerisation in the NA regions using Heparinase III both enzyme and lyophilised HS samples are prepared in a buffer containing 20 mM Tris-HCL, 0.1 mg/ml BSA and 4 mM $CaCl_2$ at pH 7.5. Purely by way of example, Heparinase III may be added at 5 mU per 1 μg of HS and incubated at 37° C. for 16 h before stopping the reaction by heating to 70° C. for 5 min.

Di- and tetrasaccharides may be eluted by column chromatography.

A subject may be any animal or human. The subject is preferably mammalian, more preferably human.

Methods according to the present invention may be performed in vitro or in vivo, as indicated. The term "in vitro" is intended to encompass procedures with cells in culture whereas the term "in vivo" is intended to encompass procedures with intact multi-cellular organisms.

Dosages of Heparan Sulphate

In both in vitro and in vivo uses, HS8 may be used in concentrations or dosages of about 500 ng/ml or less, more preferably one of 250 ng/ml or less, 100 ng/ml or less, 90 ng/ml or less, 80 ng/ml or less, 70 ng/ml or less, 60 ng/ml or less, 50 ng/ml or less, 40 ng/ml or less, 30 ng/ml or less, 20 ng/ml or less, 10 ng/ml or less, 5 ng/ml or less; or of about 100 mg or less, 50 mg or less, 40 mg or less, 30 mg or less, 20 mg or less, 10 mg or less, 5 mg or less, 4 mg or less, 3 mg or less, 2 mg or less, or 1 mg or less; or about between 0.3-5 μg/ml, 0.3-4, 0.3-3, 0.3-2.5, 0.3-2, 0.3-1.5, 0.3-1.0, 0.3-0.9, 0.3-0.8, 0.3-0.7, 0.3-0.6, 0.3-0.5, 0.3-0.4, 1-2, 1-1.75, 1-1.5, 1-1.25, 1.25-2, 1.5-2, or 1.75-2 μg/ml.

FGF2

In this specification FGF2 refers to fibroblast growth factor 2 (also known as basic fibroblast growth factor (bFGF) or FGF-β) which is a member of the fibroblast growth factor family.

FGF2 is present in the basement membranes of many tissues and is thought to stay membrane bound in the absence of a signal stimulus. FGF2 has been implicated in wound healing, tumor development and angiogenesis.

Binding of FGF2 to Its tyrosine kinase receptor stimulates a signal cascade involving activation of mitogen activated protein kinase (MEK) and phosphorylation of extracellular signal-related kinases (ERKs) (e.g. see Ok-Jin Park et al., The Journal of Biological Chemistry, 285, (2010) 3568-3574).

The amino acid sequence of FGF2 from *Homo sapiens* is shown in FIG. 12 (the heparin binding domain SEQ ID NO:1 is underlined). This sequence is available in Genbank under Accession no. NP_001997.5 (GI:153285461).

In this specification "FGF2" includes proteins or polypeptides having at least 70%, more preferably one of 75%, 80%, 85%, 90%, 95%, 96%, 97%, 98%, 99% or 100% sequence identity with the amino acid sequence of FGF2 illustrated in FIG. 12.

The FGF2 protein or polypeptide preferably also includes a heparin binding domain having the amino acid sequence of SEQ ID NO:1, or an amino acid sequence having one of 75%, 80%, 85%, 90%, 95%, 96%, 97%, 98%, or 99% sequence identity to SEQ ID NO:1.

An FGF2 protein or polypeptide may be a fragment or truncate of a full length FGF2 protein or polypeptide.

The FGF2 protein may be from, or derived from, any animal or human, e.g. non-human animals, e.g. rabbit, guinea pig, rat, mouse or other rodent (including from any animal in the order Rodentia), cat, dog, pig, sheep, goat, cattle (including cows, e.g. dairy cows, or any animal in the order Bos), horse (including any animal in the order Equidae), donkey, and non-human primate or other non-human vertebrate organism; and/or non-human mammalian animal; and/or human.

Dosages of FGF2

In both in vitro and in vivo uses, FGF2 may be used in combination with HS8. In some cell culture methods of the present invention exogenous HS2 is added to the culture. Suitable concentrations or dosages of FGF2 include about 500 ng/ml or less, more preferably one of 250 ng/ml or less, 100 ng/ml or less, 90 ng/ml or less, 80 ng/ml or less, 70 ng/ml or less, 60 ng/ml or less, 50 ng/ml or less, 40 ng/ml or less, 30 ng/ml or less, 20 ng/ml or less, 10 ng/ml or less, 5 ng/ml or less; or of about 100 mg or less, 50 mg or less, 40 mg or less, 30 mg or less, 20 mg or less, 10 mg or less, 5 mg or less, 4 mg or less, 3 mg or less, 2 mg or less, or 1 mg or less; or between about range 0.1-5 ng/ml, 0.1-0.2, 0.1-0.3, 0.1-0.4, 0.1-0.5, 0.1-0.6, 0.1-0.7, 0.1-0.8, 0.1-0.9, 0.1-1.0, 0.1-1.5, 0.1-0.2.0, 0.1-2.5, 0.1-3.0, 0.1-3.5, 0.1-4.0, 0.1-4.5, 0.1-5.0 ng/ml.

In some embodiments, in vitro and in vivo uses of HS8 exclude the addition of exogenous FGF2.

The invention includes the combination of the aspects and preferred features described except where such a combination is clearly impermissible or expressly avoided.

The section headings used herein are for organizational purposes only and are not to be construed as limiting the subject matter described.

Aspects and embodiments of the present invention will now be illustrated, by way of example, with reference to the accompanying figures. Further aspects and embodiments will be apparent to those skilled in the art. All documents mentioned in this text are incorporated herein by reference.

BRIEF DESCRIPTION OF THE FIGURES

Embodiments and experiments illustrating the principles of the invention will now be discussed with reference to the accompanying figures in which:

FIG. 3. Table showing FGF2 Heparin binding domain peptides.

FIG. 10. Graph showing binding capacity of different GAGs for FGF2 as assessed by GAG-binding plates (Iduron). The HS8 (HS8+) fraction binds FGF2 almost as well as heparin, and better than the raw starting Celsus HS and the HS8− flow through.

FIG. 12. Amino acid sequence of human FGF2. SEQ ID NO:1 shown in underline.

FIG. 13. Nitrous acid-derived disaccharide composition of heparan sulfate from E10 neuroepithelia (HS2). Radiolabelled HS was depolymerized by deaminitive cleavage with low pH HNO$_2$. Disaccharides were isolated after HNO$_2$ treatment of the GAGs and the samples then run on a 1×120 cm Bio-Gel P-2 column. The resulting disaccharides were fractionated by SAX-HPLC. Areas under the peaks were integrated to give the disaccharide composition and subsequently, the percentage composition in each sample.

FIG. 14. Disaccharide composition of heparan sulfate from E10 neuroepithelium (HS2) following heparin lyase treatment. Heparan sulfate was completely depolymerized with a mixture of heparan lyases. The resulting unsaturated disaccharides were isolated on a P-2 column and fractionated by strong anion exchange column chromatography. The area under each resultant curve was integrated to calculate the percentage of each disaccharide in each sample. Numbers represent the average of two runs (for the primary GAG samples) and three runs (for the 2.3D derived samples). Over 97% disaccharides were recovered from each sample.

Comparison of digestion of Celsus HS Lot #10697 to a previous analysis on the same sample.

Figure 25:
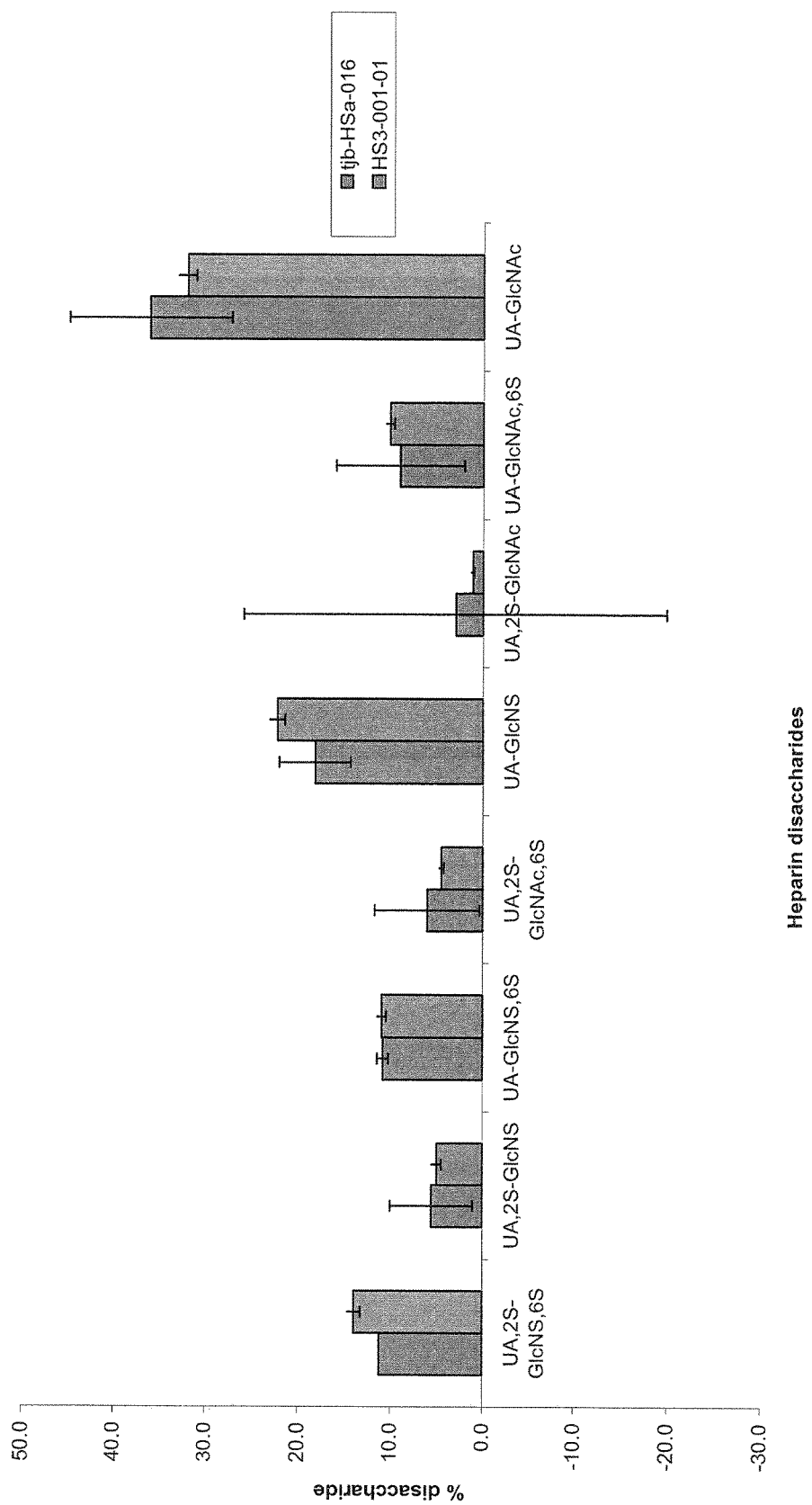

FIG. 25. Graph showing normalized disaccharide composition for HS3. Comparison of digestion of HS3-001-01.

Figure 26:
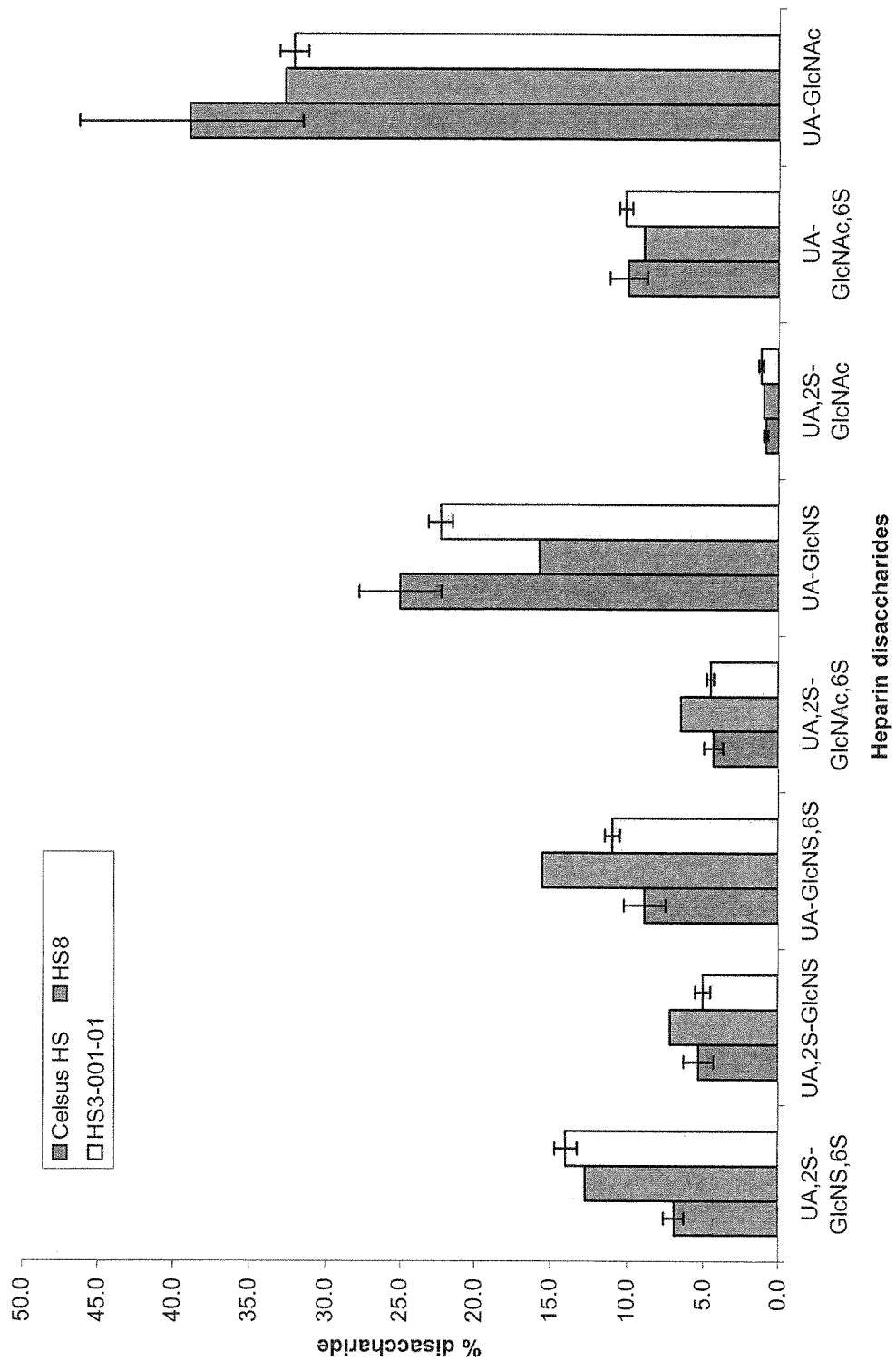

FIG. 26. Graph showing disaccharide composition of Celsus HS, HS8 and HS3.

Figures 27, 28:
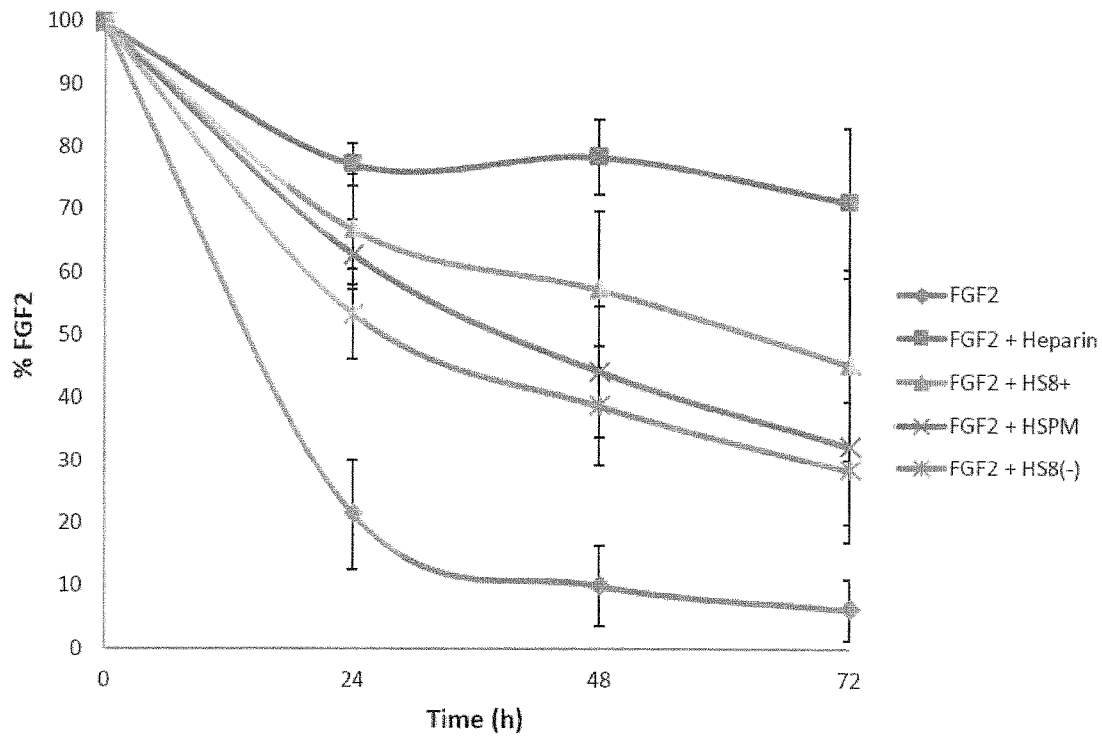

FIG. 27. Table showing percentage disaccharide composition of Celsus, HS, HS3 and HS8.

FIG. 28. Graph showing stability of FGF-2 in the presence of no HS, heparin, HS8, Celsus HS (HSPM) or HS8–. FGF-2 is stabilized in the presence of HS8.

Figure 29:
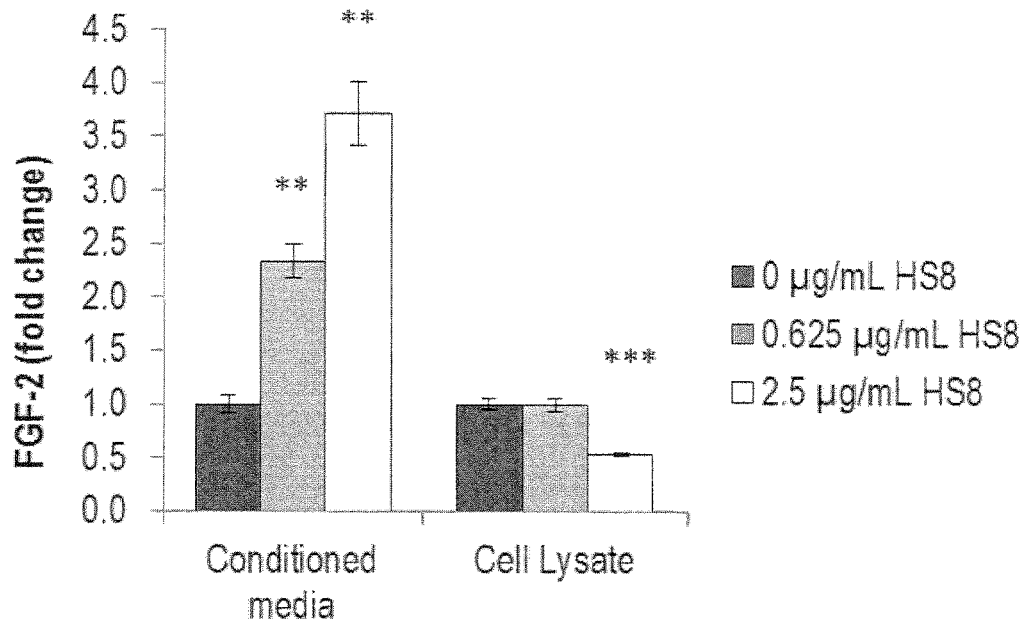

FIG. 29. Graph showing HS8 modulates the availability of endogenous FGF-2 in epidermal keratinocytes. ) $p<0.01$, *) $p<0.001$.

Figure 30:
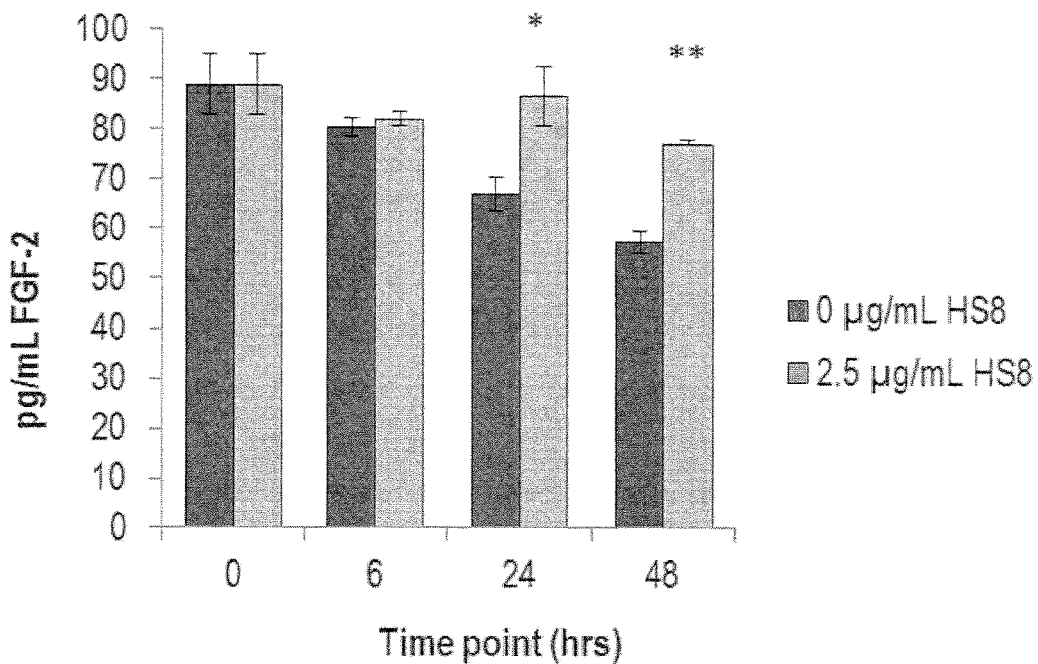

FIG. 30. Graph showing HS8 stabilizes endogenous FGF-2 secreted by epidermal keratinocytes. *) $p<0.05$, **) $p<0.01$.

Figure 31:
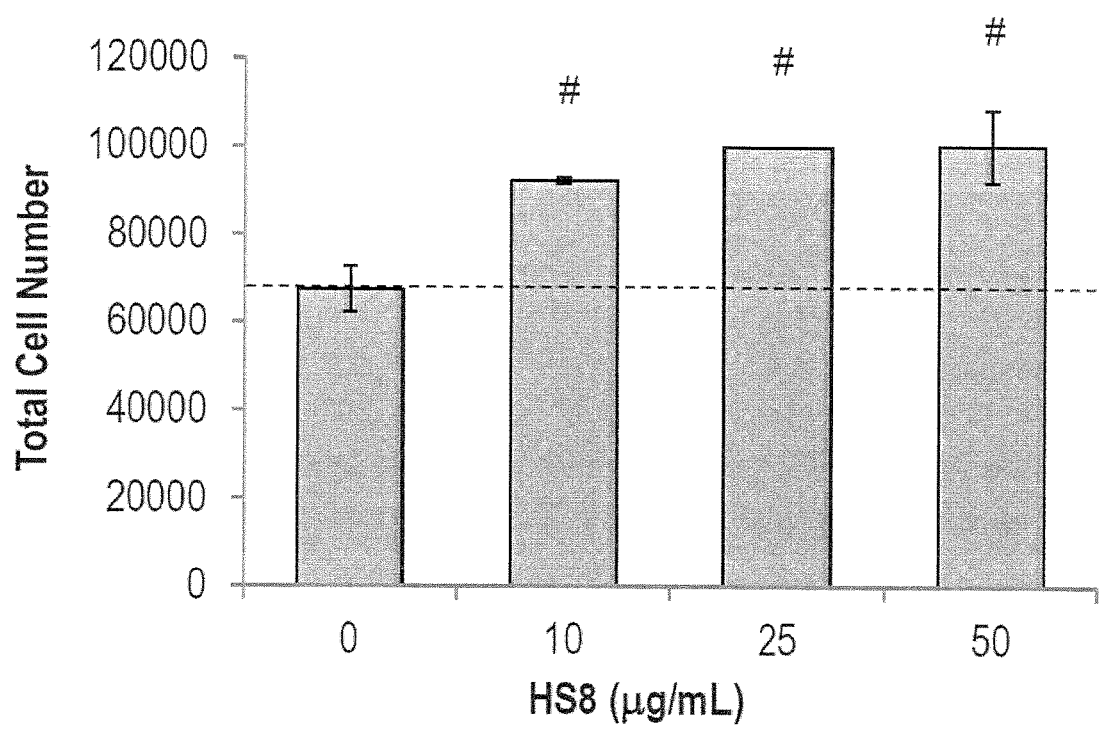

FIG. 31. Graph showing HS8 enhances dermal fibroblast proliferation. #) $p<0.05$.

Figure 32A:
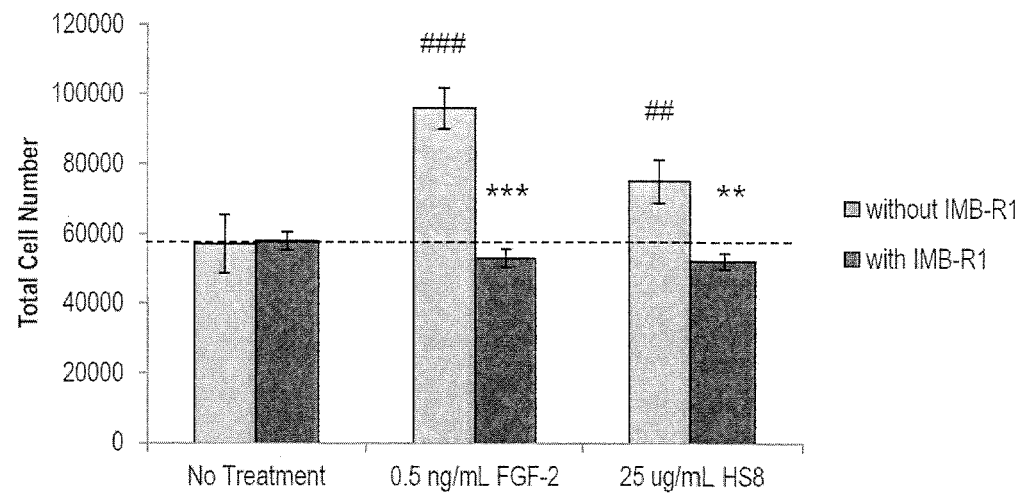

FIG. 32. Graphs showing FGF-2 contributes toward HS8-induced fibroblast proliferation as shown through the neutralizing effect of A) IMB-R1, an FGF-R1 specific neutralizing antibody, and B) PD173074, a chemical inhibitor specific to FGF-R1 and FGF-R3. ##) $p<0.01$ and ###) $p<0.001$ when compared to no treatment. ) $p<0.01$ and *) $p<0.001$ when comparing without and with IMB-R1 or PD173074.

Figure 33:
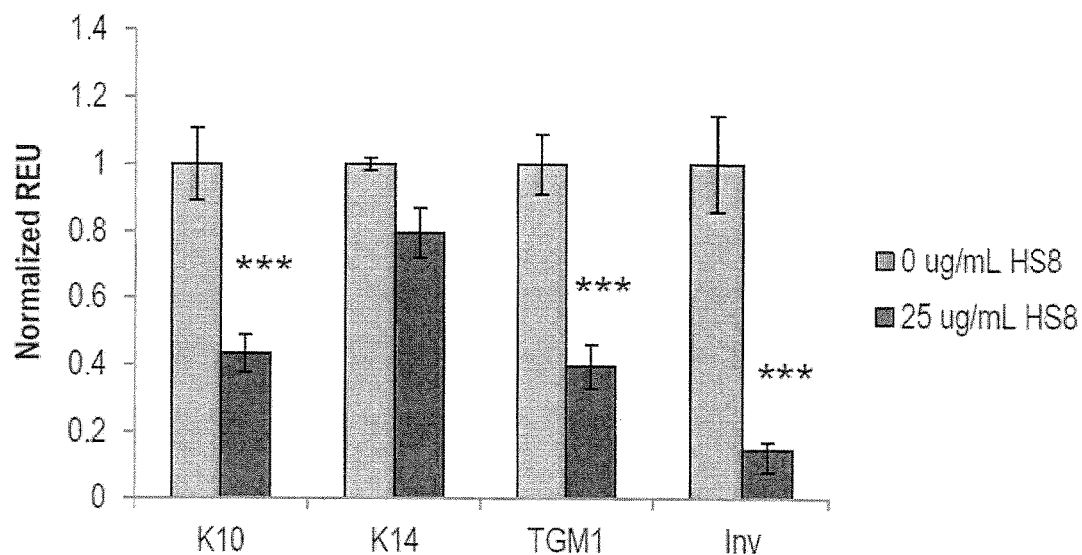

FIG. 33. Graph showing HS8 significantly modulates keratinocytes differentiation markers keratin 10 (K10), transglutaminase-1 (TGM1) and involucrin (Inv). ###) $p<0.001$ when comparing 0 and 25 µg/mL HS8.

Figure 34:
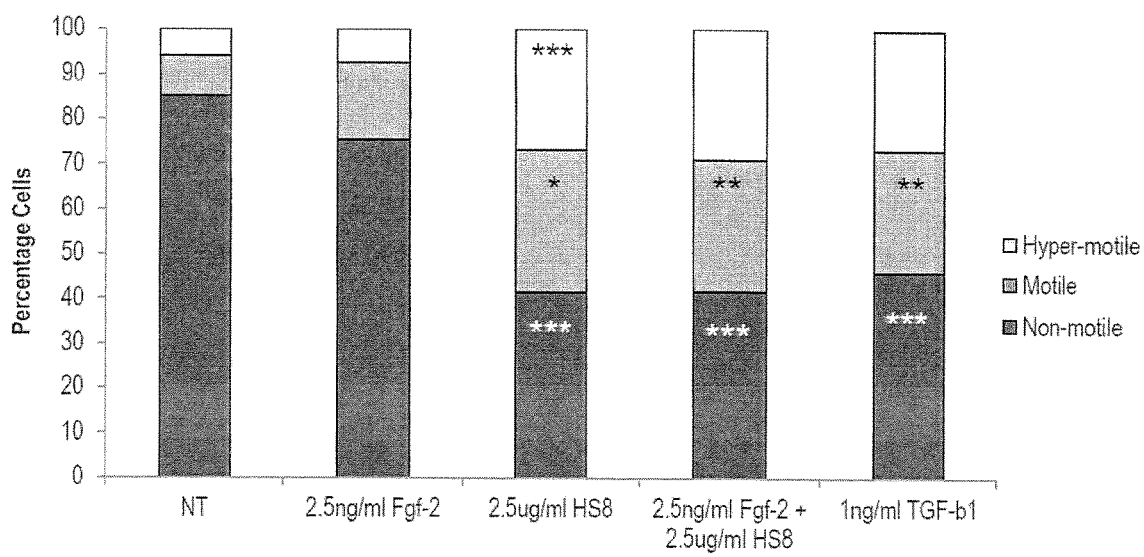

FIG. 34. Graph showing HS8 modulates keratinocytes motility, comparable to the positive control TGF-β1. *) $p<0.05$, ) $p<0.01$, and *) $p<0.001$ when compared to no treatment.

Figure 35A:
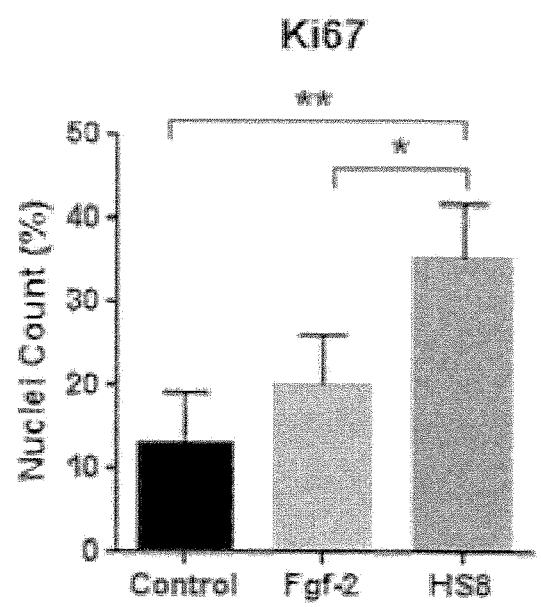
Figure 35B:
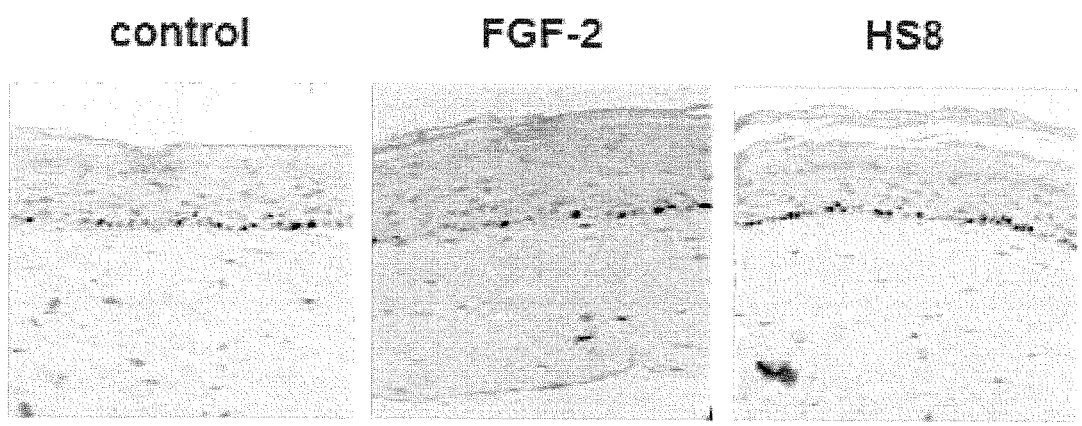

FIG. 35. Graph and photographs showing HS8 enhances basal keratinocyte proliferation. (A) Graph and (B) photographs showing HS8 enhances basal keratinocyte proliferation, demonstrated by an increase in staining for cellular marker of proliferation Ki67, in reconstructed full thickness skin model compared to control and FGF-2. *) $p<0.05$ and **) $p<0.01$.

Figure 36A:
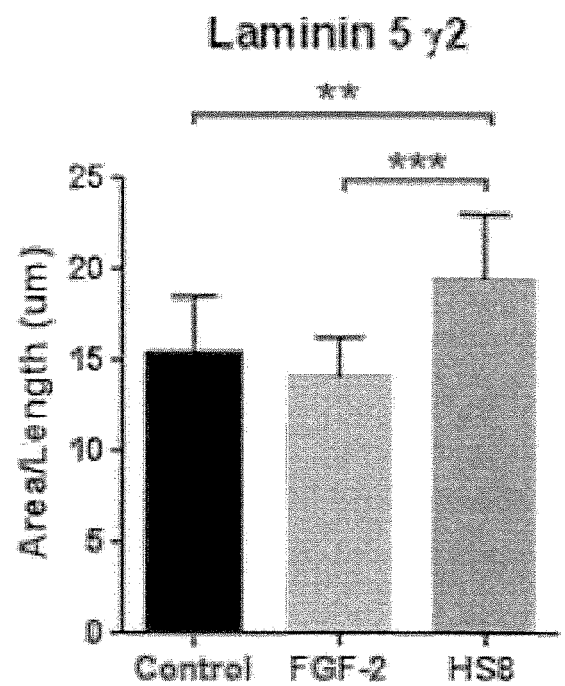
Figure 36B:
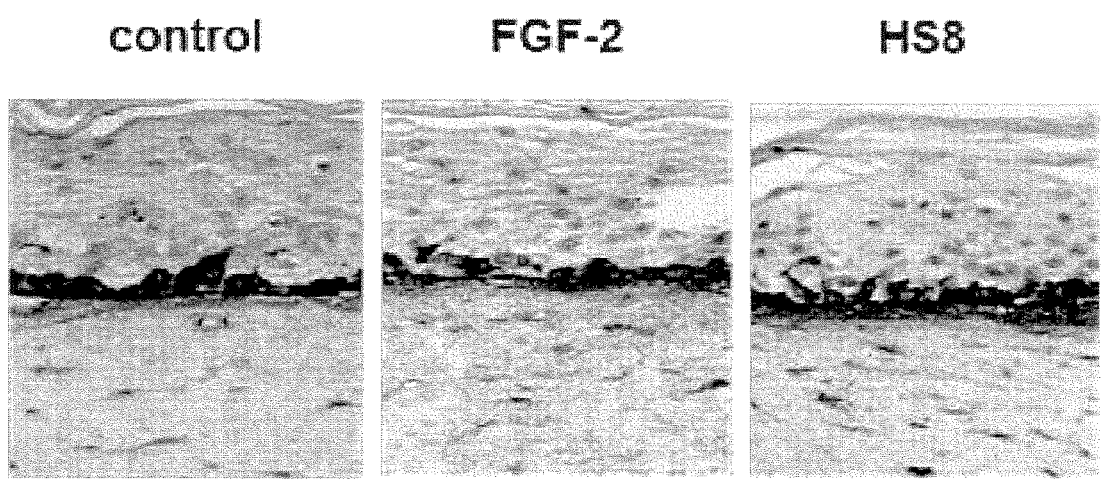

FIG. 36. Graph and photographs showing HS8 enhances expression of the dermal-epidermal basement membrane component laminin 5 γ2. (A) Graph and (B) photographs showing HS8 enhances expression of laminin 5 γ2 in reconstructed full thickness skin model compared to control and FGF-2. Level of expression was quantified based on the area of staining normalised to the length of dermal-epidermal junction analysed. ) $p<0.01$ and *) $p<0.001$.

Figure 37A:
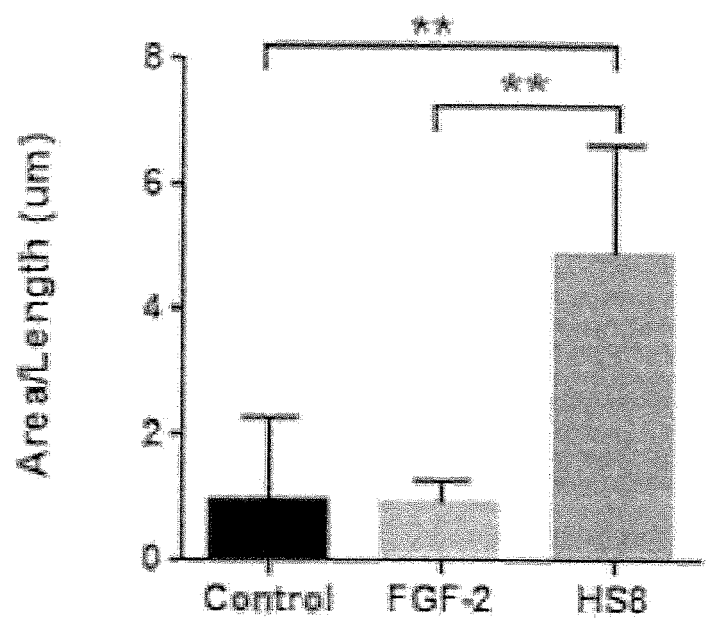
Figure 37B:
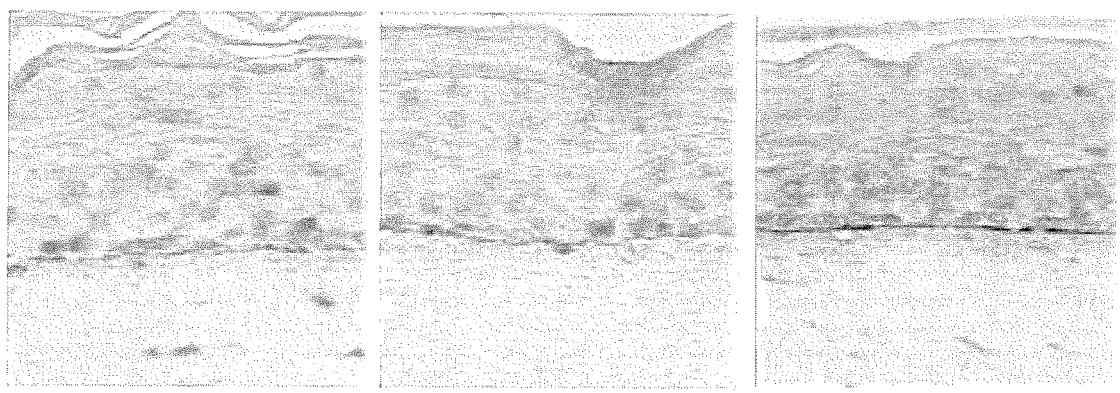

FIG. 37. Graph and photographs showing HS8 enhances expression of the dermal-epidermal basement membrane component collagen IV. (A) Graph and (B) photographs showing HS8 enhances expression of collagen IV in reconstructed full thickness skin model compared to control and FGF-2. Level of expression was quantified based on the area of staining normalised to the length of dermal-epidermal junction analysed. ) $p<0.01$ and *) $p<0.001$.

DETAILED DESCRIPTION OF THE INVENTION

The details of one or more embodiments of the invention are set forth in the accompanying description below including specific details of the best mode contemplated by the inventors for carrying out the invention, by way of example. It will be apparent to one skilled in the art that the present invention may be practiced without limitation to these specific details.

EXAMPLES

Example 1

We investigated the purification of a new FGF2 binding HS from commercially available Porcine Celsus Heparan sulphate sources suitable for scale up of heparan sulphate (HS) preparations that can be readily used in the clinic.

The Heparin binding domain (HBD) peptide sequence GHFKDPKRLYCKNGGF [SEQ ID NO:1] from FGF2 was selected (The structure of glycosaminoglycans and their interactions with proteins; Gandhi N S and Mancera R L., Chem Biol Drug Des. 2008 December; 72(6):455-82) and used to purify specific HS species binding to FGF2.

Upon synthesizing the peptide, it was subjected to the $^3$H Heparin assay where specific binding of $^3$H Heparin to the peptide soaked to a nitrocellulose membrane in a dose dependent manner was compared to the total counts of the $^3$H Heparin. Once the specific binding of $^3$H Heparin to the FGF2-HBD peptide was shown the peptide was used to pull down a specific HS from Porcine Celsus HS which binds to FGF2 by affinity chromatography. This new HS species was named as HS8 (and was given the variant name HS8G).

HS8 was analysed for its specificity in binding with FGF2 with glycosaminoglycan (GAG) binding plates where the specific binding of HS8 to FGF2 was measured in comparison to Heparin, Porcine Celsus HS and HS8 negative fraction.

The GAGs were plated on GAG binding plate (5 µg/ml) overnight and later incubated with recombinant human FGF2 (0-100 ng/ml) and an ELISA method was used to check the specificity of binding of GAGs to FGF2.

Figure 1:
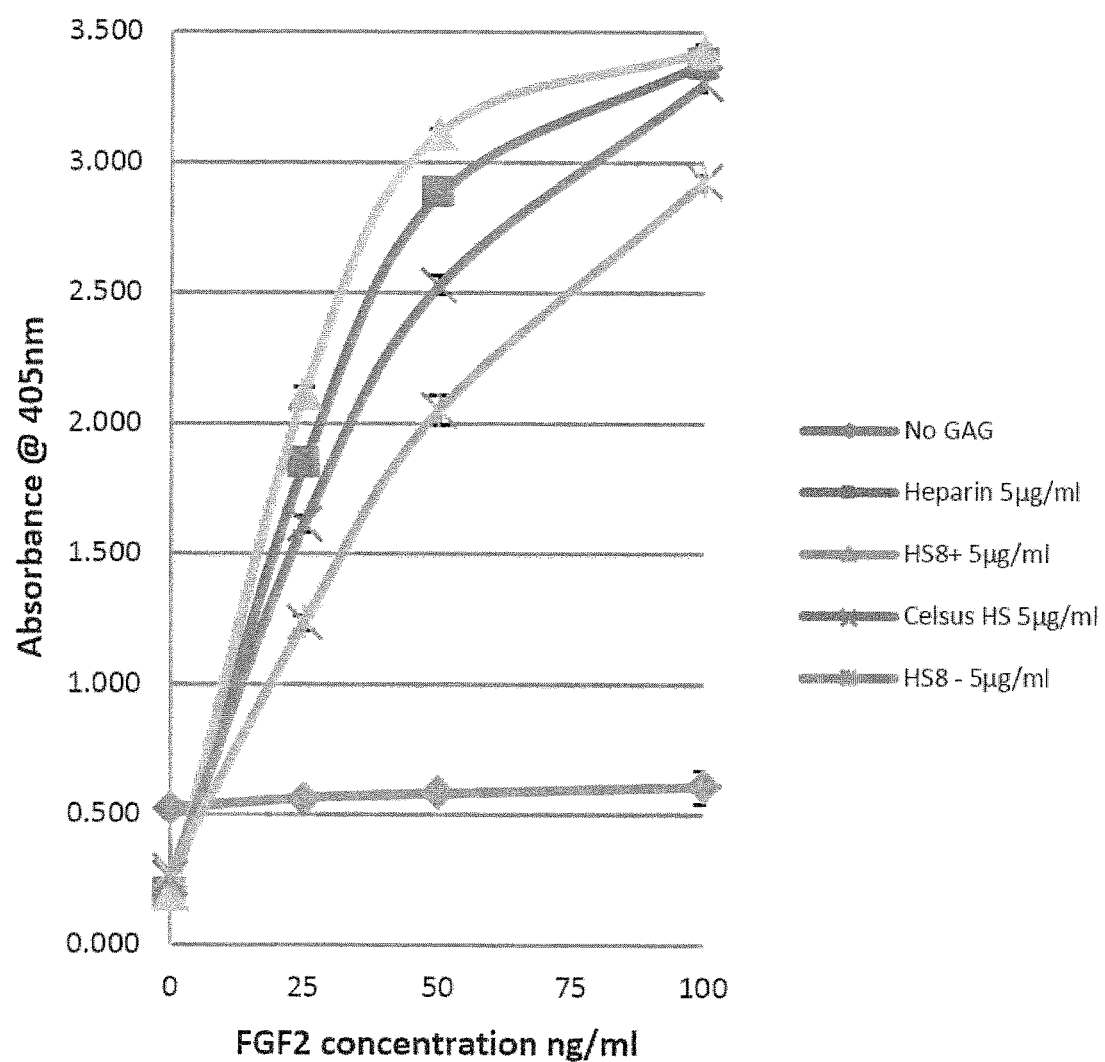
FIG. 1. Graph showing binding of different GAGs (5 µg/ml) to FGF2 (1-100 ng/ml). Preferential binding of HS8 to FGF2 was observed at concentrations of FGF2 of 0, 25, 50 and 100 ng/ml. Data lines from top of graph down: HS8+(5 µg/ml) (triangles), Heparin (5 µg/ml) (squares), Celsus HS (5 µg/ml), HS8− (5 µg/ml), No GAG (diamonds).
Figure 2:
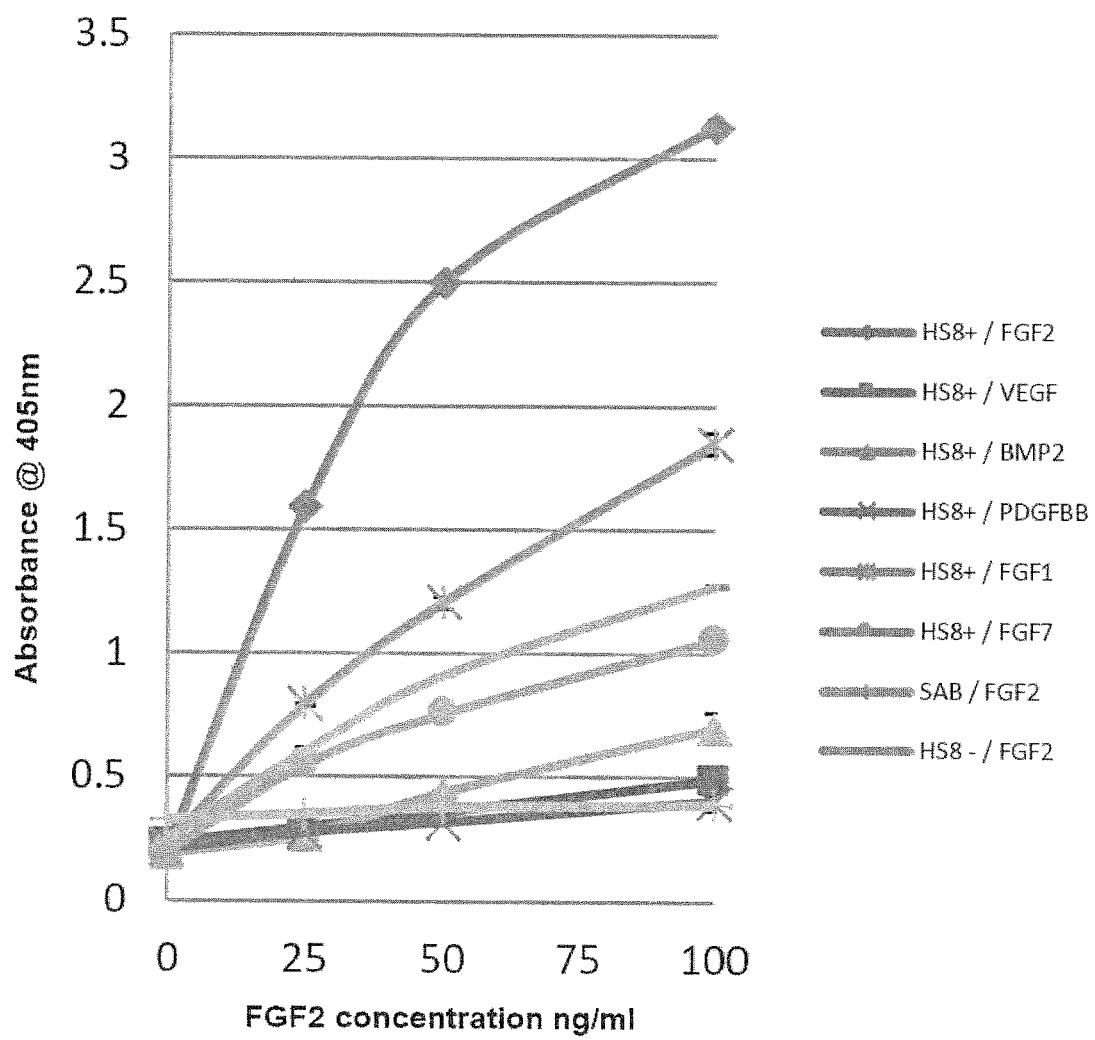
FIG. 2. Graph showing HS8+ binding (5 µg/ml) to different proteins (0-100 ng/ml), demonstrating specificity of HS8 (5 µg/ml) for FGF2. Data lines from top of graph down: HS8+/FGF2 (diamonds), HS8+/FGF1, HS8−/FGF2, HS8+/FGF7, HS8+/BMP2, HS8+/VEGF, SAB/FGF2, HS8+/PDGFBB.

The results clearly showed that HS8 has more binding to FGF2 compared to other GAG species (FIG. 1). The ability of HS8 to bind FGF2 was compared against other growth factors (VEGF, BMP2, PDGFBB, FGF1, and FGF7) which revealed that HS8 is specific to FGF2 (FIG. 2).

Example 2

Heparin and Heparan Sulfate Glycosaminoglycans (HS-GAGs)

Heparin is produced and stored in mast cells and in comparison, HSGAGs are found in all animal tissues and they can occur as a proteoglycan where HS chains are bound to cell surface or ECM proteins. HS affects metabolism, transport, information transfer, cell adhesion, cell growth and differentiation, and support in all organ systems (Bishop et al, 2007 and Gandhi et al, 2008). Heparin and HS are linear polysaccharides consisting of repeating uronic acid-(1→4)-D-glucosamine disaccharide subunits. Uronic acid can either be D-glucuronic acid or L-iduronic acid. In addition, modifications at specific places give rise to different N-sulfated, O-sulfated and N-acetylated complex sequences [Ori et al 2008]. The most abundant disaccharide in heparin is IdoA(2S)-(1→4)-GlcNS(6S) therefore giving rise to highly negative charge throughout the chain length, which makes heparin less or no selectivity in binding to proteins. On the other hand, HS has the unsulfated GlcA-(1→4)-GlcNA disaccharide as the most common form which giving rise to segregated blocks of unsulfated NA domains and blocks of highly sulfated, heparin-like IdoA-(1→4)-GlcNS disaccharides (NS domain). The NA and NS domain is separated by NA/NS transition domains. This diversity of HS structure is responsible for wide range of biological functions.

Fibroblast Growth Factor (FGF) Proteins and Heparin Binding Domains

Fibroblast growth factors (FGFs) are large family of polypeptide growth factors which comprise of 22 members in humans. They play a major role in development, differentiation, cell proliferation, angiogenesis and wound healing by binding and activating a subfamily of FGF cell surface receptor tyrosine kinases known as FGF receptors (FGFR) (Ornitz et al 1996). Furthermore, the FGFs are among the best-studied heparin-binding proteins, and HSGAGs regulate FGF signaling by direct molecular association with FGFRs (Pellegrini, 2001). In addition, FGF2 signaling through FGFR1 is important for MSC expansion (Gronthos et al, 1999).

Interactions of Heparin/HS with FGF2

Various studies have recognized common structural features in the heparin/HS binding sites of proteins (Gandhi et al, 2008; Hileman et al, 1998 and Ori et al, 2008). Cardin and Weintraub in1989 made a first attempt to determine the heparin binding domain (HBD) after analyzing 21 heparin-binding proteins and proposed that typical heparin-binding sites may have the sequence XBBXBX or XBBBXXBX, where B is a positively charged amino acid (arginine, lysine and rarely histidine) and X is a hydropathic residue. The next consensus sequence TXXBXXTBXXXTBB, was introduced by Hileman et al in1998 after Comparing X-ray and NMR of several proteins. In this sequence T defines a turn, B a basic amino acid (arginine or lysine) and X a hydropathic residue.

Strong ionic interactions are expected between GAGs and proteins with positively charged basic amino acids form ionic bonds with negatively charged sulphate or carboxylate groups on heparin chains. Their role is determinant for the interaction with heparin and, possibly, with the highly sulfated regions within HS like NS domains (Fromm et al, 1997 and Ori et al, 2008). In addition, there are other types of bonds namely van der Waals forces, hydrogen bonds and hydrophobic interactions. These bonds will come in to play for the interactions with the more heterogeneous HS, where neutral amino acids are also required (Fromm et al, 1997 and Ori et al, 2008). In considering FGF2, Glutamine and asparagine amino acids play an important role for the interaction with HS by forming hydrogen bonds with the hydroxyl groups of the sugar in addition to the ionic bonds (Thompson et al, 1994).

According to the numerous published studies so far, there are different peptide sequences as the heparin binding domain of FGF2 and those have been compiled in the table 1. Here we have adopted a numbering system where the amino acids are numbered according to the full FGF2 sequence (288aa).

Results

Isolation of the Heparan Sulfate with Higher Binding Affinity to FGF-2 by Column Chromatography (HS8)

In line with the strategy of purifying the FGF2 binding HS2, we seek the possibility of purifying another FGF2 binding HS from commercially available Porcine Celsus heparan sulphate sources (Celsus Laboratories, USA) in order to scale up the HS preparation which could be readily used in the clinics. Out of these peptides sequences which are presented in the table 1 $^{157}$GHFKDPKRLYCKNGGF$^{172}$ (Gandhi et al, 2008) which was named FGF2-Gandhi-HBD was used.

[$^3$H] Heparin Assay

Upon synthesizing the peptides, they were subjected to $^3$H Heparin assay where the capability of the FGF2-HBD-peptides binding to heparin was tested. Known amounts of peptides or saturating amounts of peptides were dried onto identical nitrocellulose membranes which were first air dried and then further dried for 45 min in a vacuum oven at 80° C. Then membranes were washes with 1× phosphate buffered saline (PBS) and incubated in counting vials for 16 hr with 0.1 µCi of [$^3$H] heparin (Perkin Elmer, Boston, USA) in 4% (w/v) bovine serum albumin (BSA)/PBS. After that membranes were washed and the radioactivity was determined by Perkin Elmer Tri-Carb 2800 TCR Liquid Scintillation Analyzer.

Figure 4A:
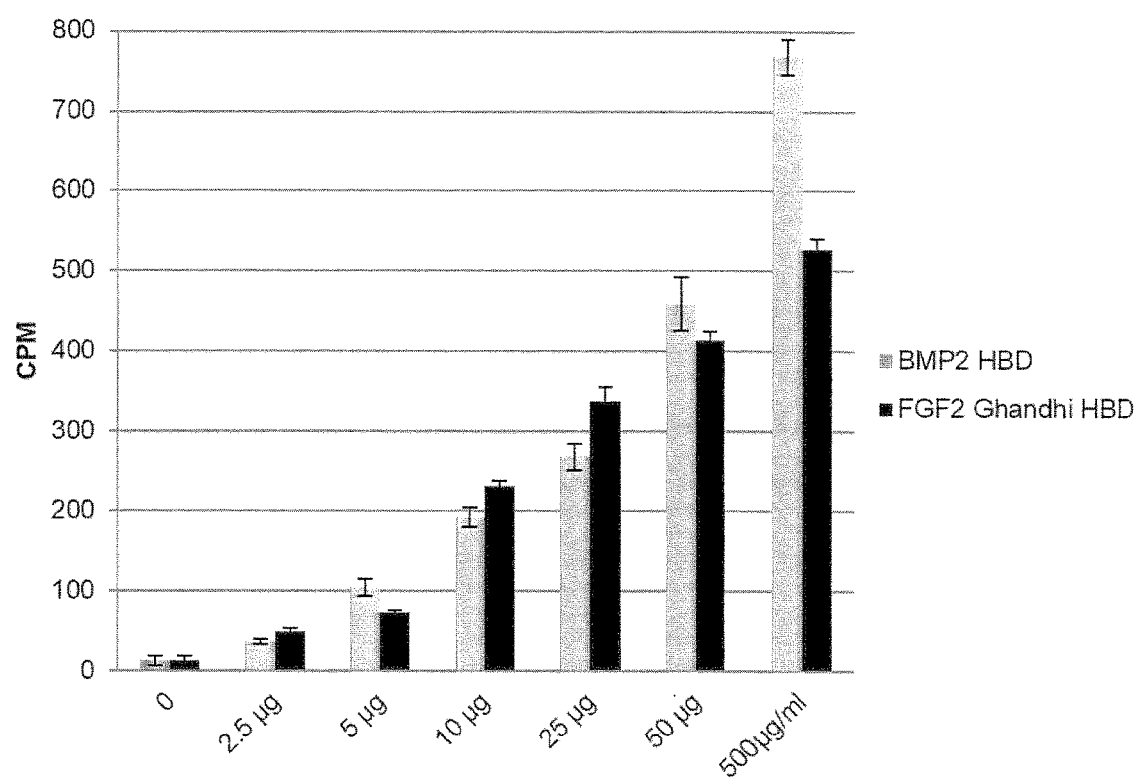
FIG. 4. Graphs showing results of a [$^3$H] assay. (A) Graph showing Radioactivity counts per minutes (CPM) for different amounts of peptide (B) Graph showing HS8 pull down by affinity chromatography FIG. 5. Diagram illustrating arrangement of GAG binding affinity assays.
Figure 4B:
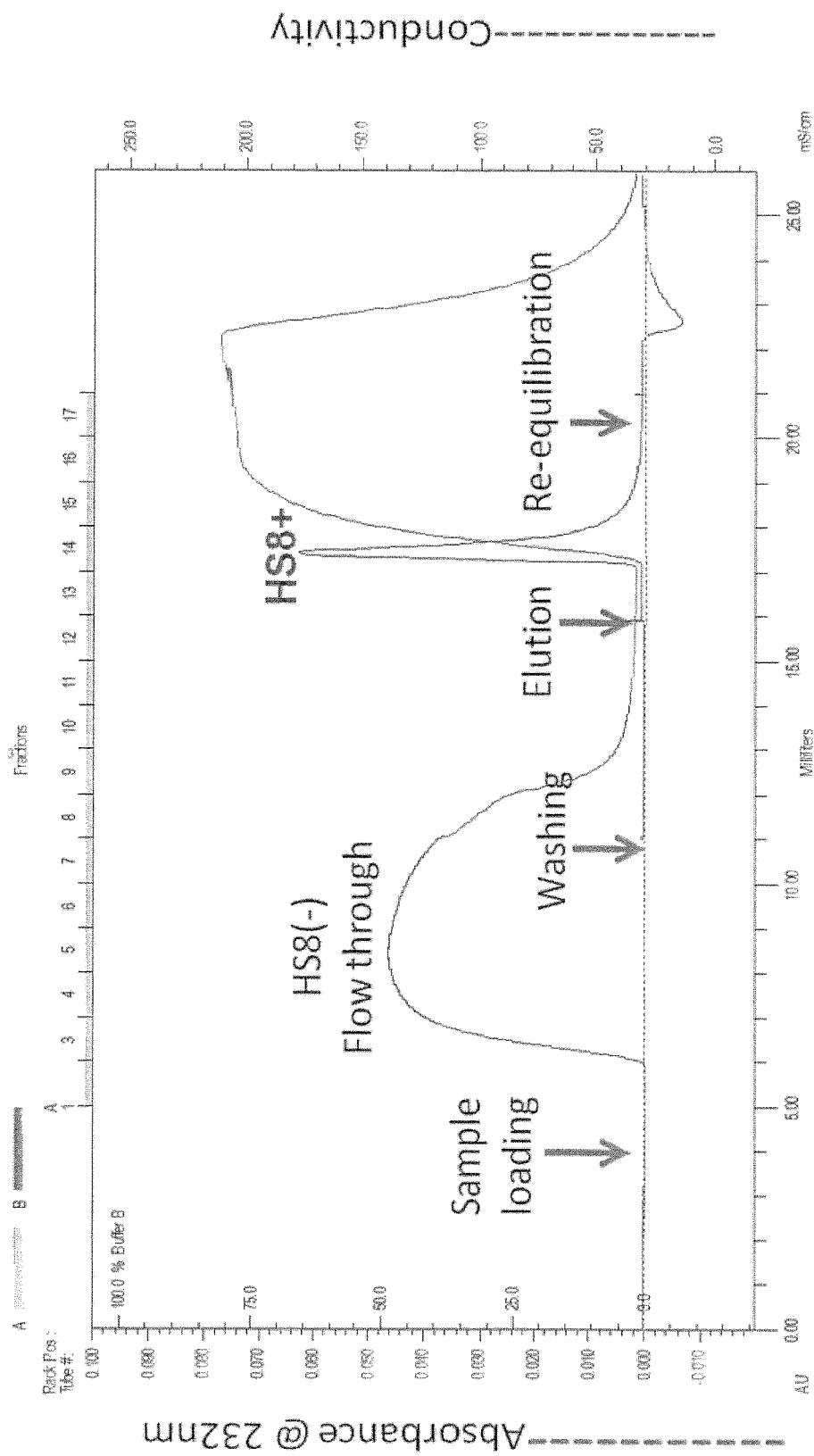
Figure 5:
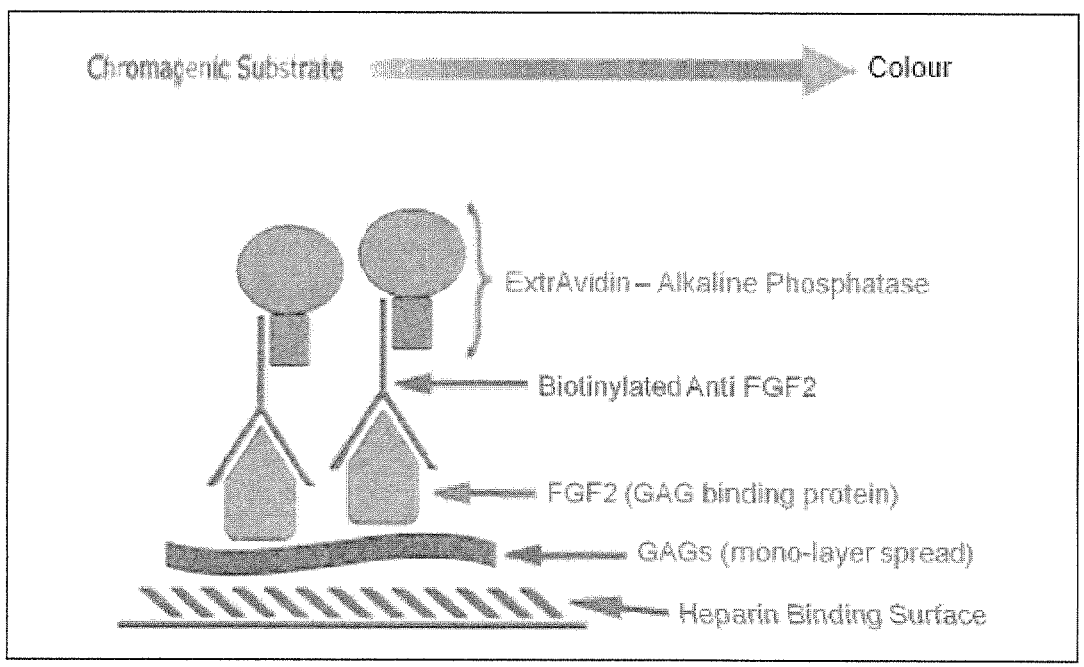
Figure 6A:
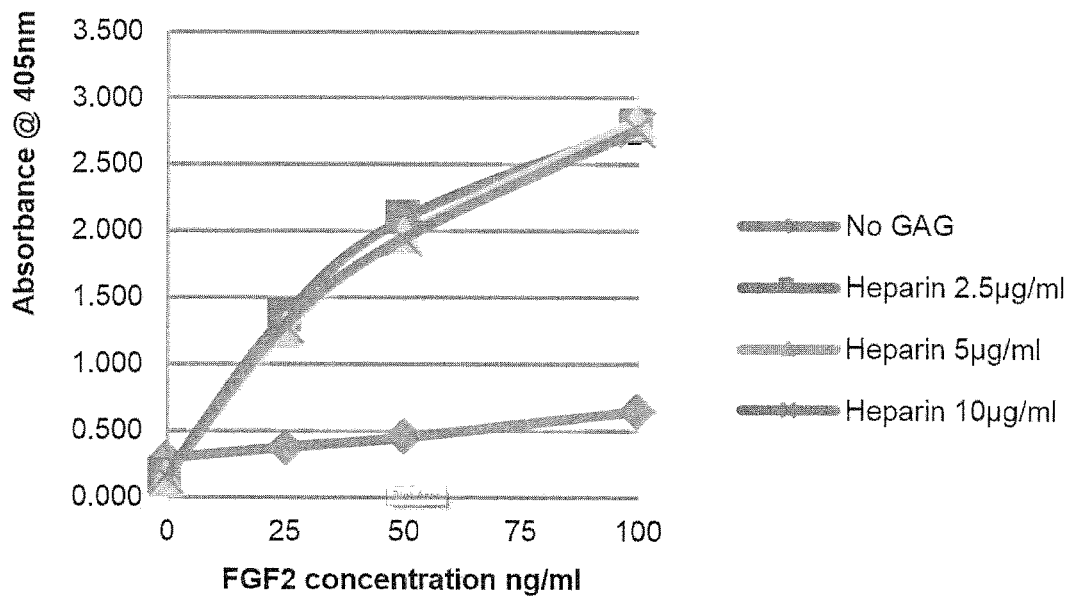
FIG. 6. Graphs showing optimization of different GAGs concentrations binding to FGF2. (A) Heparin (2.5, 5, 10 µg/ml) and FGF2 0, 25, 50, 100 ng/ml—SAB/0.2% Fish gelatin/ExtrAvidin AP 220 ng/ml. (B) HS8+(2.5, 5, 10 µg/ml) and FGF2 0, 25, 50, 100 ng/ml—SAB/0.2% Fish gelatin/ExtrAvidin AP 220 ng/ml. (C) Celsus HS (2.5, 5, 10 µg/ml) and FGF2 0, 25, 50, 100 ng/ml—SAB/0.2%, Fish gelatin/ExtrAvidin AP 220 ng/ml. (D) HS8(−) (2.5, 5, 10 µg/ml) and FGF2 0, 25, 50, 100 ng/ml—SAB/0.2%, Fish gelatin/ExtrAvidin AP 220 ng/ml FIG. 7. Graph showing different GAGs (2.5 µg/ml) binding to FGF2 (0, 25, 50, 100 ng/ml)—SAB/0.2% Fish Gelatin/ExtrAvidin AP 220 ng/ml.
Figure 6B:
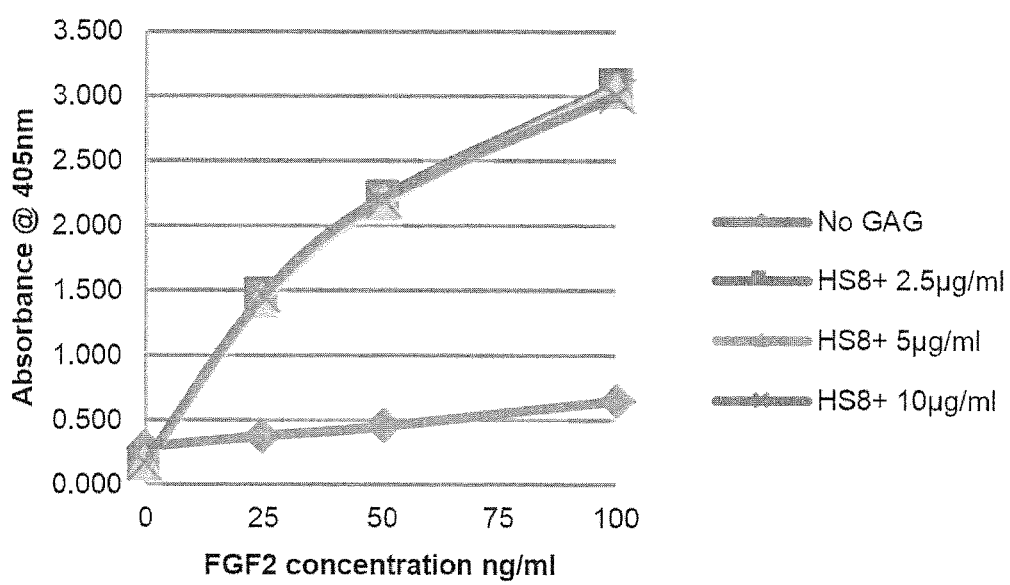
Figure 6C:
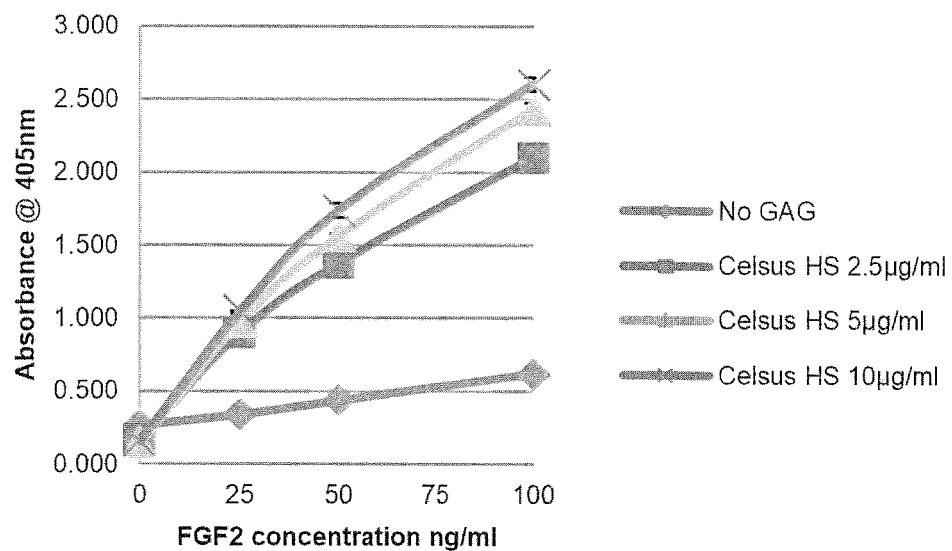
Figure 6D:
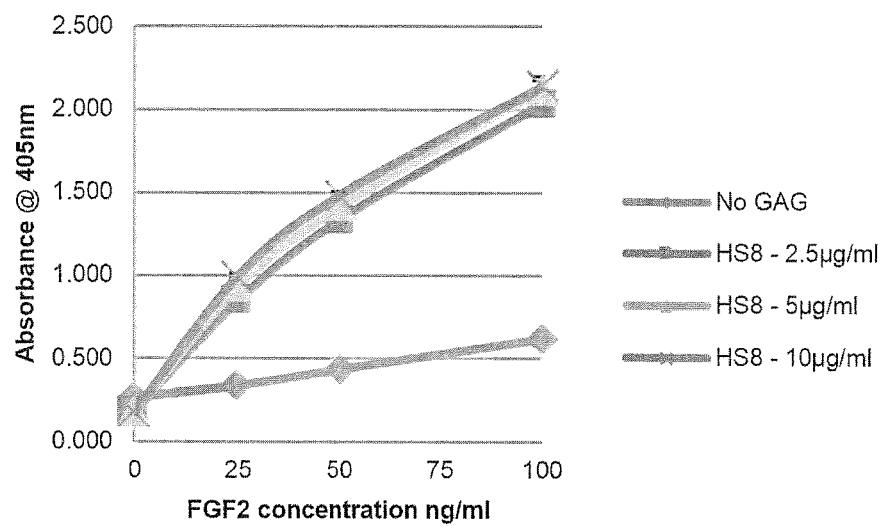

When known amounts of peptide (SEQ ID NO:1) was used they were showing increasing CPM dose dependently, where BMP2-HBD was used as a positive control [FIG. 4(A)]. But the highest counts were shown when the nitrocellulose membranes were saturated in 500 µg/ml peptide solution. The percentage CPM out of Neat [$^3$H] Heparin was calculated for each peptide at the 500 µg/ml solution level. BMP2-HBD (7.2%) had the highest followed by FGF2-Gandhi-HBD (4.97%). According to the results obtained from the [$^3$H] Heparin assay FGF2-Gandhi-HBD was used to pull down the higher affinity binding HS (HS8) to FGF2 from Porcine Celsus HS by affinity chromatography. The chromatogram is shown in the FIG. 4(B).

Characterization of HS8

GAG Binding Affinity Assays

HS8 was subjected to its affinity in binding to FGF2 and other proteins (R&D Systems) with 96 well GAG binding plates (Iduron, UK) where the specific binding of HS8+ to FGF2 measured in comparison to heparin (Sigma), Porcine Celsus HS (Celsus Laboratories, USA) and HS8 negative fraction. The GAGS were plated on GAG binding plate (2.5-10 µg/ml) overnight and blocked with 0.2% Fish Gelatin (Sigma) in standard assay buffer (SAB) for 1 hour at 37° C.

Then incubated with 200 µl/well of 0-100 ng/ml of recombinant human FGF2 for 2 hrs at 37° C. and later incubated with 200 µl/well of 250 ng/ml primary biotinylated antibody (R&D Systems) for 1 hour in 37° C. In the next step plate was incubated with 200 µl/well of 220 ng/ml ExtrAvidin-AP (Sigma) for 30 min at 37° C. From overnight incubation up to this step plate was washed 3 times with SAB in between each step. Finally, incubated with 200 µl/well SigmaFAST p-Nitrophenyl phosphate (Sigma) for 40 min and absorbance was read at 405 nm by Victor$^3$ 1420 multi-label counter, PerkinElmer.

Figure 7:
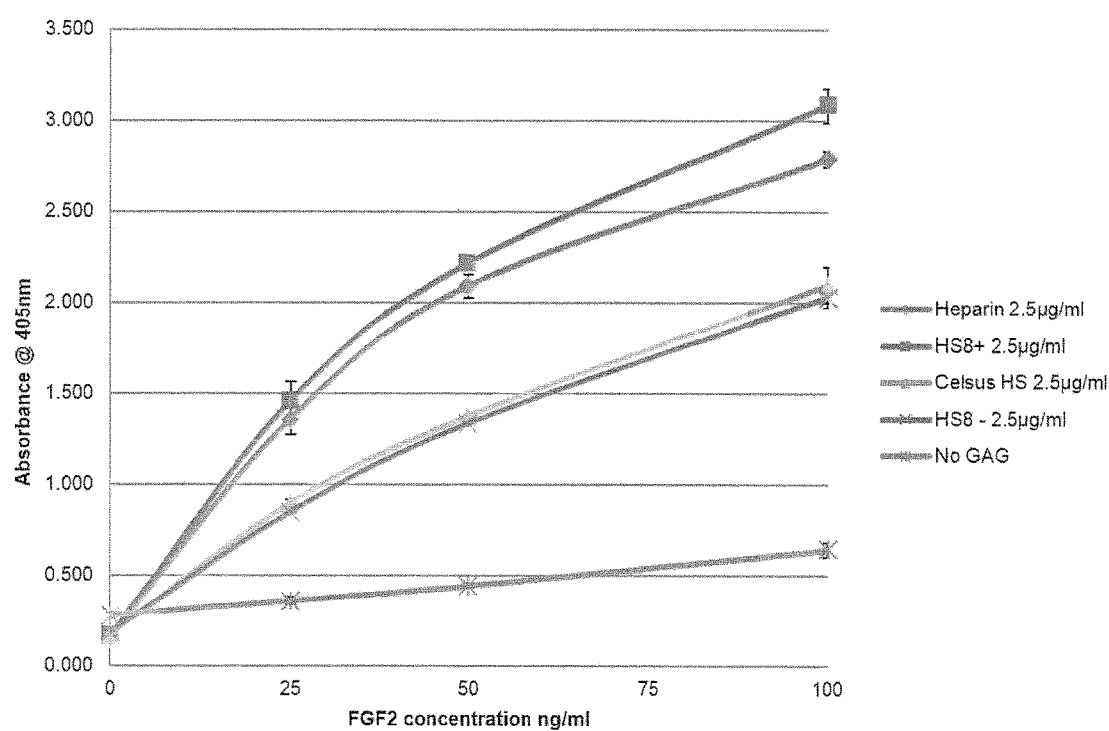

Binding of all the GAGs in all 3 concentrations tested (2.5, 5 and 10 µg/ml) to FGF2 increased similarly with increasing amounts of FGF2 and reached a saturation at 100 ng/ml FGF2 (FIG. 6). When different GAGs were tested on binding to FGF2, results clearly showed that HS8+ had the highest affinity of binding to FGF2 to other GAG species (FIG. 7). When compared the fold difference of Celsus HS: HS8+ at 100 ng/ml FGF2 point, the ratio was 1; 1.51.

Figure 8A:
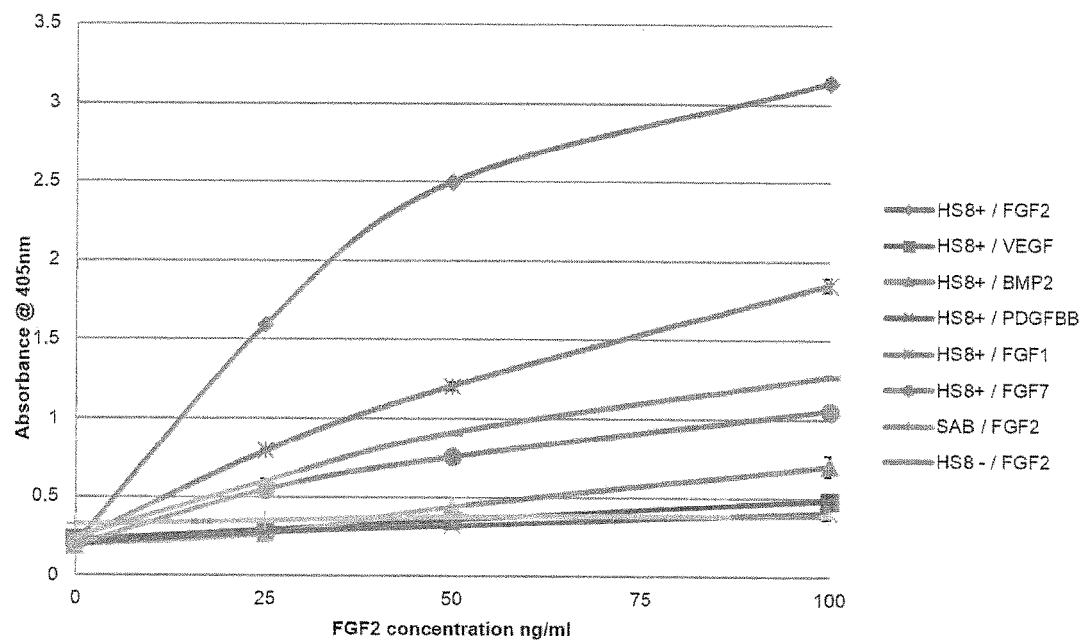
FIG. 8. Graphs showing (A) HS8 (HS8+) and (B) HS8 (−) binding to different proteins. (A) HS8+ 5 µg/ml with different proteins SAB/0.2% Fish Gelatin/22 ng/ml ExtrAvidin AP. (B) HS8(−) 5 µg/ml with different proteins SAB/0.2% Fish Gelatin/22 ng/ml ExtrAvidin AP.
Figure 8B:
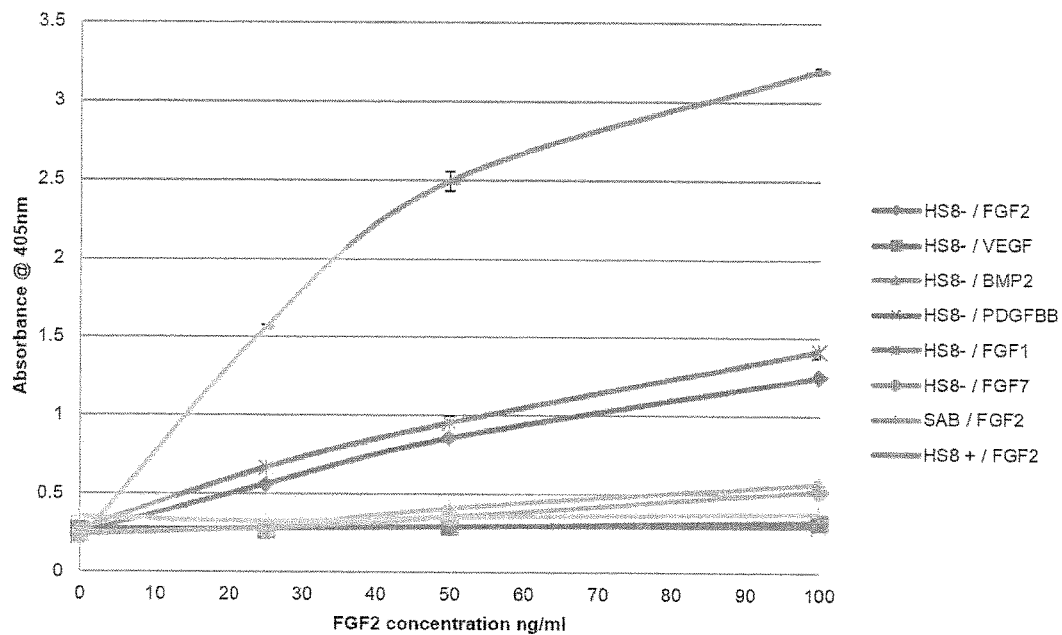

Then we tested the ability of HS8+ and HS8 (−) fractions binding to different proteins (FIG. 8). HS8+ has a higher affinity in binding to FGF2 compared to VEGF, BMP2, PDGFBB, FGF1, and FGF7 [FIG. 8(A)]. On the other hand, HS8 (−) fraction, has the most affinity in binding to FGF1 compared to the other proteins [FIG. 8(B)].

Ability of different GAGs competes with heparin with FGF2 tested in this assay, modified from Ono et al, 1999. A known concentration of FGF2 (R&D Systems) with differing concentrations of GAGs was mixed for 30 min at room temperature (RT) in a microtube.

To this 40 μl of beads solution [20 μl of heparin-agarose beads. (Type I, Sigma) and polyacrylamide gel (Bio-Gel P-30, Bio-Rad)] were added and mixed for 30 min at RT. The heparin beads were washed 3 times by centrifugation (2000 rpm for 1 minute) with BSA-PBS (1% BSA in PBS) and 3 times with PBST (PBS containing 0.02% Tween) and to each tube, 100 μl of 1:500 biotinylated anti-FGF2 (R&D Systems) added and incubated at RT for 1 hr. After washing as above, 100 μl of 1:10 TMB substrate (R&D Systems) was added and mixed for 30 min at RT. Stop solution (50 μl of 2N $H_2SO_4$) was added and 100 μl of the supernatant after centrifugation was transferred to a 96 well plate. The absorbance was read at 450 nm by Victor$^3$ 1420 multi label counter, Perkin Elmer.

Figure 9A:
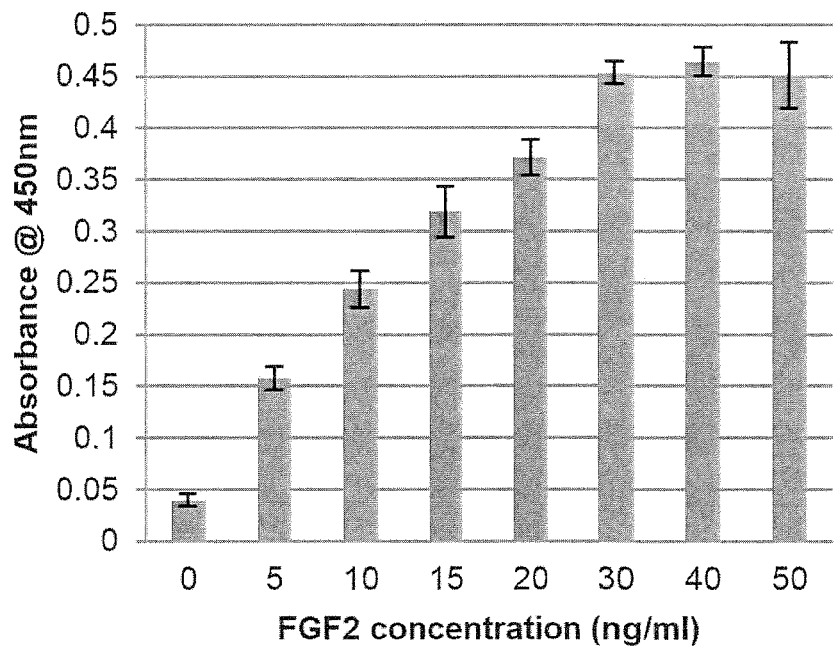
FIG. 9. Graphs showing results of heparin beads assay. (A) FGF2 optimization. (B) Heparin beads competition with exogenous heparin. (C) Percentage of competition of heparin beads with different GAGs.

Firstly, the amount of FGF2 needed for binding with the amount of heparin beads added was measured by the FGF2 optimization and the FGF2 dose 20 ng/ml were chosen for the next set of experiments [FIG. 9(A)].

Figure 9B:
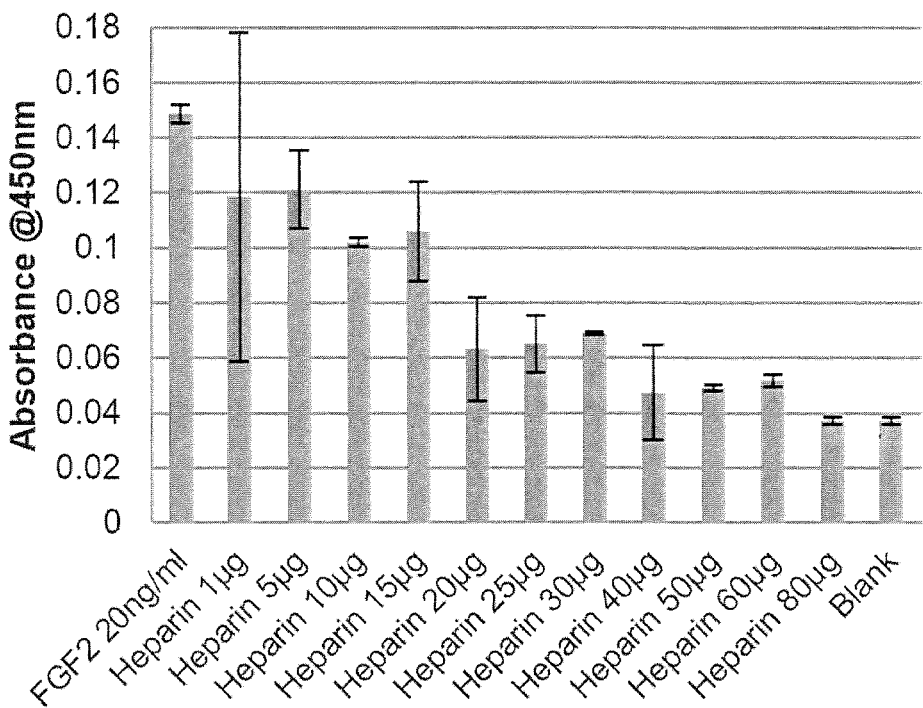
Figure 9C:
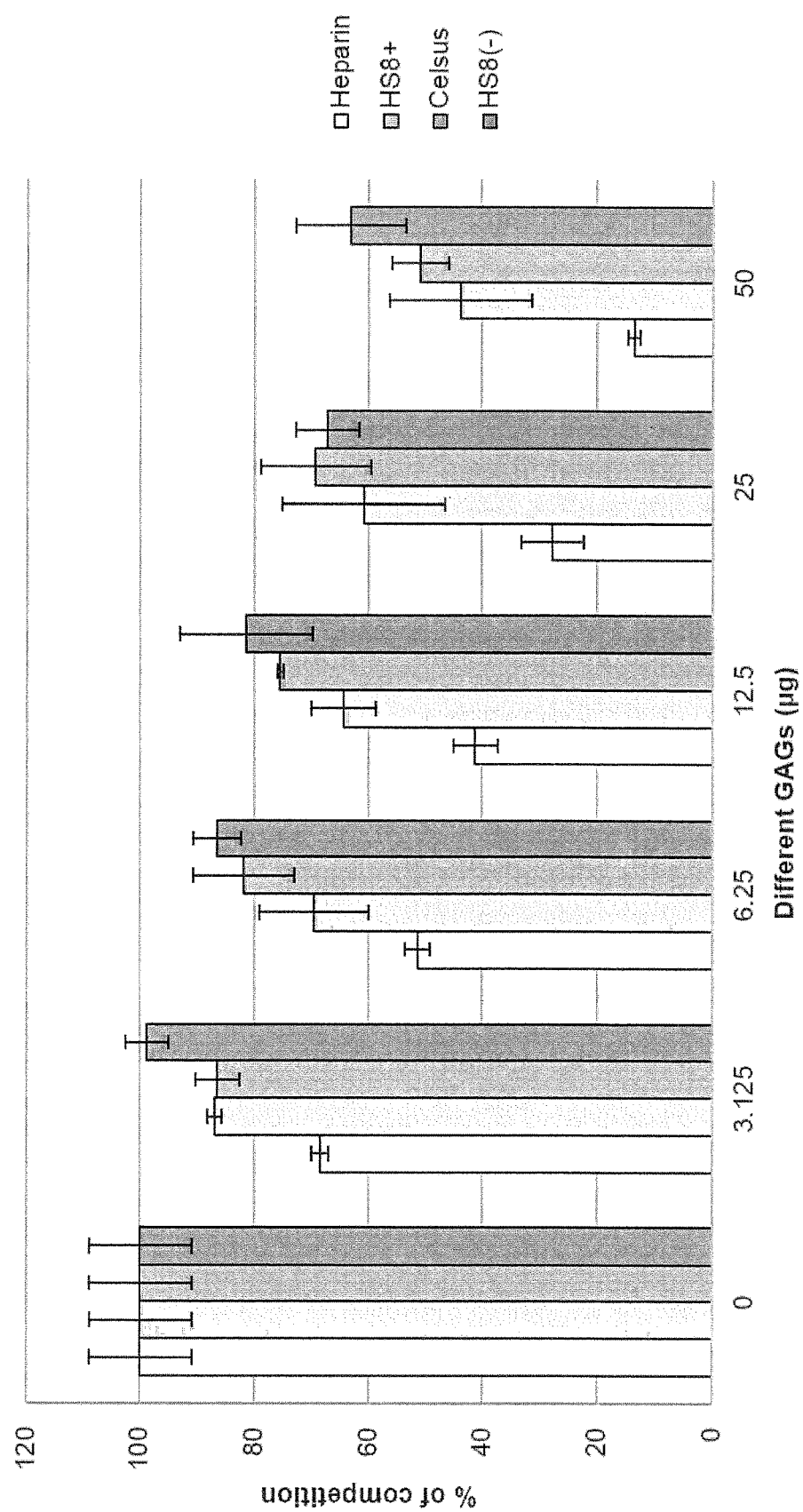

Then in order to get the range of GAGs to be used in the competition assay we initially used different amount of heparin. With the addition 50 μg of heparin was almost sufficient enough to compete with the internal heparin attached to the beads [FIG. 9(B)]. Hence, we used a range of 0-50 μg GAGS in the competition assay [FIG. 9(C)]. When considered the percentage of competition heparin was the most competitive where by adding 50 μg it reached around 13%, followed by HS8+ 43%, Celsus HS 50% and HS8(−) 63%.

Summary

We used the sequence $^{157}$GHFKDPKRLYCKNGGF$^{172}$ to prepare higher affinity binding HS (HS8) to FGF2 from Porcine Celsus HS by affinity chromatography.

In the glycosaminoglycan (GAG) binding assay results, which clearly showed that HS8+ had the highest affinity of binding to FGF2 compared to other GAG species. In addition the fold difference of Celsus HS: HS8+ at 100 ng/ml FGF2 point, the ratio was 1; 1.51. In heparin beads completion assays considering the percentage of competition, heparin was the most competitive where by adding 50 μg it reached around 13%, followed by HS8+ 43%, Celsus HS 50% and HS8(−) 63%. STRO1+hMSCs isolated by magnetic activated cell sorting and HM21 hMSCs isolated by conventional plastic adherence were used in cell proliferation assays, where higher cell counts were obtained when HS8+ used as a standalone media supplement at a concentration of 5 μg/ml and when the media change done in every 2 days. In conclusion, we now have successfully isolated higher binding affinity heparan sulfate (HS8) to FGF2 from a pool of commercially available heparan sulfate source which possess higher binding affinity to FGF2 and increase the ability to proliferate hMSCs.

In conclusion, we now have successfully isolated higher binding affinity heparan sulfate (HS8) to FGF2 from a pool of commercially available heparan sulfate source and shown that it has higher binding capacity compared with other GAGs including heparin. In addition, HS8+ when used as stand-alone media supplement increases the cell proliferation when media change done in every 2 days. Accordingly, we believe we have addressed the need for high quality ex vivo expanded MSCs by culturing these cells in a heparan sulphate (HS8) engineered to have high affinity for FGF2.

Additional Studies

Isolation of Specific HS (HS8) to FGF2

Although we have successfully achieved in isolating HS8, a higher binding affinity HS to FGF2 we would be further testing the other FGF2 HBD peptides sequences (table 1) in the means of [$^3$H] Heparin Assay, GAG binding assays and cell attachment assays according to Lee et al, 2007.

Binding Affinity Assays

The binding affinity of HS8 has already confirmed by GAG binding plates and will be further validated by dot blot assays and kinetic binding with BIAcore T100 (Cain et al, 2005).

Competition Assays

The results from ELISA method will be further confirmed by western blot method.

Disaccharide Analysis

Disaccharide analysis of HS8 will be carried out using anion exchange chromatography according to Murali et al, 2009 and the composition of the HS8 can be revealed.

Stability of FGF2

Stability assays will be carried out as SYPRO assays and FGF2 quantikine assays. In the SYPRO assay, interactions of FGF2 protein with GAGs will be measured as denaturing temperatures of proteins by a specific Sypro Orange dye (Uniewicz et al, 2010). The FGF2 quantikine assays will be carried out as with manufacturer's recommendations (R&D Systems Quantikine® ELISA Cat No. DFB50) in order to measure FGF2 concentrations in cell cultures. Results are shown in FIG. 28.

Example 3

The binding capacity of different GAGs for FGF2 was assessed using GAG-binding plates (Iduron). The binding capacity of different GAGs for the heparin-binding growth factors (HBGFs) BMP-2, FGF1, FGF2, FGF7, PDGF-BB and VEGF was also assessed using GAG-binding plates (Iduron). The materials and methodology used are described below.

Figure 10:
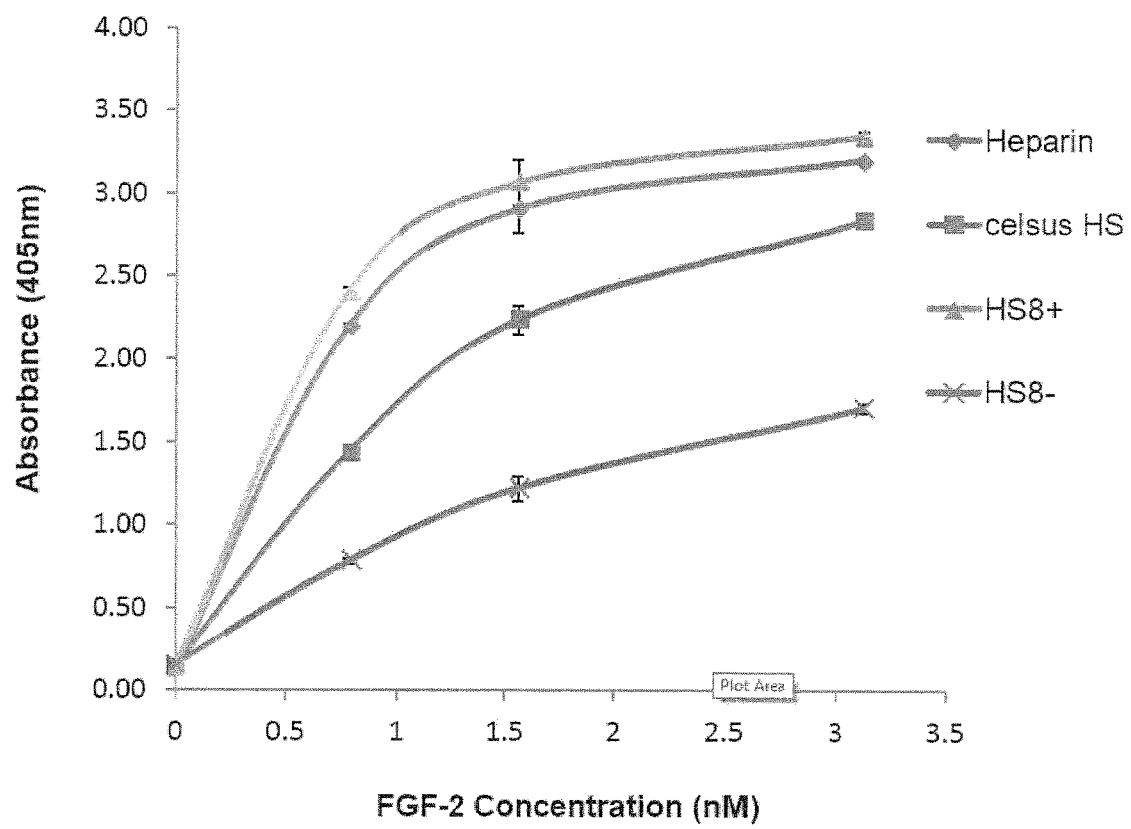
Figure 11A:
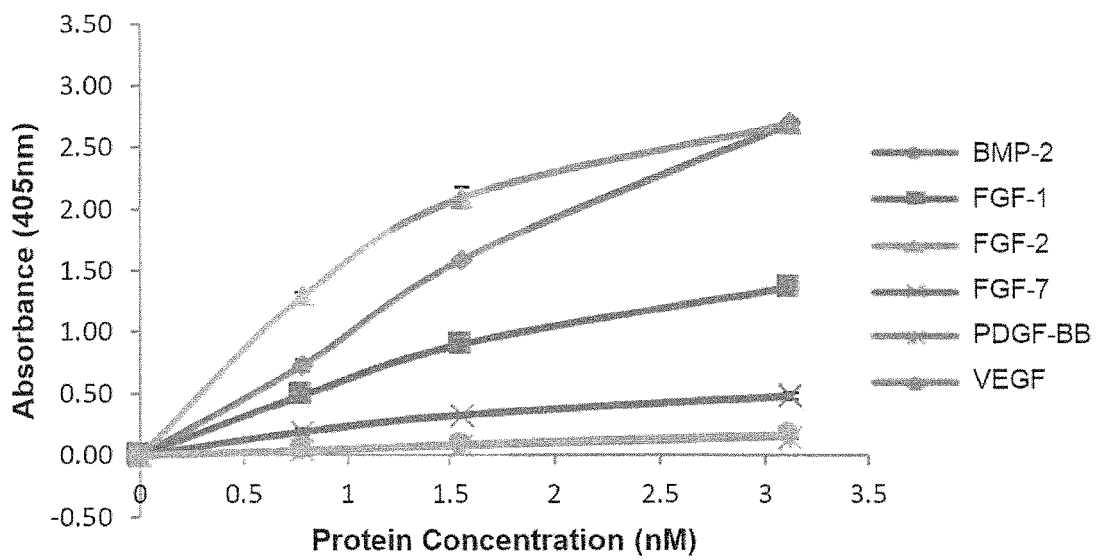
FIG. 11. Graphs showing binding capacity of different GAGs for heparin-binding growth factors (HBGFs) BMP-2, FGF1, FGF2, FGF7, PDGF-BB and VEGF, as assessed by GAG-binding plates (Iduron). (A) Celsus HS, (B) HS8, (C) HS8− fraction, (D) Heparin. The HS8 (HS8+) fraction preferentially binds FGF2 over all of the other HBGFs and even better heparin. HS8− and raw starting Celsus HS display little preference for any of the HBGFs.
Figure 11B:
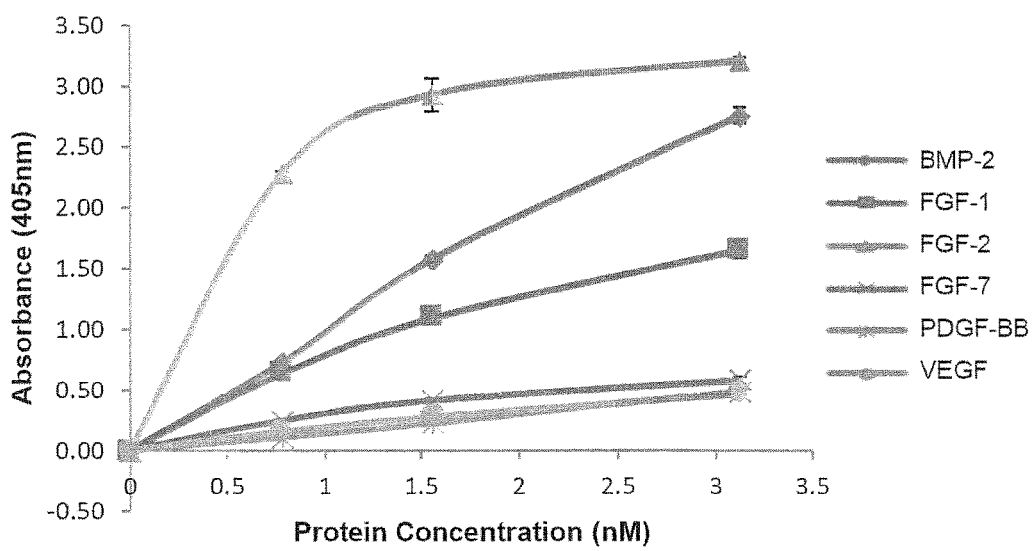
Figure 11C:
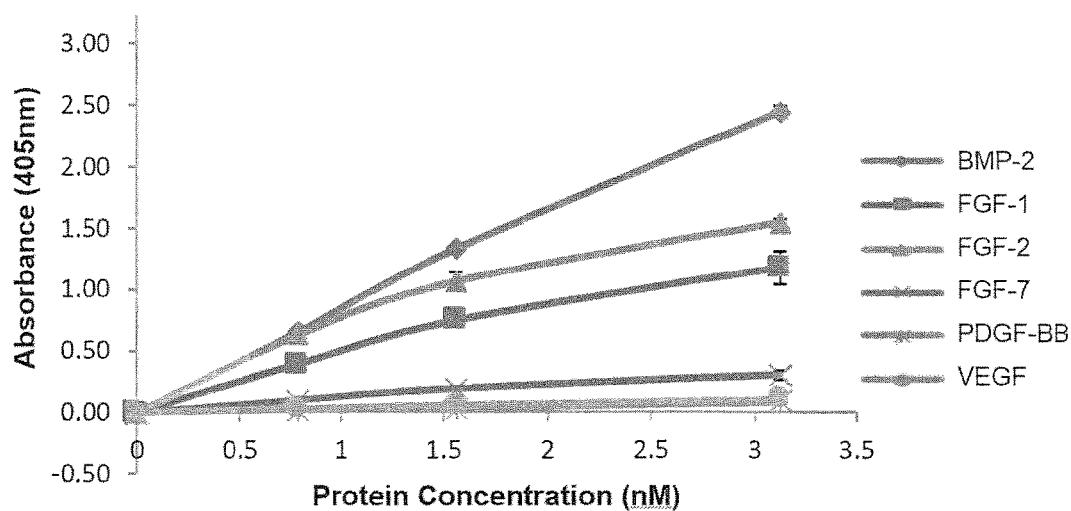
Figure 11D:
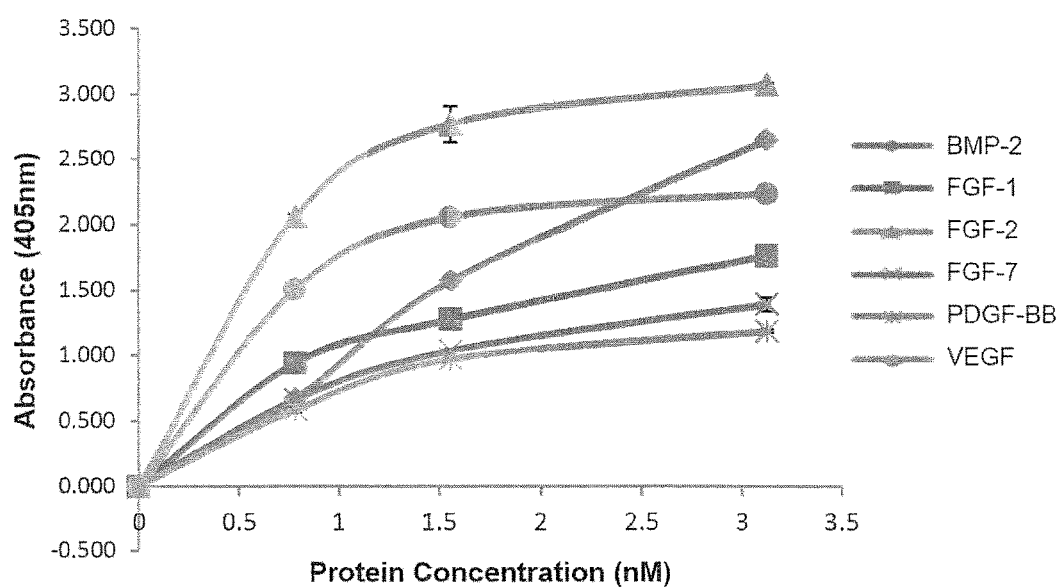

HS8 was found to bind FGF-2 almost as well as heparin, and certainly better than the raw starting Celsus HS and the HS8− flow through fraction (FIG. 10)

HS8 (HS8+) preferentially binds FGF2 over all the other HBGFs tested and has a higher binding capacity for FGF2 than heparin, i.e. HS8 exhibits specific binding to FGF2. HS8− and raw starting Celsus HS displayed little preference for any of the HBGFs tested (FIG. 11).

Materials
1. Standard Assay Buffer (SAB)—100 mM NaCl, 50 mM sodium acetate, 0.2% v/v tween 20, pH 7.2
2. Blocking buffer—0.4% Fish gelatin (Sigma Cat No. 67041)+SAB
3. GAG binding Plate (Iduron, UK)
4. Proteins from R& D Systems: BMP2—Cat No. 355 BM, FGF 1—Cat No. 231 BC, FGF 2-233 FB, FGF7—Cat No, 251 KG, PDGF BB—Cat No. 220 BB, VEGF—Cat No. 293 VE 5. Antibodies from R & D Systems: BMP2—Cat No. BAM 3552, FGF 1—Cat No. BAF232, FGF 2—BAM233, FGF7—Cat No. BAF251, PDGF BB—Cat No. BAF220, VEGF—Cat No. BAF 293
6. ExtraAvidin-AP (Sigma Cat No. E2636)
7. Sigma FAST p-Nitrophenyl phosphate (Sigma, N2770)

Method

1. Dissolve GAG in SAB (5 µg/ml)
2. Add 200 µl of GAG solution/well into GAG binding plate and incubate overnight at RT protected from light
3. Wash plate carefully 3× with 250 µl/well with SAB
4. Incubate plate with 250 µl/well blocking buffer for 1 hour at 37° C. protected from light
5. Wash plate carefully 3× with 250 µl/well with SAB
6. Dissolve proteins with blocking buffer and perform serial dilution: 0, 0.781, 1.56, 3.125 nM
7. Dispense 200 µl/well of diluted protein to GAG coated plate and incubate for 2 hours at 37° C.
8. Wash plate carefully 3× with 250 µl/well with SAB
9. Add 200 µl/well of 250 ng/ml of biotinylated primary antibody in blocking solution and incubate for 1 hour at 37° C.
10. Wash plate carefully 3× with 250 µl/well with SAB
11. Add 200 µl/well of 220 ng/ml of ExtraAvidin-AP in blocking solution and incubate for 30 min at 37° C.
12. Wash plate carefully 3× with 250 µl/well with SAB
13. Add 200 µl/well of Development reagent: Sigma FAST p-Nitrophenyl phosphate in DI water and incubate for 40 min at RT
14. Read absorbance at 405 nm Example 4

NMR Analysis of HS8

A sample of HS8 was stored at −20° C. prior to analysis. NMR analysis was completed by dissolution in D2O (600 uL) that contained the internal standard tBuOH (200 µL, δ1.24 ppm) that is used for chemical shift comparison and quantitation. Celsus HS was weighed accurately in ~1, 4 and 7 mg amounts, made up in the working D2O/tBuOH solution and analysed in the same run as HS8. Line fitting of the standard solutions gave regression of 0.995 or better for integration of the acetyl methyl region, the region δ 3.15-3.25 ppm and the lowest field portion of the anomeric region δ 5.15-5.65 ppm compared to the internal standard.

Due to the small sample size which results in low signal to noise only the acetyl region data was used to calculate the amount of HS8 delivering a value of 0.7 mg. A second experiment was completed comparing signal to noise of the acetyl peak and a value of 0.5 mg was recorded. This is an absolute value not related to the internal standard. After three freeze-dry steps to remove the tBuOH prior to further analysis the mass recorded was 1.2 mg. Of note is the SEC HPLC data can be integrated to give an approximate purity value and it also recorded 58% suggesting 0.7 mg of HS-GAG present in the material. As this weight discrepancy is not a new phenomenon in small GAG samples the assumption is made that varying humidity and a proportion of salt must be affecting the recorded mass.

Figure 15:
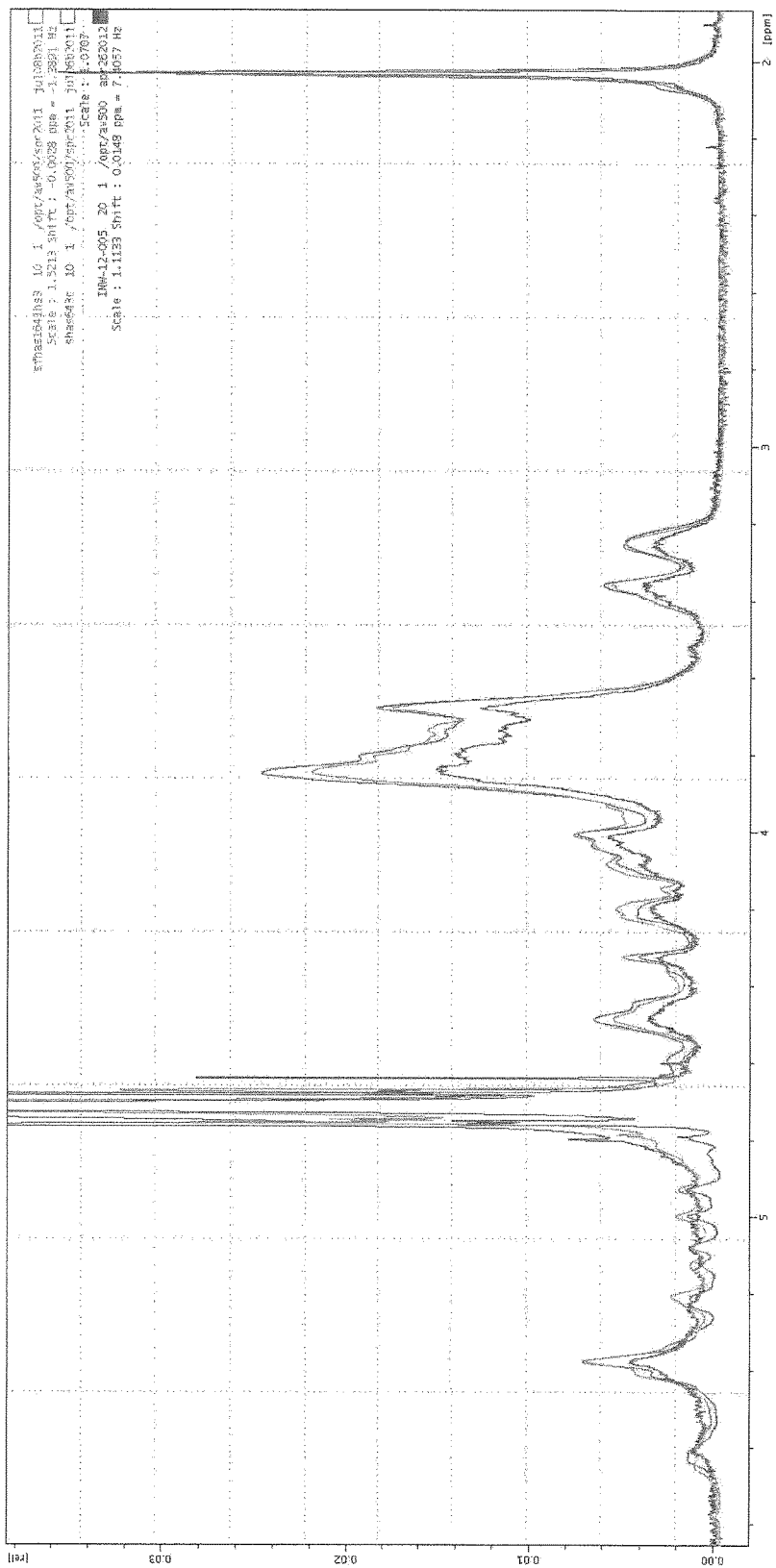
FIG. 15. $1^H$ NMR of Celsus HS, HS8 and HS3 (D$_2$O solutions).

The 1H NMR spectrum of HS8, Celsus HS and HS3* is displayed in FIG. 15. The difference in intensity of the HS8 (lowest peak at 4.8-4.6 ppm) compared to other signals (Celsus HS is the highest peak at 4.8-4.9 and HS3 is the intermediate height peak) in the displayed plot is due to normalising all spectra to the height of the acetyl methyl resonance: in the case of this HS8 sample a slightly better shimming was observed with narrower line width causing the acetyl resonance to be slightly sharper and taller.

The chemical composition change of HS8 compared to Celsus HS is just differentiated by 2-D NMR.

Figure 16:
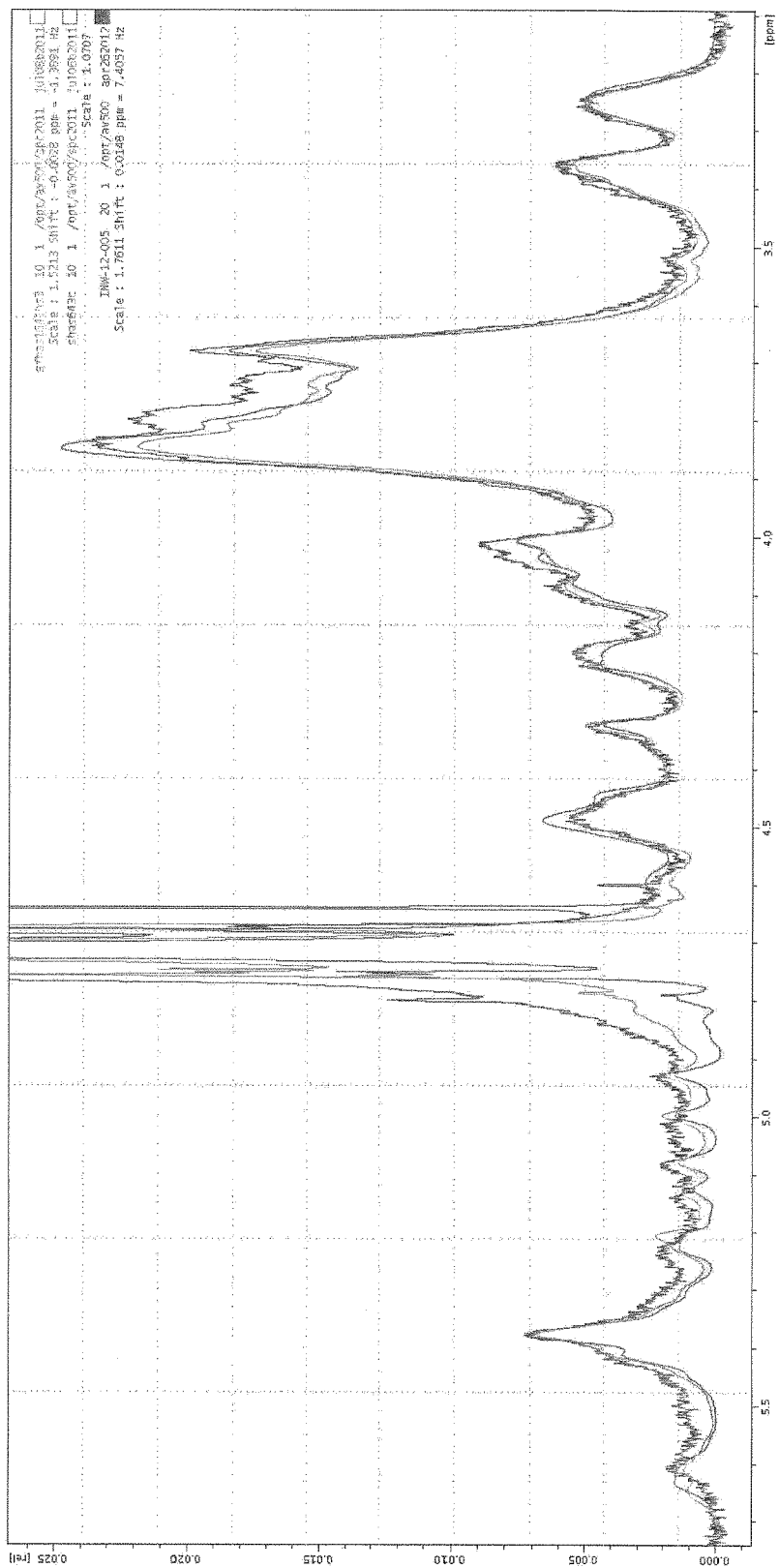
FIG. 16. Close-up of $1^H$ NMR of Celsus HS, HS8 and HS3 (D$_2$O solutions).

Closer examination of the methine and methylene regions of the HS8 1H NMR showed differences compared to Celsus HS and HS3 (FIG. 16).

[*HS3 is an isolated heparan sulphate having specific and high binding affinity for a heparan binding domain of BMP-2. HS3 is described in WO2010/030244]

Example 5

HPLC-SEC-RI of HS8 and Other HS Preparations

Heparan sulfate preparations (approximately 1 mg, weighed accurately) were made up to 2 mg/mL in water. Heparin lyase I, II and III digests of these preparations were 2 mg/mL in water. The solutions were centrifuged (14 000 g, 2 min) and 200 µL aliquots were taken for analysis.

The SEC-RI system consists of a Waters 2690 Alliance separations module and a Water 2410 refractive index monitor (range 64). The dn/dc for quantitation from the RI chromatograms was set at 0.129 (ref). Samples were injected (50 µL) and eluted with 50 mM ammonium acetate with a flow rate of 0.5 mL/min from two Superdex™ Peptide 10/300 GL columns in series (300×10 mm GE Healthcare, Buckinghamshire, UK). Data was collected and analysed using ASTRA software (Version 4.73.04, Wyatt Technology Corp).

Figure 17:
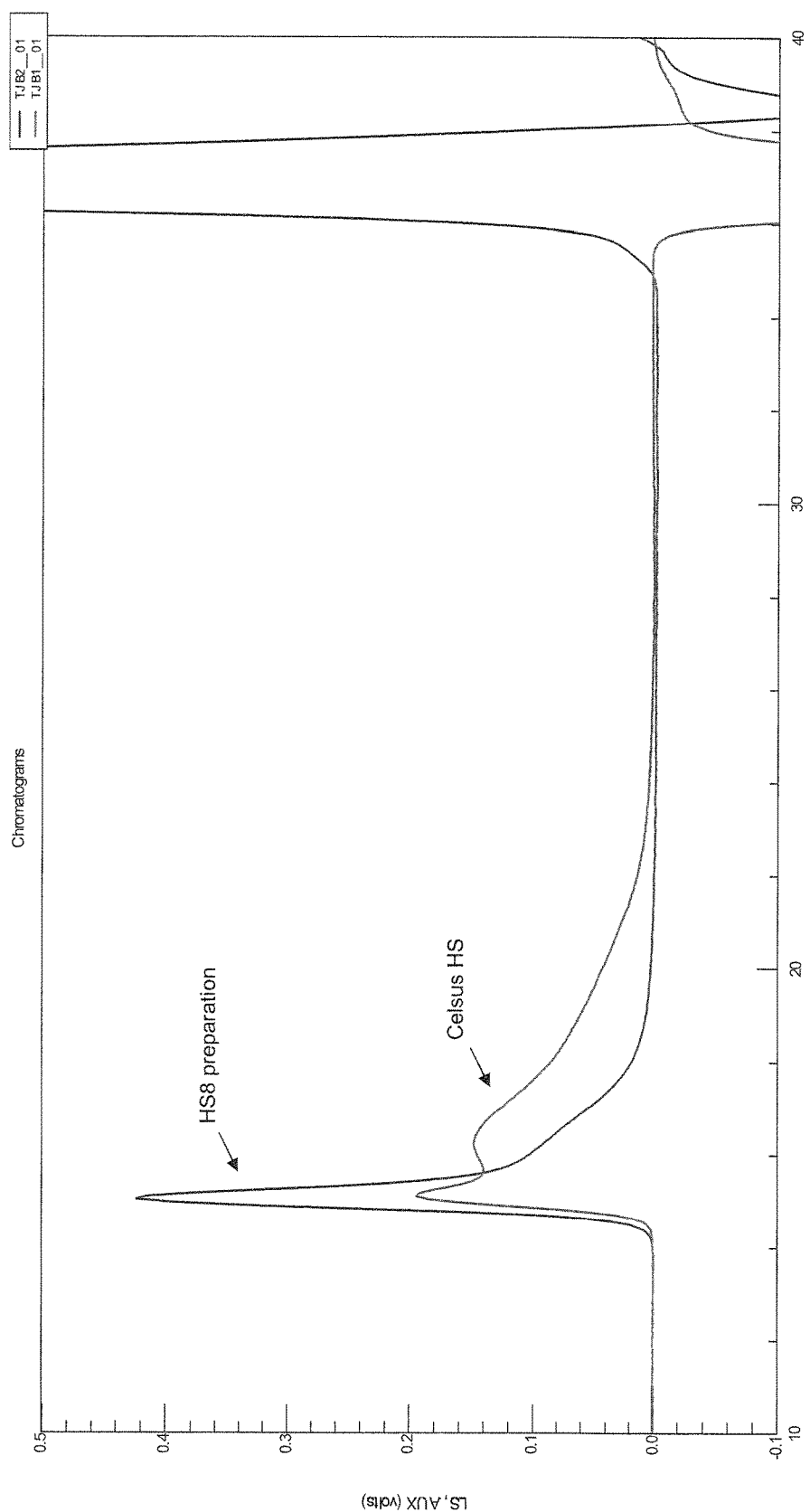
FIG. 17. HPLC-SEC-RI chromatograms of Celsus HS #10697 and HS8, separated on 2× Superdex Peptide columns eluted with 50 mM ammonium acetate.

The size-exclusion chromatography of the whole HS8 preparation displayed a distinct size-exclusion profile. The Celsus HS starting material shows a voiding signal at 15 mL with additional material of a range of sizes eluting to approximately 23 mL of eluent. As shown in FIG. 17 the HS8 material (retained by the FGF-2 affinity column) shows a size profile enriched in the material that voids the SEC columns.

Figure 18:
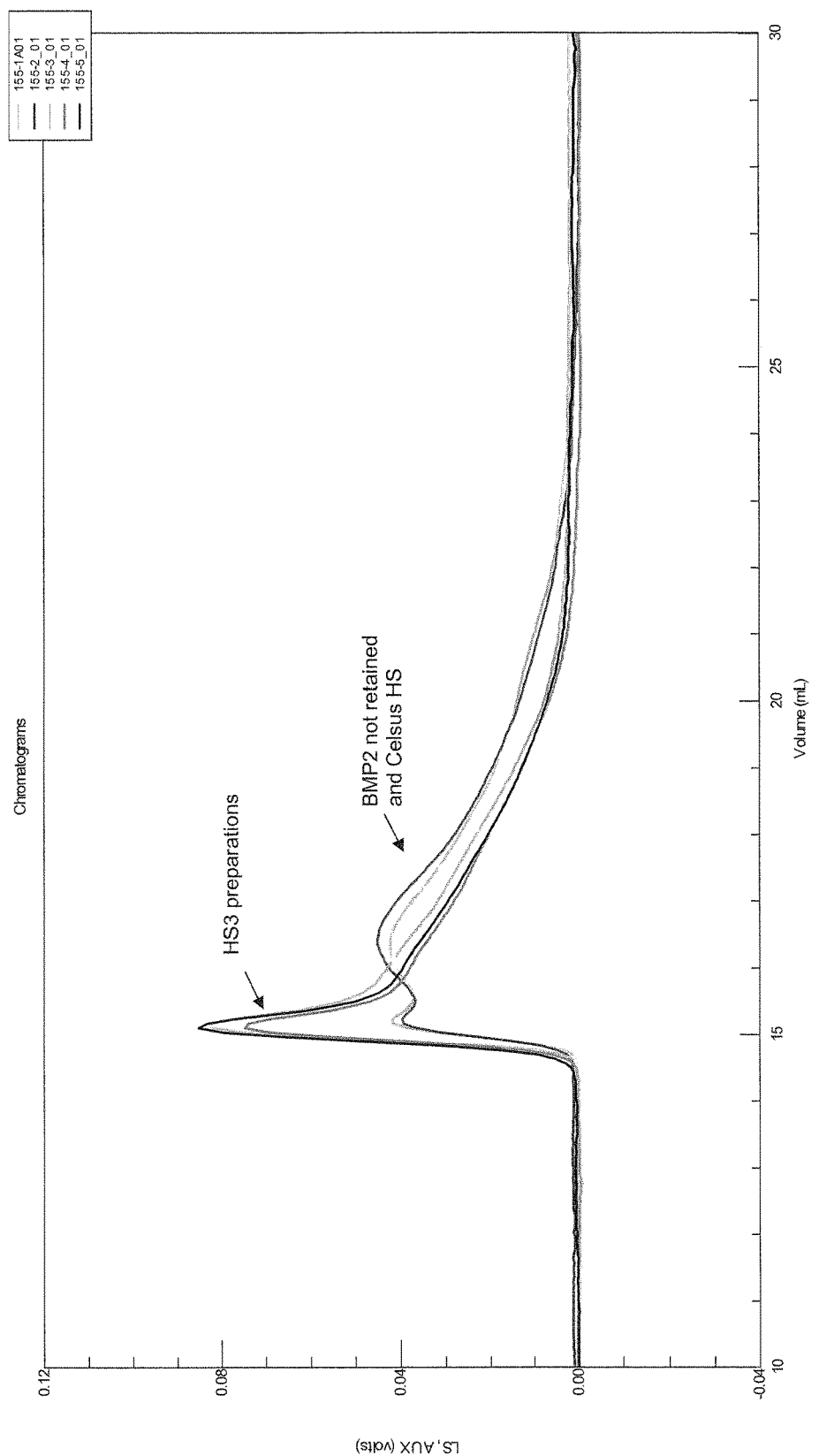
FIG. 18. HPLC-SEC-RI chromatograms of heparan sulfate: Celsus HS #10697; BMP2 not retained (848/HS3/001); BMP2 retained (HS3) (848/HS3/001); Initial run (HS3-001-01); Final run (HS3-001-02). The HS3 preparations show a high peak (0.06-0.08) at about 15 ml.

This is distinct again from the size profile of the HS3 preparations, showing an intermediate size profile between the HS8 and Celsus HS profiles (FIG. 18). The HS8 chromatogram shows a large salt signal at approximately 36 mL as this sample was prepared in 50 mM sodium acetate buffer (pH 7) rather than water.

Figure 19:
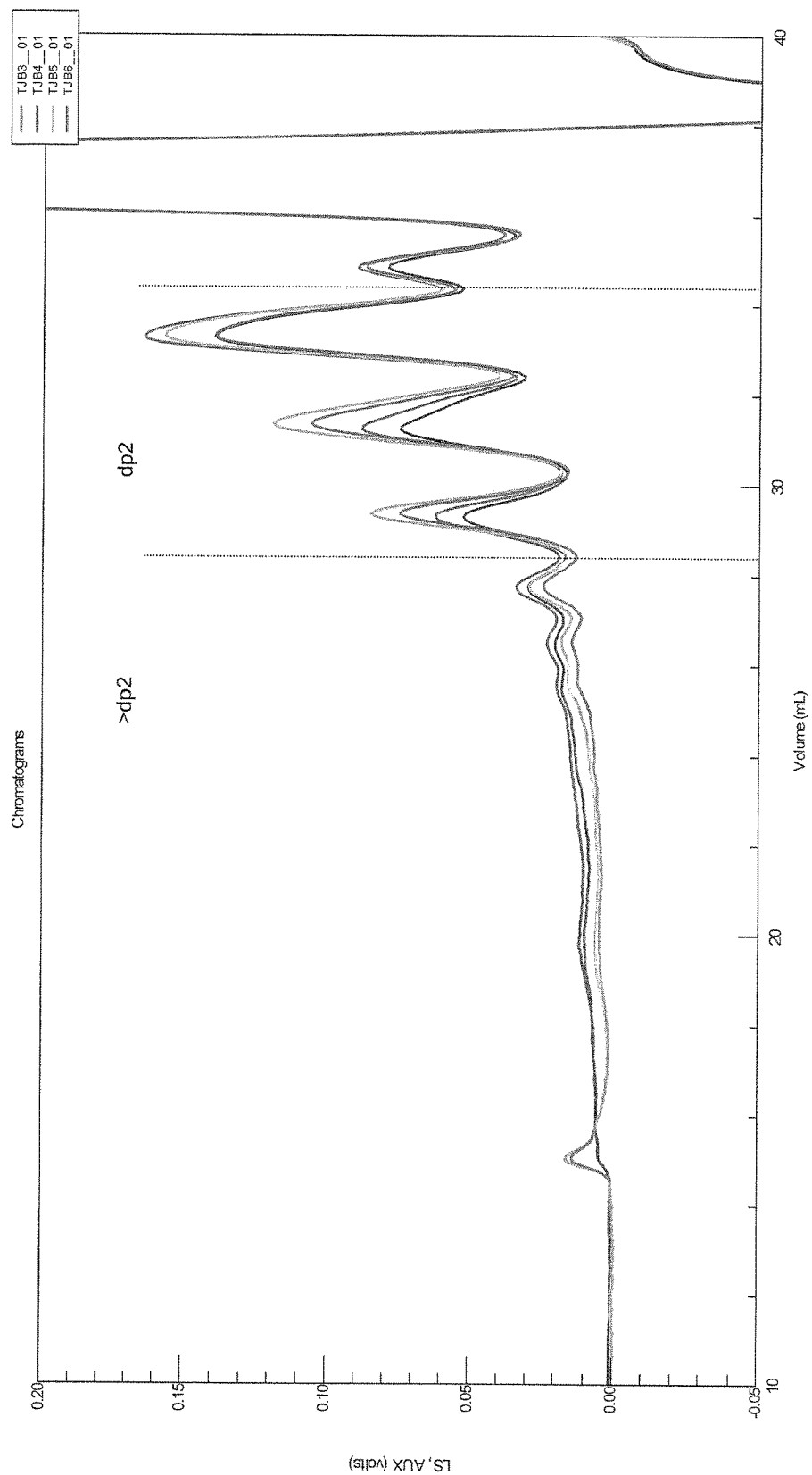
FIG. 19. HPLC-SEC-RI of heparin lyase I, II and III digests of HS preparations HS #10697 and HS #10595 from Celsus. Heparin lyase digests were done in duplicate. Vertical line indicates the cut off for the elution of disaccharides and oligosaccharides with a degree of polymerisation (dp) larger than 2.

FIG. 19 shows the SEC chromatograms for two different batches of the HS from Celsus. Batch #10697 was used as the starting material for the preparation of both HS3 and HS8. The digestion of both of these batches with the enzymes is similar except that batch #10595 appears to have a larger amount of material that is not digested at all and voids the columns.

Figure 20:
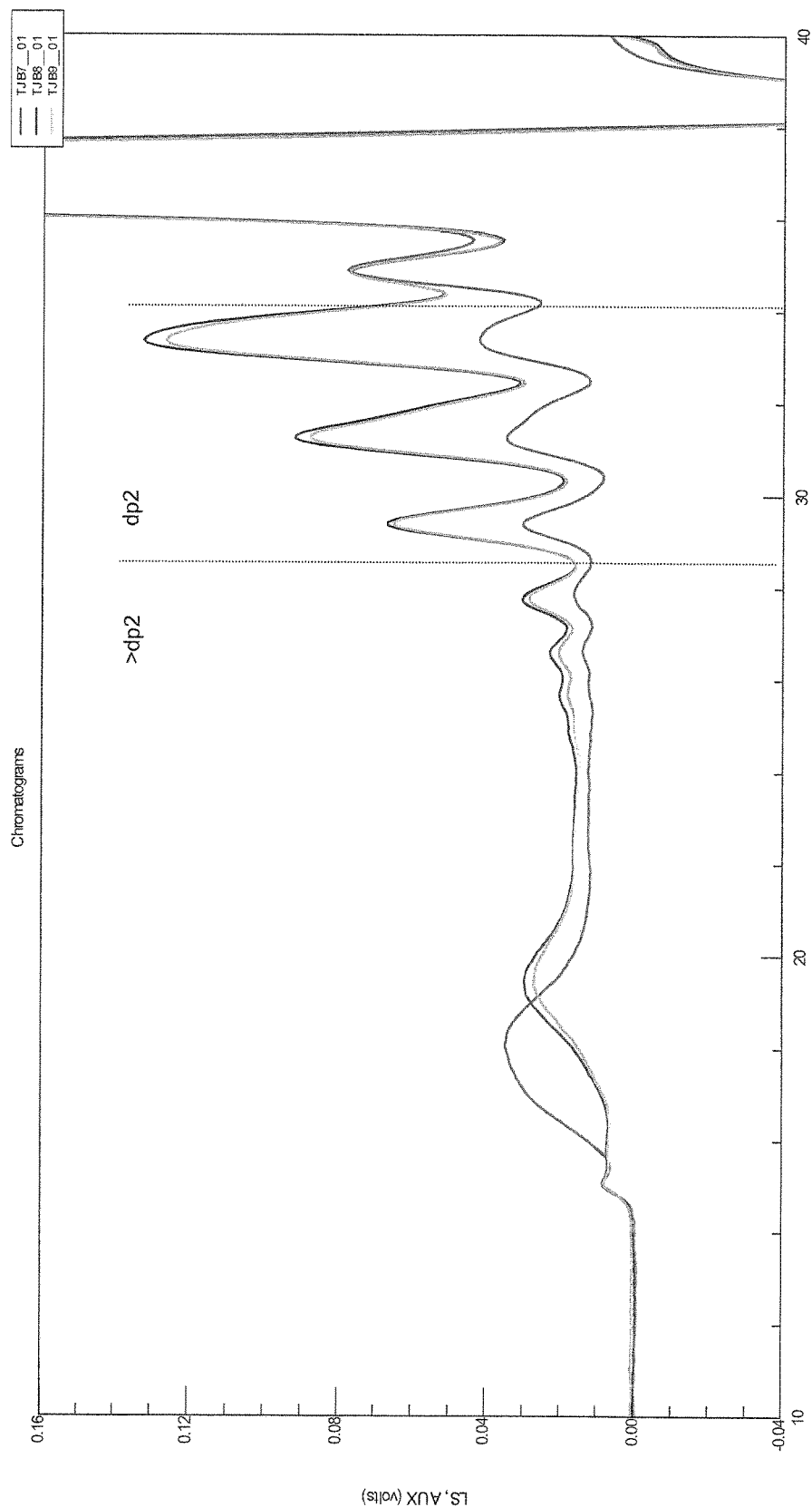
FIG. 20. HPLC-SEC-RI chromatograms of HS8 (broad peak at 18-20 ml), HS3-001-01 (peak at 19-20 ml), on 2× Superdex Peptide columns, eluted with 50 mM ammonium acetate.

The size profile of the heparin lyase digest of HS8 (FIG. 20) is quite different from that of the Celsus HS starting material (FIG. 19) or HS3 (FIG. 20). The size profile obtained for HS3 was very similar to that obtained in previous digests. The HS8 chromatogram, like that for the HS3 digests, shows little signal strength at the void volume (15 mL), suggesting that most of the material is digested to some extent. However, the two HS3 digests show significant and distinct signal strength at approximately 19 mL, whereas the HS8 shows a broad signal around 18 mL.

Example 6

3H Heparin Assay

Figure 21:
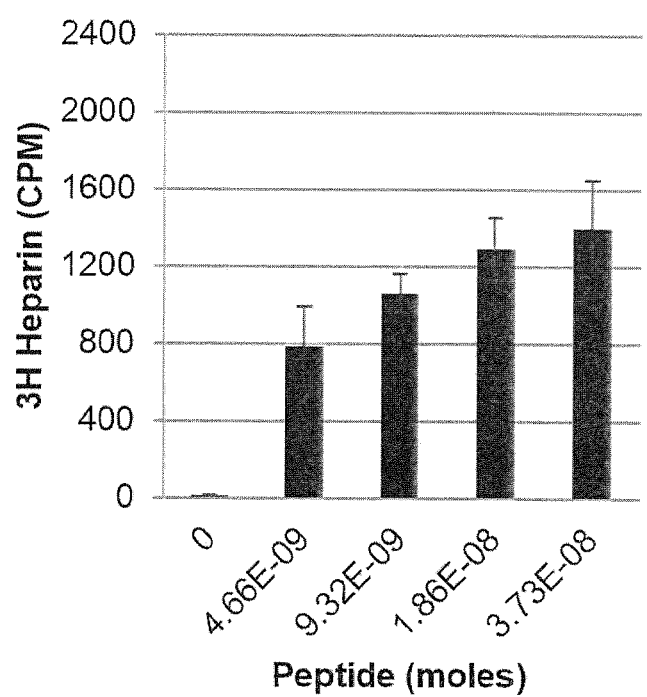
FIG. 21. Graphs showing heparin binding SEQ ID NO:1.

The heparin binding ability of SEQ ID NO:1 derived from the amino acid sequence of FGF2 was assessed using the protocol described below. Results are shown in FIG. 21.

Materials (1) Peptides:

Gandhi et al (HS8)—Manufactured by Nanyang Technological University GHFKDPKRLYCKNGGF-Ahx-(K)Biotin (2) 3H Heparin 0.1 µCi (Perkin Elmer, Boston, USA)
(3) Nitrocellulose Membrane (Bio-Rad, USA)
(4) Bovine Serum Albumin 4% (w/v) in PBS
(5) Vacuum Oven (Thermo Fisher Scientific, USA)
(6) Tri-Carb 2800 TCR Liquid Scintillation Analyzer (Perkin Elmer, Boston, USA)

Methods (1) Make up FGF2-HBD-peptides to desired concentrations ($4.66 \times 10^{-9}$, $9.32 \times 10^{-9}$, $1.86 \times 10^{-8}$, $3.73 \times 10^{-8}$ moles) with PBS
(2) Soak identical nitrocellulose membranes in duplicates with known concentrations of peptides
(3) Air dry the membranes for 1 h
(4) Further drying in vacuum oven at 800 C for 45 mins
(5) Wash membranes 3 times with PBS
(6) Add 3H Heparin 0.1 µCi to the membranes and incubate for 16 h in scintillation counting vials
(7) Wash membranes 4 times with PBS
(8) Determine radioactivity with Tri-Carb 2800 TCR Liquid Scintillation Analyzer (Perkin Elmer, Boston, USA)

Example 7

Figure 22:
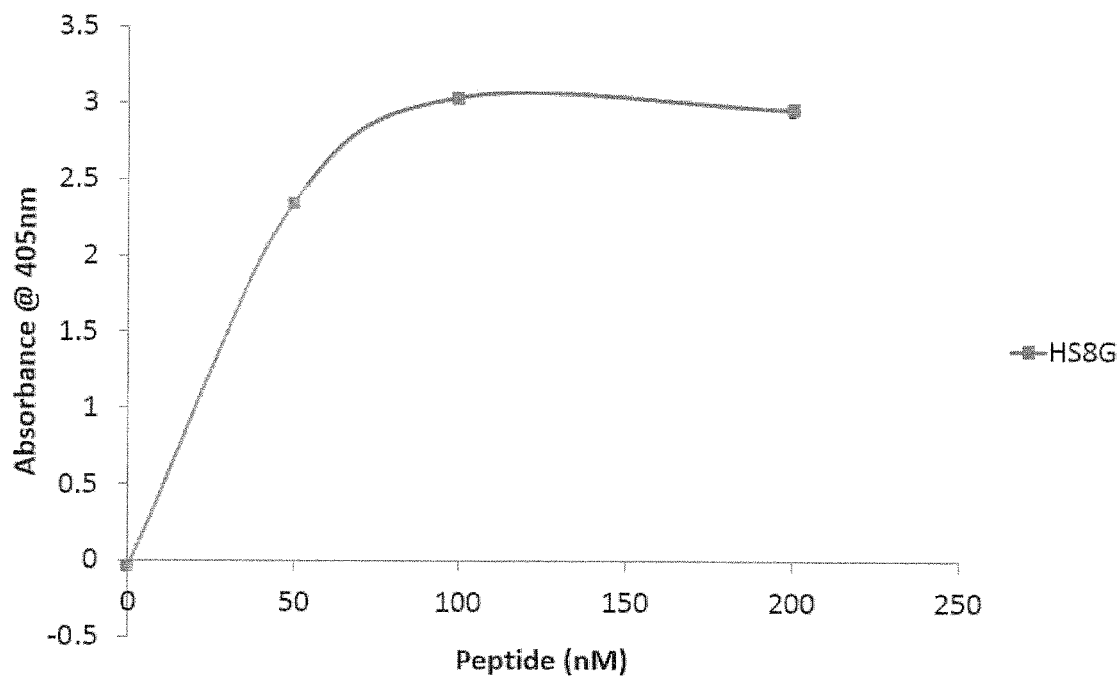
FIG. 22. Graph showing ability of heparin binding domain peptide G derived from the amino acid sequence of FGF2 to bind immobilised heparin.

The ability of heparin binding domain peptide SEQ ID NO:1 to bind immobilized heparin was assessed using the protocol described below. Results are shown in FIG. 22.

Materials

1. Standard Assay Buffer (SAB)—100 mM NaCl, 50 mM sodium acetate, 0.2% v/v tween 20, pH 7.2
2. Blocking buffer—0.4% Fish gelatin (Sigma Cat No. 67041)+SAB
3. GAG binding Plate (Iduron, UK)
4. Peptides:

Gandhi et al (HS8)—Manufactured by Nanyang Technological University GHFKDPKRLYCKNGGF-Ahx-(K)Biotin 5. ExtraAvidin-AP (Sigma Cat No. E2636)
6. Sigma FAST p-Nitrophenyl phosphate (Sigma, N2770)

Method

1. Dissolve Heparin in SAB (5 µg/ml)
2. Add 200 µl of Heparin solution/well into GAG binding plate and incubate overnight at RT protected from light
3. Wash plate carefully 3× with 250 µl/well with SAB
4. Incubate plate with 250 µl/well blocking buffer for 1 hour at 37° C. protected from light
5. Wash plate carefully 3× with 250 µl/well with SAB
6. Dissolve peptides in blocking buffer and perform serial dilution: 0, 50, 100, 200 nM
7. Dispense 200 µl/well of diluted protein to GAG coated plate and incubate for 2 hours at 37° C.
8. Wash plate carefully 3× with 250 µl/well with SAB
9. Add 200 µl/well of 220 ng/ml of ExtraAvidin-AP in blocking solution and incubate for 30 min at 37° C.
10. Wash plate carefully 3× with 250 µl/well with SAB
11. Add 200 µl/well of Development reagent: Sigma FAST p-Nitrophenyl phosphate in DI water and incubate for 40 min at RT
12. Read absorbance at 405 nm Example 8

Figure 23:
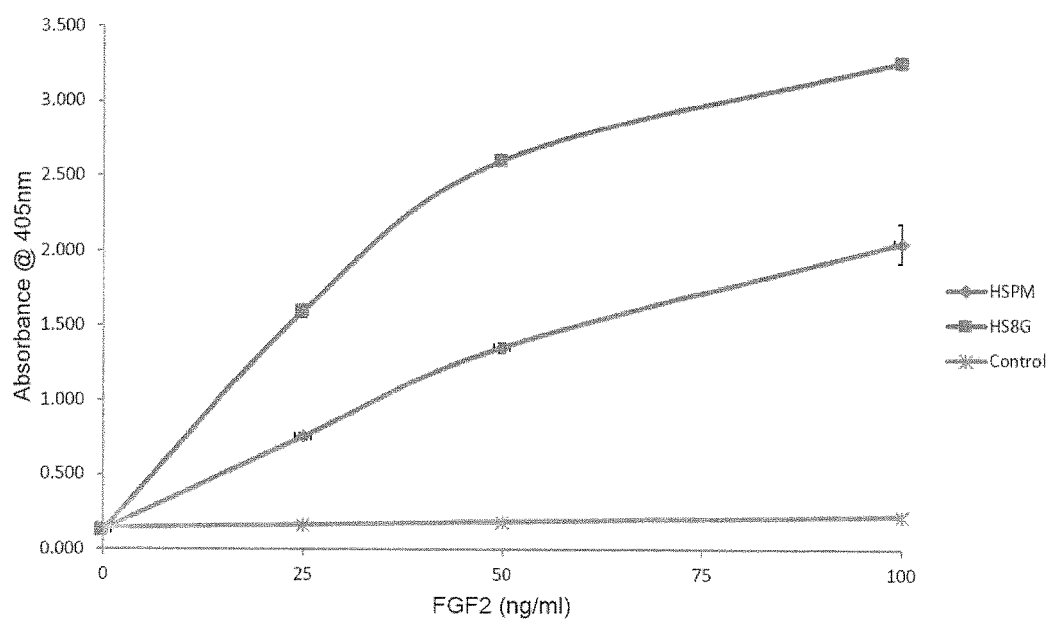
FIG. 23. Graph showing ability of FGF-2 to bind HS8 purified by affinity chromatography (column derivatized with SEQ ID NO:1). This was compared to binding with the raw starting HS (HS-PM porcine mucosa), or a no sugar control.

FGF-2 was assessed for its ability to bind HS8. This was compared to binding with the raw starting HS (HS-PM porcine mucosa), or no sugar. Results are shown in FIG. 23.

Materials

1. Standard Assay Buffer (SAB)—100 mM NaCl, 50 mM sodium acetate, 0.2% v/v tween 20, pH 7.2
2. Blocking buffer—0.4% Fish gelatin (Sigma Cat No. 67041)+SAB
3. GAG binding Plate (Iduron, UK)
4. Proteins from R& D Systems: FGF 2—233 FB
5. Antibodies from R & D Systems: FGF 2—BAM233
6. ExtraAvidin-AP (Sigma Cat No. E2636)
7. Sigma FAST p-Nitrophenyl phosphate (Sigma, N2770)

Method

1. Dissolve GAG in SAB (5 µg/ml)
2. Add 200 µl of GAG solution/well into GAG binding plate and incubate overnight at RT protected from light
3. Wash plate carefully 3× with 250 µl/well with SAB
4. Incubate plate with 250 µl/well blocking buffer for 1 hour at 37° C. protected from light
5. Wash plate carefully 3× with 250 µl/well with SAB
6. Dissolve proteins with blocking buffer and perform serial dilution: 0, 0.781, 1.56, 3.125 nM
7. Dispense 200 µl/well of diluted protein to GAG coated plate and incubate for 2 hours at 37° C.
8. Wash plate carefully 3× with 250 µl/well with SAB
9. Add 200 µl/well of 250 ng/ml of biotinylated primary antibody in blocking solution and incubate for 1 hour at 37° C.
10. Wash plate carefully 3× with 250 µl/well with SAB
11. Add 200 µl/well of 220 ng/ml of ExtraAvidin-AP in blocking solution and incubate for 30 min at 37° C.
12. Wash plate carefully 3× with 250 µl/well with SAB
13. Add 200 µl/well of Development reagent: Sigma FAST p-Nitrophenyl phosphate in DI water and incubate for 40 min at RT
14. Read absorbance at 405 nm Example 9

Capillary Electrophoresis (CE) Analysis of Disaccharides

Heparan sulfate (HS) was from Celsus Laboratories Inc. (HO-03103, Lot #HO-10697). Disaccharide standards (ΔUA,2S-GlcNS,6S; ΔUA,2S-GlcNS, ΔUA,2S-GlcNAc,6S, ΔUA-GlcNS,6S, ΔUA-GlcNS, UA-GlcNAc, ΔUA,2S-GlcNAc, ΔUA-GlcNAc,6S, ΔUA,2S-GlcN, ΔUA,2S-GlcN,6S, ΔUA-GlcN,6S, ΔUA-GlcN Cat No. HD001 to HD013, Iduron Ltd, Manchester, UK), derived from the digestion of high-grade porcine heparin by bacterial heparinases, were purchased from Iduron Ltd, Manchester, UK. A synthetic derivative of a not naturally occurring disulfated disaccharide (ΔUA,2S-GlcNCOEL6S), was also purchased from Iduron for use as an internal standard. Heparin Oligosaccharides (dp4, dp6, dp8, dp10, dp12 (Cat. No. HO04, HO06, HO08, HO10, HO12)) and selectively desulfated heparin standards (2-O, 6-O and N-desulfated heparin) (Cat No. DSH001/2, DSH002/6, DSH003/N, Iduron Ltd, Manchester, UK) were also purchased from Iduron Ltd, Manchester, UK.

Heparin lyase I (Heparitinase, EC 4.2.2.8, also known as heparitinase I), heparin lyase II (heparitinase II, no EC number assigned) and heparin lyase III (heparinase, EC 4.2.2.7, also known as heparitinase III) were obtained from Seikagaku Corporation, Japan. The enzymes, supplied as lyophilised powders (0.1 U/vial), were dissolved in 0.1% BSA to give solutions containing 0.5 mU/µL. Aliquots (5 µL; 2.5 mU) were frozen (−80° C.) until needed.

Digestion of HS Preparations with Heparin Lyase Enzymes

HS preparations (1 mg) were each dissolved in 500 µL of sodium acetate buffer (100 mM containing 10 mM calcium acetate, pH 7.0) and 2.5 mU each of the three enzymes was added. The samples were incubated at 37° C. overnight (24 h) with gentle inversion (9 rpm) of the tubes. A further 2.5 mU each of the three enzymes was added to the samples which were incubated at 37° C. for a further 48 h with gentle inversion (9 rpm) of the tubes. Digests were halted by heating (100° C., 5 min) and then lyophilized. The digests were resuspended in 500 µL water and an aliquot (50 µL) was taken for analysis by CE.

Capillary Electrophoresis (CE)

The capillary electrophoresis operating buffer was made by adding an aqueous solution of 20 mM $H_3PO_4$ to a solution of 20 mM $Na_2HPO_4.12H_2O$ to give pH 3.5. The column wash was 100 mM NaOH (diluted from 50% w/w NaOH). The operating buffer and column wash were both filtered using a Millipore filter unit fitted with 0.2 µm cellulose acetate membrane filters (47 mm ø; Schleicher and Schuell, Dassel, Germany). Stock solutions of the 12 disaccharide standards were prepared by dissolving the disaccharides in water (1 mg/mL). To determine the calibration curves for the standards, a mix containing all twelve standards was prepared. The stock solution of the 12 standard mix contained 10 µg/100 µL of each disaccharide and a dilution series containing 10, 5, 2.5, 1.25, 0.625, 0.3125 µg/100 µL was prepared; including 2.5 µg of internal standard (ΔUA,2S-GlcNCOEL6S). The digests of HS were diluted (50 µL/mL) with water and the same internal standard was added (2.5 µg) to each sample. The solutions were freeze-dried and re-suspended in water (1 mL). The samples were filtered using PTFE hydrophilic disposable syringe filter units (0.2 µm; 13 mm ø; Advantec, Toyo Roshi Kaisha, Ltd., Japan).

The analyses were performed using an Agilent$^{3D}$CE (Agilent Technologies, Waldbronn, Germany) instrument on an uncoated fused silica capillary tube (75 µm ID, 64.5 cm total and 56 cm effective length, Polymicro Technologies, Phoenix, Ariz., Part Number TSP075375) at 25° C. using 20 mM operating buffer with a capillary voltage of 30 kV. The samples were introduced to the capillary tube using hydrodynamic injection (50 mbar×12 sec) at the cathodic (reverse polarity) end.

Before each run, the capillary was flushed with 100 mM NaOH (2 min), with water (2 min) and pre-conditioned with operating buffer (5 min). A buffer replenishment system replaced the buffer in the inlet and outlet tubes to ensure consistent volumes, pH and ionic strength were maintained. Water only blanks were run at both the beginning, middle and end of the sample sequence. Absorbance was monitored at 232 nm. All data was stored in a ChemStore database and was subsequently retrieved and re-processed using ChemStation software.

Eleven of the 12 heparin disaccharides in the standard mix were separated using conditions detailed above. The 12th disaccharide, ΔUA-GlcN, does not migrate under the conditions used for these experiments. However, this disaccharide has not been reported to occur in heparan sulfates. The $R^2$ values for the standard calibration curves ranged from 0.9949 to 1.0.

The heparin lyase I, II and III digest of the HS preparations was done in duplicate and each duplicate was injected twice in the CE. Therefore, the normalized percentage of the disaccharides in the HS digest is the mean average of the results for the analyses. Of the 11 disaccharides separated in the standard mixes, only eight of these are detected in the HS digests. Other small signals are seen on the baseline of the electrophoretograms of the digests and these may correspond to oligosaccharides >2 dp. As mentioned above, the larger oligosaccharides will have less UV absorbance compared with the disaccharides.

Figure 24:
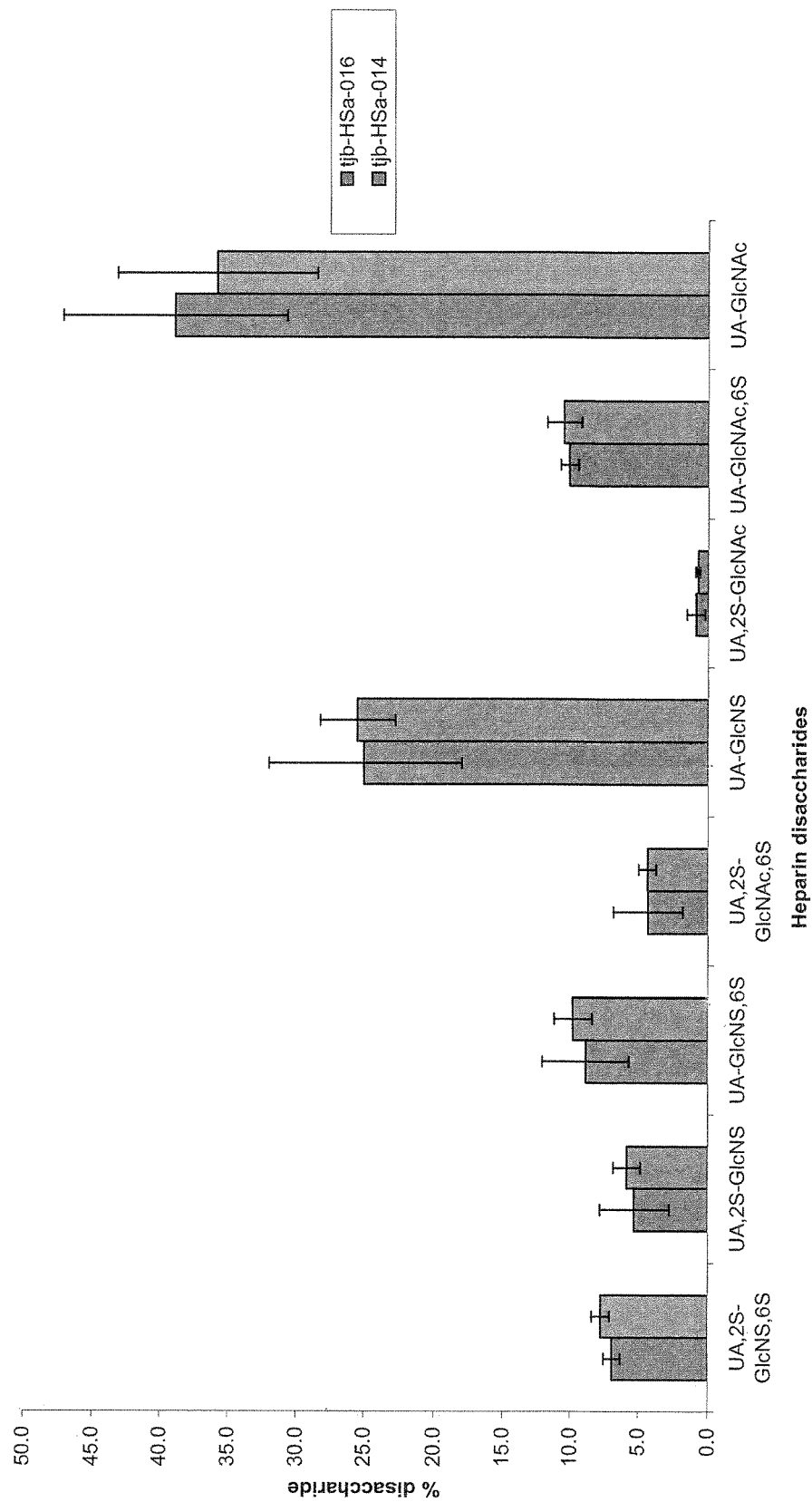
FIG. 24. Graph showing normalized disaccharide composition for Celsus HS.

Duplicate analyses were completed on a sample of Celsus HS (Lot #10697) and compared to a previous set of analyses on the same sample: these results are displayed in FIG. 24. Excellent correlation between the two sets of analyses was observed. The proportion of the eight disaccharides in the Celsus HS digests were similar to other previous analyses with a large component of ΔUA-GlcNAc and ΔUA-GlcNS and lesser proportions of ΔUA-GlcNAc,6S, ΔUA-GlcNS,6S and ΔUA,2S-GlcNS,6S (FIG. 24). This corresponds to the large proportion of mono- and unsulfated disaccharide lesser proportions of disulfated disaccharide and small proportion of trisulfated disaccharide consistent with HPLC-SEC profiles. The non-retained HS is enriched in the mono- and un-sulfated disaccharides compared with the Celsus HS starting material. This pattern for the non-retained material was also seen quite distinctly in HPLC-SEC chromatograms. In the case of the analyses of HS8 the sample size permitted only a single analysis and so no error data is provided for this preparation. Comparison of HS8, HS3 and Celsus HS is displayed in FIG. 26.

The disaccharide composition for HS8 is comparable to that of HS3 (an HS isolated from Celsus HS through affinity for a heparin bidding domain from BMP2, as described in WO2010/030244) in that a more sulfated (charged) fraction has in general been prepared from the Celsus HS. However; there is a striking difference in that there is a greater proportion of UA-GlcNS,6s and a lesser proportion of US-GlcNS for HS8 in comparison to HS3.

Raw Celsus HS from which HS8 was derived has an average molecular weight of 20-25 kDa (compared with ~15 kDa for heparin), and the process of identifying HS8 by affinity chromatography did not result in a substantial change in the observed molecular weight of HS chains. Each disaccharide unit is expected to have a molecular weight in the range ~430 to ~650 KDa. Using a rough average of 500 daltons per disaccharide (the average disaccharide in heparin is ~650 daltons, for example), indicates (as a basic approximation) a chain length for HS8 of about 44 rings per average (22 kDa) HS8.

Example 10

HS8 Modulates Endogenous FGF-2 Expression and Distribution

Protocol

To determine the effect of HS8 on the amount of endogenous FGF-2, primary human epidermal keratinocytes are treated with HS8 for a total of 4 days. Keratinocytes are plated in a defined keratinocyte serum free culture medium. Twenty-four hours after plating, HS8 is added into the culture medium. A complete medium change with fresh dose of HS8 is performed on alternate days. Conditioned medium and cell lysate are collected at the end of the culture period and quantified for endogenous level of FGF-2 through ELISA.

To determine the stability of FGF-2 in the presence of HS8, endogenous FGF-2 is collected from keratinocyte culture medium and treated with HS8. Keratinocytes are maintained at up to 70% confluency before a complete medium change. After 24 h, keratinocyte conditioned medium is collected and treated with or without the specified dose of HS8 and incubated at 37° C./5% $CO_2$. The conditioned medium is sampled at 2, 4, 6, 10, 24 and 48 h, and FGF-2 is quantified through ELISA.

Results

The results are given in FIGS. 29 and 30.

HS8 modulates the amount of endogenous FGF-2 secreted by human epidermal keratinocytes (FIG. 29). This is demonstrated by 2.3 and 3.7 fold increase in FGF-2 protein in the keratinocytes conditioned medium in the presence of 0.625 and 2.5 µg/mL HS8 respectively. In turn, a decrease in FGF-2 level by 0.5 fold on the cell lysate, representing the cell layer and ECM compartment, is observed in the presence of 2.5 but not 0.625 µg/mL HS8.

Together, the results suggest that the increase in the amount of FGF-2 in the culture medium is partially attributed to the shift in the distribution of FGF-2 from being bound to the cell surface and matrix to dissociate and bind to soluble HS8 present in the medium. However, the 50% decrease in the amount of FGF-2 in the cell layer does not fully account for the 371% increase in FGF-2 found in the conditioned medium.

HS8 also modulates the stability of endogenous FGF-2 in the keratinocyte conditioned medium (FIG. 30). Endogenous FGF-2 is relatively stable for up to 6 h in keratinocyte culture medium under physiological condition. The stabilizing effect of HS8 is observed after 10 h incubation onwards. At 48 h, the amount of FGF-2 incubated in HS8 is significantly higher by 34% compared to control.

HS8 shows anti-aging efficacy by enhancing FGF-2 growth factor level in the epidermal compartment through modulating its stability and distribution, thus boosting skin renewal capacity.

Example 11

HS8 Modulates Dermal Fibroblast Proliferation

Protocol

Human dermal fibroblasts are plated in fibroblast culture medium supplemented with 10% fetal bovine serum. Twenty-four hour after plating, the cells are treated with increasing dose of HS8 for a total of 4 days. A complete medium change with a fresh dose of HS8 is performed on alternate days. At the end of the treatment, the cells are trypsinized and counted in an automated cell counter in order to determine fibroblast proliferation.

In order to determine whether the effect of HS8 on fibroblast proliferation is mediated through FGF-2 activity, 2 types of FGF receptor (FGFR) inhibitors are used. IMB-R1 is a proprietary FGFR-1, the main receptor to FGF-2, antibody developed by Singapore's Institute of Medical Biology to neutralize FGF-2 activity through FGFR-1 inhibition. PD173074 is a commercial chemical inhibitor that selectively inhibits FGFR-1 and -3. Dermal fibro-blasts are treated with PD173074 in the absence/presence of HS8 24 h after plating. Full medium change containing the treatment is performed on alternate days. Cells are harvested and counted 4 days after treatment. Dermal fibroblasts are treated with IMB-R1 in the absence/presence of HS8 3 days after plating. Cells are harvested and counted 2 days after treatment.

Results

The results are given in FIGS. 31 and 32.

Figure 32B:
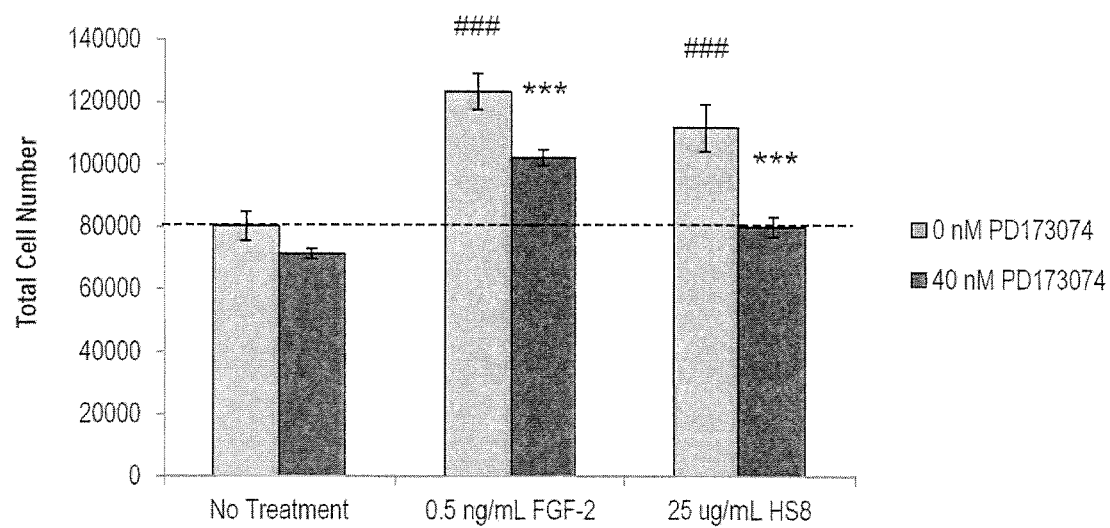

HS8 significantly increases dermal fibroblast proliferation by up to 49% compared to untreated control (FIG. 31). The contribution of FGF-2 to HS8-induced fibroblast proliferation is demonstrated through the inhibition of HS8-induced proliferation in the presence of either IMB-R1 (FIG. 32A) or PD173074 (FIG. 32B).

HS8 demonstrates anti-aging efficacy by boosting the renewal of fibroblast cells, which are the major cell type within the dermal component that plays a role in ECM deposition and organization.

Example 12

HS8 Modulates Keratinocytes Differentiation Markers

Protocol

Keratinocytes are plated in a defined keratinocyte serum free culture medium. Twenty-four hour after plating, HS8 is added into the culture medium. A complete medium change with fresh HS8 dose is performed on alternate days. After a total of 4 days of HS8 treatment, total mRNA is harvested from the cultured cells, reverse-transcribed and amplified through real-time PCR to quantify transcript expression of several keratinocyte differentiation markers. Keratin 10 (K10), keratin 14 (K14), involucrin (Inv) and transglutaminase-1 (TGM1) are assayed along with glyceraldehyde 3-phosphate dehydrogenase (GAPDH) as the endogenous control.

Results

The results are given in FIG. 33.

HS8 modulates keratinocytes differentiation markers as demonstrated by its effect on the transcript expression of K10, K14, Inv and TGM1 (FIG. 33). HS8 significantly decreases the transcript level of K10, a basal keratinocytes marker, and K14, a marker for keratinocytes in the spinous layer. HS8 also significantly decreases the transcript level of Inv and TGM1, which are both crucial components in keratinocytes cornification and terminal differentiation.

The effect of HS8 on keratinocyte differentiation markers K10, Inv and TGM1 is similar to retinoic acid, a well-established anti-aging active compound known to decrease epidermal differentiation.

Example 13

HS8 Modulates Keratinocytes Motility

Protocol

Human primary keratinocytes are seeded at low density in defined keratinocyte serum free medium in collagen coated tissue culture plate with the indicated treatment conditions. The cells are fixed in 4% paraformaldehyde and permeabilized with 0.1% Triton-X after 48 h. The migratory pathways of keratinocytes are stained with laminin V antibody and its corresponding horseradish peroxidase-conjugated secondary antibody.

Cell motility was determined based on the distance and directionality of the cell movement and classified into 3 categories: non-motile, motile and hyper-motile cells.

Results

The results are given in FIG. 34.

HS8 modulates keratinocytes motility as demonstrated by the increase in the percentage of motile (32%) and hyper-motile (27%) cells compared to untreated control (9% and 6% respectively) after 48 h treatment (FIG. 34). The effect of HS8 on keratinocyte motility is comparable to the effect of the positive control containing TGF-β1 treatment. FGF-2 alone moderately increases cell motility by increasing the percentage of motile cells from 9% to 17% compared to untreated control. The combination of FGF-2 and HS8 at the specified concentration does not further increase cell motility.

HS8 shows anti-aging effect by promoting keratinocyte cell migration, which can help fill in lines and induce smoother appearance of the epidermis, especially after exfoliation methods.

Example 14

Examples of cosmetic compositions comprising HS8 are provided below. These compositions may be produced according to classical methods known from the man skill in the art.

Composition 1: Oil in Water Cream:

| | |
|---|---|
| Glycerol monostearate | 6.0% |
| Stearyl alcohol | 4.0% |
| Vaseline oil | 10.0% |
| Silicone oil | 5.0% |
| HS8 compound according to the invention | 0.025% |
| Glycerin | 8.0% |
| Carboxyvinylpolymer (Carbopol) | 0.3% |
| Perfume | 0.5% |
| Triethanolamine | 0.3% |
| Water | up to 100% |

Composition 2: Water in Oil Cream (W/O):

| | |
|---|---|
| Octyl dodecanol | 10.0% |
| Magnesium stearate | 4.0% |
| Wax | 5.0% |
| Sorbitan sesquioleate | 4.5% |
| Glycerol mono- and distearate and potassium stearate | 1.0% |
| Vaseline oil | 22.0% |
| Jojoba oil | 4.0% |
| HS8 compound according to the invention | 0.05% |
| Perfume | 0.6% |
| Water | up to 100% |

Composition 3: Moisturizing Gel:

| | |
|---|---|
| HS8 compound according to the invention | 0.025% |
| Glycerin | 12.0% |
| Acrylamide/acrylamido-2-methyl propane sodium sulfonate in 40% isoparaffin/water (305 SEPIGEL type) | 5.0% |
| Mixture of polydimethylsiloxane-alpha omega hydroxy groups and cyclopenta dimethylsiloxane (15/85) | 2.0% |
| Preservative | 0.4% |
| Perfume | 0.6% |
| Water | up to 100% |

Example 15

HS8 Modulates Basal Keratinocytes Proliferation

Protocol

Reconstructed full-thickness skin model containing dermal fibroblasts embedded in collagen hydrogel and a layer of keratinocytes that has been raised into air-liquid interface to produce stratified epidermal layer is treated at day-20 with maintenance medium or medium containing either 25 µg/mL HS8 or 2.5 ng/mL FGF-2. Full medium change with treatment is performed at day-22. At day-25, the samples are harvested for viability assay and histology. Formalin Fixed Paraffin Embedded (FFPE) samples were sectioned and stained with antibody against Ki67 in Bond-Max staining instrument.

Results

The results are given in FIG. 35.

HS8 enhances basal keratinocytes proliferation as observed by an increase in cell nuclei stained with Ki67, a cellular proliferation marker (FIG. 35). The increase in the number of proliferative cells are significantly higher in tissues treated with HS8 compared to untreated samples or those treated with FGF-2.

Aging epidermis is associated with a decrease in cell proliferation and epidermal thinning.

The capability of HS8 to stimulate basal keratinocyte proliferation suggests anti-aging property of HS8.

Example 16

HS8 Modulates Dermal Epidermal Junction Protein Expression

Protocol

Reconstructed full-thickness skin model containing dermal fibroblasts embedded in collagen hydrogel and a layer of keratinocytes that has been raised into air-liquid interface to produce stratified epidermal layer is treated at day-20 with maintenance medium or medium containing either 25 µg/mL HS8 or 2.5 ng/mL FGF-2. Full medium change with treatment is performed at day-22. At day-25, the samples are harvested for viability assay and histology. Formalin Fixed Paraffin Embedded (FFPE) samples were sectioned and stained using antibody against Collagen IV or Laminin 5 γ2 in Bond-Max staining instrument.

Results

The results are given in FIGS. 36 and 37.

HS8 enhances the expression of dermal epidermal junction (DEJ) markers Laminin 5 γ2 (FIG. 36) and Collagen IV (FIG. 37) as measured by the area of staining along the DEJ normalized to the length of the DEJ analyzed. The expression of these DEJ markers are significantly higher in HS8-treated samples than untreated and FGF-2 treated samples.

Changes to the DEJ is one of the characteristics of aging skin. Collagen IV and Laminin 5 γ2 are important components that allow better attachment of keratinocytes on the basement membrane. A better expression of these proteins is postulated to strengthen the cohesion and mechanical resistance of the skin.

REFERENCES

1. Ashikari-Hada, S., Habuchi, H., Kariya, Y., Itoh, N., Reddi, A. H., and Kimata, K. (2004). Characterization of Growth Factor-binding Structures in Heparin/Heparan Sulfate Using an Octasaccharide Library. The Journal of Biological Chemistry 279(1)3, 12346-12354
2. Baird, A., Schubert, D., Ling, N., and Guillemin, R. (1988). Receptor- and heparin-binding domains of basic fibroblast growth factor. Proc. Natl. Acad. Sci. USA 85, 2324-2328.
3. Billingham, R. E. (1966-67). The biology of graft-versus-host reactions. Harvey Lect 62, 21-78.
4. Bishop, J. R., Schuksz, M., and Esko, J. D. (2007). Heparan sulphate proteoglycans fine-tune mammalian physiology. Nature 446, 1030-1037
5. Brickman, Y. G., Ford M. D., Small, D. H., Bartletti, P., F., and Nurcombe, V. (1995). Heparan sulfates mediate the binding of basic fibroblast growth factor to a specific receptor on neural precursor cells. J Biolo. Chem. 270 (42), 24941-24948.

6. Brickman, Y. G., Nurcombe, V., Ford, M. D., Gallagher, J. T., Bartlett, P. F. and Turnbull, J. E. (1998). Structural comparison of fibroblast growth factor-specific heparan sulfates derived from a growing or differentiating neuroepithelial cell line. Glycobiology 8(5), 463-471.
7. Cain, S. A., Baldock, C., Gallagher, j., Morgan, A., Bax D. V., Weiss, A. S., Shuttleworth, A. C., and Kielty C. M. (2005). Fibrillin-1 Interactions with heparin-Implications for microfibril and elastic fibre assembly. The Journal of biological Chemistry 280(34), 30526-30537.
8. Caplan, A. I. (2009). Why are MSCs therapeutic? New data: new insight. J Pathol 217, 318-324
9. Cardin, A. D., and Weintraub, H. J. (1989), Molecular modeling of protein-glycosaminoglycan interactions. Arterioscler. Thromb. Vasc. Biol. 9, 21-32
10. Cawthon, R. M. (2002) Telomere measurement by quantitative PCR. Nucleic Acids Res 30, e47.
11. Cool, S. M., and Nurcombe, V. (2005) Substrate Induction of Osteogenesis from Marrow-Derived Mesenchymal Precursors. Stem Cells Dev. 14(6), 632-642.
12. Dominici, M., Le Blanc, K., Mueller, I., Slaper-Cortenbach, I., Marini, F. C., Krause, D. S., Deans R. J., Keating, A., Prockop, D. J., and Horwitz, E. M. (2006). Minimal criteria for defining multipotent mesenchymal stromal cells. The International Society for Cellular Therapy position statement. Cytotherapy 8(4), 315-317
13. Esch, F., Baird, A., Ling, N., et al. (1985) Primary structure of bovine pituitary basic fibroblast growth factor (FGF) and comparison with the amino-terminal sequence of bovine brain acidic FGF. Proc Natl Acad Sci USA; 82:6507-6511
14. Faham, S., Hileman, R. E., Fromm, J. R., Linhardt, R. J., and Rees, D. C. (1996) Heparin structure and interactions with basic fibroblast growth factor. Science 271, 1116-1120
15. Ferrara, J. L. M., Levine, J. E., Reddy, P., and Holler, E. (2009). Graft-versus-host disease. Lancet 373, 1550-61
16. Fromm, J. R., Hileman, R. E., Caldwell, E. E., Weiler, J. M., and Linhardt, R. J. (1997). Pattern and spacing of basic amino acids in heparin binding sites. Arch. Biochem. Biophys. 343, 92-100
17. Gandhi, N. S., and Mancera, R. L. (2008). The Structure of glycosaminoglycans and their interactions with proteins. Chem. Biol. Drug. Des. (2008) 72, 455-482
18. Gronthos, S., Zannettino, A. C. W., Graves, S. E., Ohta, S., Hay, S. J., and Simmons, P. J. (1999). Differential cell surface expression of the STRO-1 and alkaline phosphatase antigens on discrete developmental stages in primary cultures of human bone cells. J. Bone Min. Res. 14(1), 47-56.
19. Grünert, M., Dombrowski, C., Sadasivam, M., Manton, K., Cool, S. M., and Nurcombe, V. (2007). Isolation of a native osteoblast matrix with a specific affinity for BMP2. J. Mol. Histo 38, 393-404.
20. Guillot, P. V., Gotherstrom, C., Chan, J., Kurata, H. and Fisk, N. M. (2007) Human first-trimester fetal MSC express piuripotency markers and grow faster and have longer telomeres than adult MSC. Stem Cells 25, 646-654.
21. Hileman, R. E., Fromm, J. R., Weiler, J. M., and Linhardt, R. J. (1998). Glycosaminoglycan-protein interactions: definition of consensus sites in glycosaminoglycan binding proteins. *Bioessays* 20(2), 156-67
22. Kinsella, L., Chen, H., Smith, J. A., Rudland, P. S., and Fernig D. G. (1998). Interactions of putative heparin-binding domains of basic fibroblast growth factor and its receptor, FGFR-1, with heparin using synthetic peptides. Glycoconjugate Journal 15, 419-422
23. Le Blanc, K., Frassoni F., Ball, L., Locatelli, F, Roelots, H., Lewis, I., Lanino, E., Sundberq, B., Bernardo, M. E., Remberger, M., Dini, G., Egeler, R. M., Bacigalupo, A., and Fibbe, W., Ringdén, O. (2008). Mesenchymal stem cells for treatment of steroid-resistant, severe, acute graft-versus-host disease: a phase II study. Lancet 371, 1579-1586
24. Lee, J. Y., Choo, J. E., Choi, Y. S., Lee, K. Y., Min, D. S., Pi, S. H., Seol, Y. J., Lee, S. J., Jo, I. H., Chung, C. P., and Park, Y. J. (2007). Characterization of the surface immobilized synthetic heparin binding domain derived from human fibroblast growth factor-2 and its effect on osteoblast differentiation. *J Biomed Mater Res A* 15; 83(4), 970-9.
25. Matsubara, T., Tsutsumi. S., Pan, H., Hiraoka, H., Oda, R., Nishimura, M., Kawaguchi, H., Nakamura, K., and Kato, Y. (2004). A new technique to expand human mesenchymal stem cells using basement membrane extracellular matrix. Biochemical and Biophysical Research Communications 313(3), 503-508
26. Meuleman, N., Tondreau, T., Ahmad, I., Kwan J., Crokaert, F., Delforge, A., Dorval, C., Martiat, P., Lewalle, P., Lagneaux, L., and Bron D. (2009). Infusion of mesenchymal stromal cells can aid hematopoietic recovery following allogeneic hematopoietic stem cell myeloablative transplant: a pilot study. *Stem Cells Dev.* 18(9), 1247-52.
27. Murali, S., Manton, K. J., Tjong, V., Su, X., Haupt, L. M, Cool, S. M., and Nurcombe, V. (2009) Purification and characterization of heparan sulfate from human primary osteoblasts. Journal of cellular biochemistry 108, 1132-1142 (2009)
28. Nurcombe, V., Ford, M. D., Wildschut, J. A., and Bartlett, P. F. (1993). Developmental regulation of neural response to FGF-1 and FGF-2 by heparan sulfate proteoglycan. Science, 260(5104), 103-106.
29. Ono, K., Hattori, H., Takeshita, S., Kurita, A., and Ishihara, M. (1999). Structural features in heparin that interact with VEGF165 and modulate its biological activity. Glycobiology. 9(7), 705-11.
30. Ornitz, D. M., Xu, J., Colvin, J. S., McEwen, D. G., MacArthur, C. A., Coulieri, F., Gao, G., and Goldfarb, M. (1996). Receptor Specificity of the Fibroblast Growth Factor Family. J Biol. Chem. 271(25), 15292-15297
31. Ori, A., Free, P., Courty, J., Wilkinson, M. C., and Fernig D. G. (2009). Identification of Heparin-binding Sites in Proteins by Selective Labeling. Molecular & Cellular Proteomics 8, 2256-2265
32. Ori, A., Wilkinson, M. C., and Fernig, D. G., (2008). The heparanome and regulation of cell function: structures, functions and challenges. *Front Biosci. f* (13), 4309-38.
33. Pellegrini, L. (2001). Role of heparan sulfate in fibroblast growth factor signalling: a structural view. Curr. Opin. Struc. Biol. 11, 629-634
34. Ren, G. S, J., Zhang, L., zhao, X., Ling, W., L'huillie, A., Zhang, J., Lu, Y., Roberts, A. I., Ji, W., Zhang, H., Rabson, A. B., and Shi, Y. (2009). Species Variation in the Mechanisms of Mesenchymal Stem Cell-Mediated Immunosuppression. Stem cells 27, 1954-1962
35. Shi, Y., Hu, G., Su, J., Li, W., Chen, C., Shou, P. Xu, C, Chen, X., Huang, Y., Zhu, Z., Huang, X., Han, X., Xie, N., and Ren, G. (2010). Mesenchymal stem cells: a new strategy for immunosuppression and tissue repair. Cell Research 20, 510-518.

36. Si, Y. L., Zhao, Y. L., Hao, H. J., Fu, X. B., and Han, W. D. (2011). MSCs: Biological characteristics, clinical applications and their outstanding concerns. Ageing Research Reviews 10, 93-103
37. Sotiropoulou, P. A., Perez, S. A., Salagianni, M., Baxevanis, C. N, and Papamichail, M. (2006). Characterization of the Optimal Culture Conditions for Clinical Scale Production of Human Mesenchymal Stem Cells. Stem cells 24, 462-471
38. Tisato, V., Naresh, K., Girdlestone, J., Navarrete, C., and Dazzi, F. (2007). Mesenchymal stem cells of cord blood origin are effective at preventing but not treating graft-versus-host disease. Leukemia 21, 1992-9.
39. Toubai, T., Paczesny, S., Shono, Y., Tanaka, J., Lowler, K. P., Malter, C, T., Kasai, M., and Imamura M. (2009). Mesenchymal stem cells for treatment and prevention of graft-versus-host disease after allogeneic hematopoietic cell transplantation. Curr, *Stem. Cell. Res. Ther.* 4(4), 252-9.
40. Thompson, L. D., Pantoliano, M. W., and Springer B. A. (1994). Energetic characterization of the basic fibroblast growth factor-heparin interaction: identification of the heparin binding domain. Biochemistry 33, 3831-3840
41. Uniewicz, K. A., Ori, A., Xu, R., Ahmed, Y., Wilkinson, M. C., Fernig, D. G., and Yates, E. A. (2010). Differential Scanning Fluorimetry Measurement of Protein Stability Changes upon Binding to Glycosaminoglycans: A Screening Test for Binding Specificity. Anal. Chem., 82 (9), 3796-3802
42. Walsh, S., Jefferiss, C., Stewart, K., Jordan, G. R., Screen, J., and Beresford, J. N. (2000). Expression of the developmental markers STRO-1 and alkaline phosphatase in cultures of human marrow stromal cells: regulation by fibroblast growth factor (FGF)-2 and relationship to the expression of FGF receptors 1-4. Bone 27(2). 185-195.
43. Zannettino A, C., Paton. S., itescu, S., and Gronthos, S. (2010). Comparative assessment of the osteoconductive properties of different biomaterials in vivo seeded with human or ovine mesenchymal stem/stromal cells. *Tissue Eng Part A.* 16(12), 3579-87.
44. Zulma Gazit, Z., Pelled, G. Sheyn, D., Kimelman, N. and Gazit, N. (2011). Mesenchymal Stem Cells. Principles of Regenerative Medicine Chapter 17, 285-304
45. Friedenstein A J, Piatetzky S II, Petrakova K V (1966) Osteogenesis intransplants of bone marrow cells. J Embryol Exp Morphol 16:381-390
46. Gimble J, Guilak F (2003) Adipose-derived adult stem cells: isolation, characterization, and differentiation potential. Cytotherapy 5:362-369
47. Zuk P A, Zhu M, Mizuno H, Huang J, Futrell J W, Katz A J, Benhaim P, Lorenz H P, Hedrick M H (2001) Multilineage cells from human adipose tissue: implications for cell-based therapies. Tissue Eng 7:211-228
48. Bieback K, Kern S, Kluter H, Eichler H (2004) Critical parameters for the isolation of mesenchymal stem cells from umbilical cord blood. Stem Cells 22:625-634
49. Erices A, Conget P, Minguell J J (2000) Mesenchymal progenitor cells in human umbilical cord blood. Br J Haematol 109:235-242
50. Goodwin H S, Bicknese A R, Chien S N, Bogucki B D, Quinn C O, Wall D A (2001) Multilineage differentiation activity by cells isolated from umbilical cord blood: expression of bone, fat, and neural markers. Biol Blood Marrow Transplant 7:581-588
51. Kogler G, Sensken S, Airey J A, Trapp T, Muschen M, Feldhahn N, Liedtke S, Sorg R V, Fischer J, Rosenbaum C et al (2004) A new human somatic stem cell from placental cord blood with intrinsic pluripotent differentiation potential. J Exp Med 200:123-135
52. Wagner W, Wein F, Seckinger A, Frankhauser M, Wirkner U, Krause U, Blake J, Schwager C, Eckstein V, Ansorge W, Ho A D (2005) Comparative characteristics of mesenchymal stem cells from human bone marrow, adipose tissue, and umbilical cord blood. Exp Hematol 33:1402-1416
53. Jiang Y, Vaessen B, Lenvik T, Blackstad M, Reyes M, Verfaillie C M (2002) Multipotent progenitor cells can be isolated from postnatal murine bone marrow, muscle, and brain. Exp Hematol 30:896-904
54. Nakazimo S, Egawa G, Doi H, Natsuaki Y, Miyachi Y, Kabashima K. Topical Treatment with Basic Fibroblast Growth Factor Promotes Wound Healing and Barrier Recovery Induced by Skin Abrasion. Skin Pharmacol Physiol. 2012. 26(1):22-29.
55. Sogabe Y, Abe M, Yokoyama Y, Ishikawa O. Basic Fibroblast growth factor stimulates human keratinocyte motility by Rac activation. Wound Repair Regen. 2006. 14(4):457-62
56. Matrix therapy with RGTA OTR4120 improves healing time and quality in hairless rats with deep second-degree burns Zakine G, Barbier V, Garcia-Filipe S, Luboinski J, Papy-Garcia D, Chachques J C, Carpentier A, Barritault D. Plast Reconstr Surg. 2011 February; 127(2):541-50
57. Priming with proangiogenic growth factors and endothelial progenitor cells improves revascularization in linear diabetic wounds. Ackermann M, Pabst A M, Houdek J P, Ziebart T, Konerding M A. Int J Mol Med. 2014 April; 33(4):833-9

The invention claimed is:

1. A cosmetic process for caring for keratinous material(s), the process comprising application or administration of heparan sulphate HS8, or a composition comprising heparan sulphate HS8, to keratinous material(s), wherein the heparan sulphate HS8 is capable of binding a peptide or polypeptide having, or consisting of, the amino acid sequence YCKNGGF (SEQ ID NO:2) or GHFKDPKRLYCKNGGF (SEQ ID NO:1).

2. The process of claim 1, wherein the keratinous material(s) is selected from one or more of human skin, hair or nails.

3. The process of claim 1, wherein heparan sulphate HS8 is used or is present in the composition in a content ranging from 0.0001% to 5% by weight, relative to the total weight of the composition.

4. The process of claim 1, wherein said process is intended to decrease the signs of ageing of the keratinous material(s).

5. The process of claim 1, wherein said process is intended to maintain and/or stimulate moisturization and/or combat drying-out of the keratinous material(s).

6. The process of claim 2, wherein said process is intended to:
   (i) decrease characteristics of wrinkles, small wrinkles and/or fine lines of the skin;
   (ii) improve and/or decrease the microrelief of the skin;
   (iii) smooth the skin;
   (iv) improve the density of the skin;
   (v) maintain and /or restore skin elasticity;
   (vi) maintain and/or restore skin firmness; or
   (vii) maintain and/or restore the cohesion of skin compartments.

7. A cosmetic method of regulating a skin condition, comprising applying or administering to the skin of a human individual a safe and effective amount of heparan sulphate HS8, or a composition comprising heparan sulphate HS8, wherein the heparan sulphate HS8 is capable of binding a peptide or polypeptide having, or consisting of, the amino acid sequence YCKNGGF (SEQ ID NO:2) or GHFKDPKRLYCKNGGF (SEQ ID NO:1).

8. The cosmetic method of claim 7 wherein the method comprises improving skin appearance and/or feel.

9. The cosmetic method of claim 7, wherein the method comprises regulating visible and/or tactile discontinuities in skin texture.

10. The process of claim 1 wherein the heparan sulphate HS8 is provided in isolated or substantially purified form.

11. The process of claim 1 wherein following digestion with heparin lyases I, II and Ill and then subjecting the resulting disaccharide fragments to capillary electrophoresis analysis the heparan sulphate HS8 has a disaccharide composition comprising:

| Disaccharide | Normalised weight percentage |
| --- | --- |
| ΔUA,2S-GlcNS,6S | 12.7 ± 3.0 |
| ΔUA,2S-GlcNS | 7.2 ± 2.0 |
| ΔUA-GlcNS,6S | 15.5 ± 3.0 |
| ΔUA,2S-GlcNAc,6S | 6.5 ± 2.0 |
| ΔUA-GlcNS | 15.7 ± 3.0 |
| ΔUA,2S-GlcNAc | 1.0 ± 0.5 |
| ΔUA-GlcNAc,6S | 8.9 ± 3.0 |
| ΔUA-GlcNAc | 32.5 ± 3.0. |

* * * * *

SEQUENCE LISTING

<160> NUMBER OF SEQ ID NOS: 15

<210> SEQ ID NO 1
<211> LENGTH: 16
<212> TYPE: PRT
<213> ORGANISM: Homo sapiens

<400> SEQUENCE: 1

Gly His Phe Lys Asp Pro Lys Arg Leu Tyr Cys Lys Asn Gly Gly Phe
1               5                   10                  15

<210> SEQ ID NO 2
<211> LENGTH: 7
<212> TYPE: PRT

<213> ORGANISM: Homo sapiens

<400> SEQUENCE: 2

Tyr Cys Lys Asn Gly Gly Phe
1               5

<210> SEQ ID NO 3
<211> LENGTH: 288
<212> TYPE: PRT
<213> ORGANISM: Homo sapiens

<400> SEQUENCE: 3

Met Val Gly Val Gly Gly Asp Val Glu Val Thr Pro Arg Pro
1               5                   10                  15

Gly Gly Cys Gln Ile Ser Gly Arg Gly Ala Arg Gly Cys Asn Gly Ile
            20                  25                  30

Pro Gly Ala Ala Ala Trp Glu Ala Ala Leu Pro Arg Arg Arg Pro Arg
        35                  40                  45

Arg His Pro Ser Val Asn Pro Arg Ser Arg Ala Ala Gly Ser Pro Arg
    50                  55                  60

Thr Arg Gly Arg Arg Thr Glu Glu Arg Pro Ser Gly Ser Arg Leu Gly
65                  70                  75                  80

Asp Arg Gly Arg Gly Arg Ala Leu Pro Gly Gly Arg Leu Gly Gly Arg
                85                  90                  95

Gly Arg Gly Arg Ala Pro Glu Arg Val Gly Arg Gly Arg Gly Gly Arg
            100                 105                 110

Gly Thr Ala Ala Pro Arg Ala Ala Pro Ala Ala Arg Gly Ser Arg Pro
        115                 120                 125

Gly Pro Ala Gly Thr Met Ala Ala Gly Ser Ile Thr Thr Leu Pro Ala
    130                 135                 140

Leu Pro Glu Asp Gly Gly Ser Gly Ala Phe Pro Pro Gly His Phe Lys
145                 150                 155                 160

Asp Pro Lys Arg Leu Tyr Cys Lys Asn Gly Gly Phe Phe Leu Arg Ile
                165                 170                 175

His Pro Asp Gly Arg Val Asp Gly Val Arg Glu Lys Ser Asp Pro His
            180                 185                 190

Ile Lys Leu Gln Leu Gln Ala Glu Glu Arg Gly Val Val Ser Ile Lys
        195                 200                 205

Gly Val Cys Ala Asn Arg Tyr Leu Ala Met Lys Glu Asp Gly Arg Leu
    210                 215                 220

Leu Ala Ser Lys Cys Val Thr Asp Glu Cys Phe Phe Phe Glu Arg Leu
225                 230                 235                 240

Glu Ser Asn Asn Tyr Asn Thr Tyr Arg Ser Arg Lys Tyr Thr Ser Trp
                245                 250                 255

Tyr Val Ala Leu Lys Arg Thr Gly Gln Tyr Lys Leu Gly Ser Lys Thr
            260                 265                 270

Gly Pro Gly Gln Lys Ala Ile Leu Phe Leu Pro Met Ser Ala Lys Ser
        275                 280                 285

<210> SEQ ID NO 4
<211> LENGTH: 7
<212> TYPE: PRT
<213> ORGANISM: Homo sapiens

<400> SEQUENCE: 4

Tyr Lys Arg Ser Arg Tyr Thr
1               5

```
<210> SEQ ID NO 5
<211> LENGTH: 7
<212> TYPE: PRT
<213> ORGANISM: Homo sapiens

<400> SEQUENCE: 5

Tyr Arg Ser Arg Lys Tyr Thr
1               5

<210> SEQ ID NO 6
<211> LENGTH: 17
<212> TYPE: PRT
<213> ORGANISM: Homo sapiens

<400> SEQUENCE: 6

Lys Arg Thr Gly Gln Tyr Lys Leu Gly Ser Lys Thr Gly Pro Gly Gln
1               5                   10                  15

Lys

<210> SEQ ID NO 7
<211> LENGTH: 18
<212> TYPE: PRT
<213> ORGANISM: Homo sapiens

<400> SEQUENCE: 7

Leu Lys Arg Thr Gly Gln Tyr Lys Leu Gly Ser Lys Thr Gly Pro Gly
1               5                   10                  15

Gln Lys

<210> SEQ ID NO 8
<211> LENGTH: 28
<212> TYPE: PRT
<213> ORGANISM: Homo sapiens

<400> SEQUENCE: 8

Phe Phe Phe Glu Arg Leu Glu Ser Asn Asn Tyr Asn Thr Tyr Arg Ser
1               5                   10                  15

Arg Lys Tyr Thr Ser Trp Tyr Val Ala Leu Lys Arg
            20                  25

<210> SEQ ID NO 9
<211> LENGTH: 10
<212> TYPE: PRT
<213> ORGANISM: Homo sapiens

<400> SEQUENCE: 9

Val Arg Glu Lys Ser Asp Pro His Ile Lys
1               5                   10

<210> SEQ ID NO 10
<211> LENGTH: 10
<212> TYPE: PRT
<213> ORGANISM: Homo sapiens

<400> SEQUENCE: 10

Ser Arg Lys Tyr Thr Ser Trp Tyr Val Ala
1               5                   10

<210> SEQ ID NO 11
<211> LENGTH: 14
<212> TYPE: PRT
<213> ORGANISM: Homo sapiens
```

```
<400> SEQUENCE: 11

Leu Lys Arg Thr Gly Gln Tyr Lys Leu Gly Ser Lys Thr Gly
1               5                   10

<210> SEQ ID NO 12
<211> LENGTH: 21
<212> TYPE: PRT
<213> ORGANISM: Homo sapiens

<400> SEQUENCE: 12

Leu Lys Arg Thr Gly Gln Tyr Lys Leu Gly Ser Lys Thr Gly Pro Gly
1               5                   10                  15

Gln Lys Ala Ile Leu
            20

<210> SEQ ID NO 13
<211> LENGTH: 17
<212> TYPE: PRT
<213> ORGANISM: Homo sapiens

<400> SEQUENCE: 13

Lys Arg Thr Gly Gln Tyr Lys Leu Gly Ser Lys Thr Gly Pro Gly Gln
1               5                   10                  15

Lys

<210> SEQ ID NO 14
<211> LENGTH: 10
<212> TYPE: PRT
<213> ORGANISM: Homo sapiens

<400> SEQUENCE: 14

Leu Ala Met Lys Glu Asp Gly Arg Leu Leu
1               5                   10

<210> SEQ ID NO 15
<211> LENGTH: 18
<212> TYPE: PRT
<213> ORGANISM: Artificial sequence
<220> FEATURE:
<223> OTHER INFORMATION: Synthetic peptide
<220> FEATURE:
<221> NAME/KEY: SITE
<222> LOCATION: (17)..(17)
<223> OTHER INFORMATION: Xaa is Ahx
<220> FEATURE:
<221> NAME/KEY: SITE
<222> LOCATION: (18)..(18)
<223> OTHER INFORMATION: Lys is (K)Biotin

<400> SEQUENCE: 15

Gly His Phe Lys Asp Pro Lys Arg Leu Tyr Cys Lys Asn Gly Gly Phe
1               5                   10                  15

Xaa Lys
```